US009102983B2

(12) United States Patent
Winkler et al.

(10) Patent No.: US 9,102,983 B2
(45) Date of Patent: Aug. 11, 2015

(54) SINGLE NUCLEOTIDE POLYMORPHISMS ASSOCIATED WITH RENAL DISEASE

(75) Inventors: Cheryl Winkler, Gaithersburg, MD (US); George Nelson, Thurmont, MD (US); Jeffrey B. Kopp, Bethesda, MD (US); Michael W. Smith, Jefferson, MD (US); Randall Johnson, Frederick, MD (US)

(73) Assignee: The United States of America as represented by the Secretary, Department of Health and Human Services, Washington, DC (US)

(*) Notice: Subject to any disclaimer, the term of this patent is extended or adjusted under 35 U.S.C. 154(b) by 464 days.

(21) Appl. No.: 12/864,218

(22) PCT Filed: Jan. 30, 2009

(86) PCT No.: PCT/US2009/032754
§ 371 (c)(1),
(2), (4) Date: Jul. 22, 2010

(87) PCT Pub. No.: WO2009/097593
PCT Pub. Date: Aug. 6, 2009

(65) Prior Publication Data
US 2010/0297660 A1  Nov. 25, 2010

Related U.S. Application Data

(60) Provisional application No. 61/024,863, filed on Jan. 30, 2008, provisional application No. 61/095,590, filed on Sep. 9, 2008.

(51) Int. Cl.
*C12Q 1/68*  (2006.01)
*C12P 19/34*  (2006.01)

(52) U.S. Cl.
CPC ........ *C12Q 1/6883* (2013.01); *C12Q 2600/156* (2013.01); *C12Q 2600/172* (2013.01)

(58) Field of Classification Search
CPC ........... C12Q 1/6883; C12Q 2600/156; C12Q 2600/172; C12Q 2600/106; C12Q 1/703; C12Q 1/6876; C12Q 2600/118; C12Q 2600/136; C12Q 1/6886; C12Q 2600/112; C12Q 2600/142; C12Q 2600/16; C12Q 2600/158; G01N 33/6893; G01N 2800/347; G01N 2800/52; G01N 33/56988; C12N 2710/24132; C12N 2710/24143; C12N 15/86; C12N 7/00; C12N 2710/24161; C12N 2710/24122; C12N 2799/026; C12N 15/1055; C12N 15/8509; C12N 2710/24121; C12N 2800/80; C12N 9/22
See application file for complete search history.

(56) References Cited

U.S. PATENT DOCUMENTS

| 5,474,796 | A  | * | 12/1995 | Brennan ........................ 427/2.13 |
| 6,905,827 | B2 |   | 6/2005  | Wohlgemuth et al. |
| 7,052,865 | B1 |   | 5/2006  | Brady et al. |
| 7,297,556 | B2 |   | 11/2007 | Tomosugi |
| 2003/0092019 | A1 | * | 5/2003 | Meyer et al. ...................... 435/6 |
| 2006/0068405 | A1 |   | 3/2006 | Diber et al. |
| 2007/0082337 | A1 |   | 4/2007 | Sorek et al. |
| 2007/0124086 | A1 |   | 5/2007 | Mendrick et al. |

FOREIGN PATENT DOCUMENTS

| WO | WO 01/73130 A1   | 10/2001 |
| WO | WO 2004/038377 A2 | 5/2004  |

OTHER PUBLICATIONS

Hirschhorn et al. (Genetics in Medicine. vol. 4, No. 2, pp. 45-61, Mar. 2002).*
Ioannidis (Nature Genetics, vol. 29, pp. 306-309, Nov. 2001).*
Freedman et al. (Am J Nephrol 2010 vol. 32 p. 66).*
Papeta et al (J. Am Sco Nephrol vol. 22 2011 p. 1991).*
RS5750250 (NCBI database SS23644927 Aug. 10, 2004).*
Amundadottir et al. (Nature Genetics 2006 vol. 38 p. 652).*
"GeneChip Human Mapping 500K Array Set," Internet Citation, [Online] 2006, XP002532775, retrieved from the Internet: URL:http://www.affymetrix.com/support/technical/datasheets/500k_datasheet.pdf, retrieved on Jun. 16, 2009, Abstract.
"Affymetrix Mapping 250K Sty2 SNP Array," GEO, May 13, 2002, XP002532776, Retrieved from the Internet: URL:http://www.ncbi.nlm.hih.gov/geo/query/acc.cgi?acc=GPL3720, retrieved on Jun. 16, 2009.
Arrondel et al., "Expression of the Nonmuscle Myosin Heavy Chain IIA in the Human Kidney and Screening for *MYH9* Mutations in Epstein and Fechtner Syndromes," *J. Am. Soc. Nephrol.* 13:65-74, 2001.
Capria et al., "Double Nucleotidic Mutation of the MYH9 Gene in a Young Patient with End-Stage Renal Disease," *Nephrol. Dial. Transplant.* 19:249-251, 2004.
Chechtkin et al.., "Sequencing by Hybridization with the Generic 6-mer Oligonucleotide Microarray: An Advanced Scheme for Data Processing," *J. Biomol. Struc. Dyn.* 18:83:101, 2000.
D'Agati, "The Spectrum of Focal Segmental Glomerulosclerosis: New Insights," *Curr. Opin. Nephrol. Hypertens.* 17:271-281, 2008.

(Continued)

*Primary Examiner* — Katherine Salmon
(74) *Attorney, Agent, or Firm* — Klarquist Sparkman, LLP

(57) ABSTRACT

Methods for determining the genetic predisposition of a human subject to developing renal disease, such as focal segmental glomerulosclerosis (FSGS) or end-stage kidney disease are provided herein. These methods include methods for detecting renal disease, or determining the risk of developing renal disease in a human subject, such as a subject of African ancestry. The methods utilize the detection of one or more haplotype blocks comprising at least two tag single nucleotide polymorphisms (SNPs) in a non-coding region of a MYH9 gene or detecting the presence of at least one tag SNP in a non-coding region of a MYH9 gene. An array for detecting a genetic predisposition to renal disease using probes complementary to the tag SNPs in the non-coding region of the MYH9 gene are also disclosed.

5 Claims, 18 Drawing Sheets

(56) References Cited

OTHER PUBLICATIONS

Dunning et al., "A Systematic Review of Genetic Polymorphisms and Breast Cancer Risk," *Cancer Epidemiol. Biomarkers Prevent.* 8:843-854, 1999.

Freedman et al., "Polymorphisms in the Non-Muscle Myosin Heavy Chain 9 Gene (*MYH9*) are Strongly Associated with End-Stage Renal Disease Historically Attributed to Hypertension in African Americans," *Kidney Int.* 75:736-745, 2009.

Ghiggeri et al., "Genetics, Clinical and Pathological Features of Glomerulonephrites Associated With Mutations of Nonmuscle Myosin IIA (Fechtner Syndrome)," *Am. J. Kidney Dis.* 41:95-104, 2003.

Heath et al., "Nonmuscle Myosin Heavy Chain IIA Mutations Define a Spectrum of Autosomal Dominant Macrothrombocytopenias: May-Hegglin Anomaly and Fechtner, Sebastian, Epstein, and Alport-Like Syndromes," *Am. J. Hum. Genet.* 69:1033-1045, 2001.

Ihalmo, "Nephrin-Associated Molecules in Human Glomerular Diseases," Academic Dissertation, University of Helsinki, Finland, 2007 (pp. 22, 58 & 65).

Kao et al., "*MYH9* is Associated with Nondiabetic End-Stage Renal Disease in African Americans," *Nature Genet.* 40:1185-1192, 2008.

Kiberd and Clase, "Cumulative Risk for Developing End-Stage Renal Disease in the US Population," *J. Am. Soc. Nephrol.* 13:1635-1644, 2002.

Kitiyakara et al., "Trends in the Epidemiology of Focal Segmental Glomerulosclerosis," *Semin. Nephrol.* 23:172-82, 2003.

Kopp and Winkler, "HIV-Associated Nephropathy in African Americans," *Kidney Int.* 63:S43-S49, 2003.

Kopp et al., "*MYH9* is a Major-Effect Risk Gene for Focal Segmental Glomerulosclerosis," *Nature Genet.* 40:1175-1184, 2008.

Moxey-Mims et al., "End-Stage Renal Disease in Two Pediatric Patients with Fechtner Syndrome," *Pediatr. Nephrol.* 13:782-786, 1999.

Pecci et al., "Position of Nonmuscle Myosin Heavy Chain IIA (NMMHC-IIA) Mutations Predicts the Natural History of *MYH9*-Related Disease," *Hum. Mutat.* 29:409-417, 2008.

Pollak, "Kidney Disease and African Ancestry," *Nature Genet.* 40:1145-1146, 2008.

Schwab et al., "Microarray Analysis of Focal Segmental Glomerulosclerosis," *Am. J. Nephrol.* 24:438-447, 2004.

Schwab, "Expression Microarray Analysis of renal Development and Human Renal Disease," Dissertation, University of Cincinnati, Ohio, 2006 (pp. 24-25, 209-210, 222, 230 & 244).

Seri et al., "Mutations in *MYH9* Result in the May-Hegglin Anomaly, and Fechtner and Sebastian Syndromes," *Nature Genet.* 26:103-105, 2000.

Seri et al., "Epstein Syndrome: Another Renal Disorder with Mutations in the Nonmuscle Myosin Heavy Chain 9 Gene," *Hum. Genet.* 110:182-186, 2002.

Seri et al., "MYH9-related Disease: May-Hegglin Anomaly, Sebastian Syndrome, Fechtner Syndrome, and Epstein Syndrome are not Distinct Entities but Represent a Variable Expression of a Single Illness," *Medicine* 82:203-215, 2003.

Winkler et al., "Genome Wide Admixture Mapping Identifies MYH9 as a Major Effect Risk Gene for Focal Segmental Glomerulosclerosis," retrieved from the internet: URL:http://www.ashg.org/2008meeting/abstracts/fulltext/f20021.htm, retrieved on Nov. 14, 2008, Abstract.

Yi et al., "Analysis of Clinical Manifestations, Mutant Gene and Encoded Protein in Two Chinese *MYH9*-Related Disease Families," *Clin. Chim. Acta* 373:49-54, 2006.

\* cited by examiner

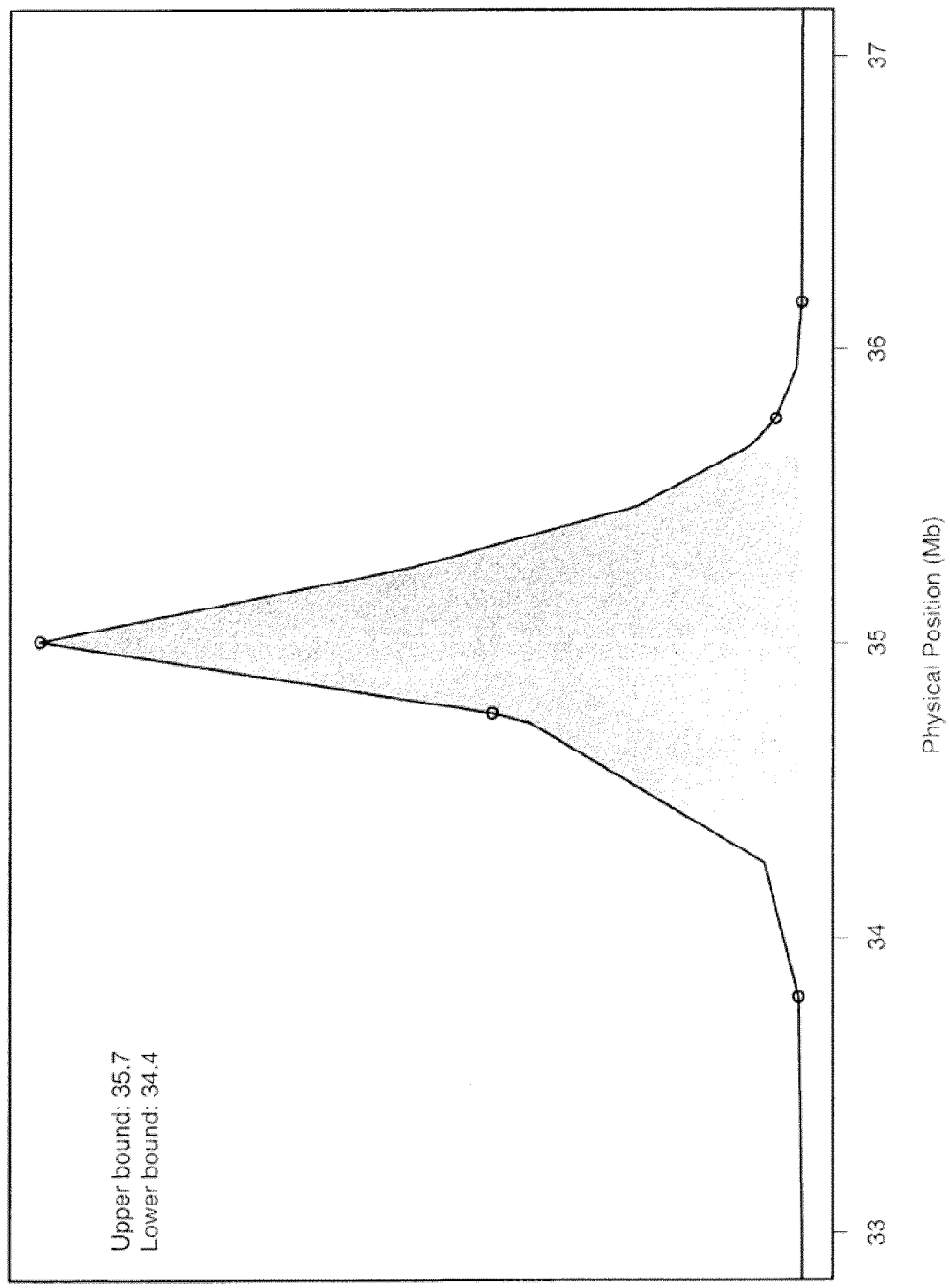

FIG. 3A
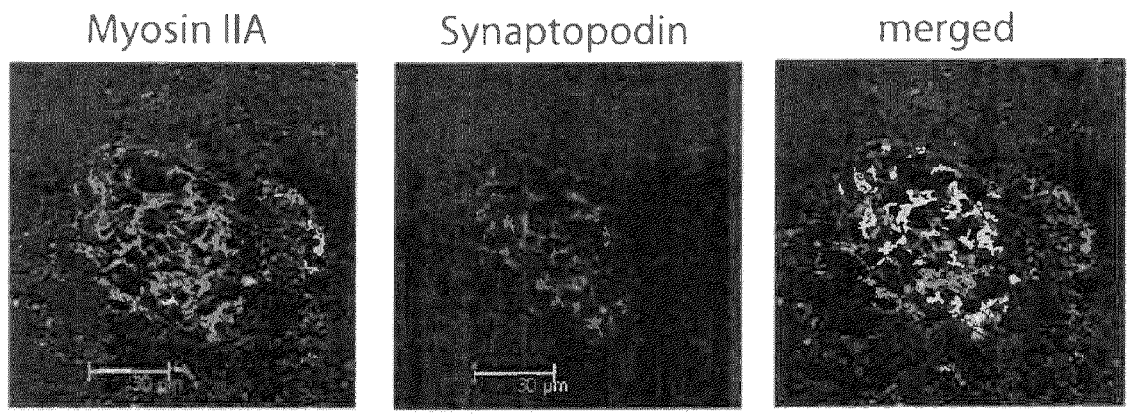
FIG. 3B
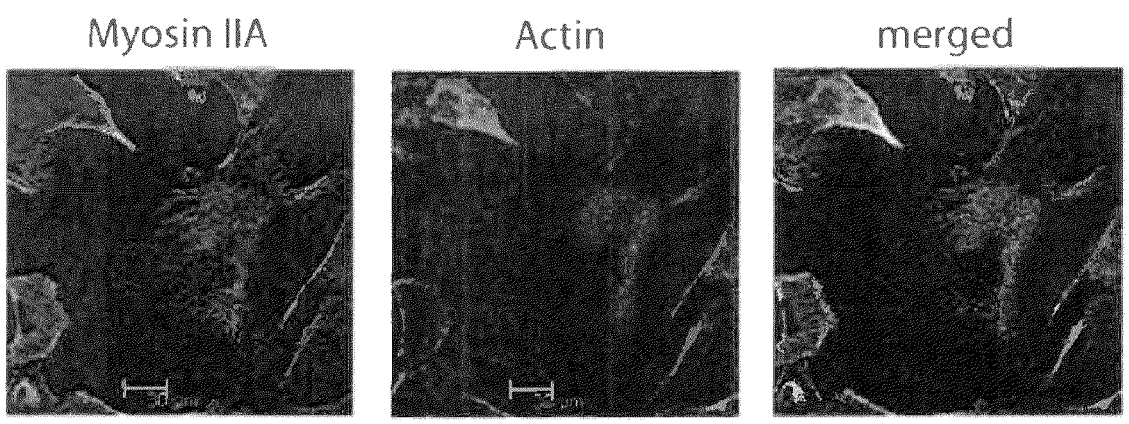
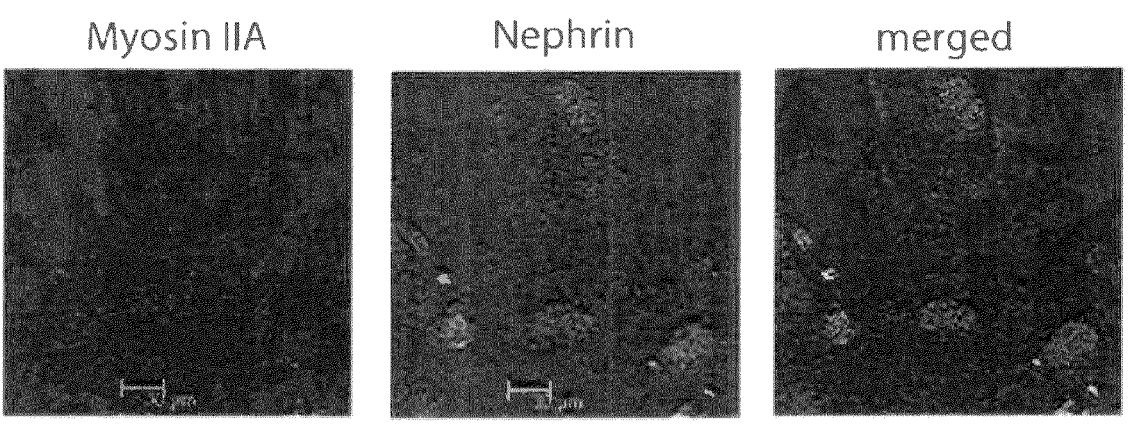

FIG. 4A

Table 1a. MYH9 allele frequencies in European-Americans (EA) and African-Americans (AA) and SNP associations with FSGS[1] for 247 African-American FSGS cases and 638 African-American controls.

| SNP | Genomic Position | Alleles Reference | Alleles Risk[2] | Risk allele frequency[3] EA | Risk allele frequency[3] AA | Risk allele, dominant model OR | (95% CI) | $P_{FET}$[4] | Risk allele, recessive model OR | (95% CI) | $P_{FET}$ |
|---|---|---|---|---|---|---|---|---|---|---|---|
| rs7078 | 35.008 | G | A | 72.9% | 85.2% | 1.8 | (0.5,10) | 0.42 | 2.5 | (1.6,3.9) | 8E-06 |
| rs12107 | 35.008 | A | G | 85.3% | 89.1% | Inf | (0.5,Inf) | 0.19 | 3.2 | (1.8,5.8) | 4E-06 |
| rs735853 | 35.009 | G | C | 51.9% | 88.3% | 4.3 | (0.6,190) | 0.20 | 8.8 | (4.1,22.7) | 5E-13 |
| rs5756129 | 35.014 | C | T | 77.9% | 79.3% | 13.2 | (2.2,540) | 0.0003 | 2.8 | (1.9,4.2) | 4E-08 |
| rs5756130 | 35.014 | T | C | 97.6% | 87.5% | Inf | (0.9,Inf) | 0.07 | 2.1 | (1.4,3.4) | 0.0005 |
| rs11549907 | 35.015 | A | G | 98.5% | 93.7% | 1.1 | (0.9,60) | 1 | 1.6 | (1.0,2.8) | 0.08 |
| rs875725 | 35.022 | C | T | 98.5% | 92.8% | 0.8 | (0.0,46) | 1 | 1.9 | (1.2,3.3) | 0.009 |
| rs2187776 | 35.025 | T | C | 3.1% | 30.1% | 1.3 | (1,18) | 0.08 | 1.3 | (0.7,2.1) | 0.37 |
| rs4821480 | 35.025 | T | G | 4.3% | 67.4% | 4.8 | (2.2,12.6) | 5E-06 | 4.8 | (3.3,7.1) | 2E-19 |
| rs2032487 | 35.025 | T | C | 4.3% | 63.7% | 5.0 | (2.3,13.1) | 2E-06 | 4.2 | (3.0,6.0) | 2E-18 |
| rs4821481 | 35.026 | T | C | 4.3% | 62.3% | 5.0 | (2.3,13.2) | 2E-06 | 4.5 | (3.2,6.5) | 1E-20 |
| rs3752462 | 35.040 | C | T | 31.0% | 72.0% | 5.3 | (1.7,27.1) | 0.001 | 3.9 | (2.7,5.7) | 4E-15 |
| rs5756152 | 35.042 | A | G | 2.6% | 26.1% | 3.4 | (2.4,4.8) | 1E-13 | 4.9 | (3.1,7.8) | 3E-13 |
| rs1557539 | 35.044 | C | A | 99.6% | 97.5% | Inf | (0.1,Inf) | 1 | 2.0 | (0.9,5.5) | 0.11 |
| rs1005570 | 35.045 | G | A | 7.9% | 41.8% | 4.4 | (2.7,7.3) | 2E-12 | 3.8 | (2.7,5.4) | 3E-15 |
| rs16996674 | 35.057 | C | T | < 0.01 | 23.5% | 2.6 | (1.9,3.7) | 1E-09 | 4.1 | (2.5,6.7) | 7E-09 |
| rs16996677 | 35.057 | G | A | < 0.01 | 25.2% | 2.8 | (2,3.9) | 1E-10 | 3.9 | (2.5,6.1) | 4E-10 |

Table 1b. MYH9 haplotype (SNPs rs3752462, rs2032487, rs4821481, rs4821480) associations with FSGS in African-Americans.

| Haplotype | Genomic Position | Haplotype Allele sequence | Haplotype Frequency EA | Haplotype Frequency AA | Dominant Genetic Model OR | (95% CI) | $P_{FET}$ | Recessive Genetic Model OR | (95% CI) | $P_{FET}$ |
|---|---|---|---|---|---|---|---|---|---|---|
| E-1 | | TCCG | 0.04 | 0.60 | 4.68 | (2.2, 11.4) | 2E-06 | 4.98 | (3.5, 7.1) | 4E-23 |
| E-2 | 35.025 to | CTTT | 0.69 | 0.20 | 0.21 | (0.1, 0.3) | 1E-13 | 0.15 | (0.02, 0.6) | 0.002 |
| E-3 | 35.040 | TTTT | 0.27 | 0.12 | 0.43 | (0.3, 0.7) | 0.0002 | 0.00 | (0.0, 0.6) | 0.003 |
| E-4 | | CTTG | < 0.01 | 0.04 | 0.76 | (0.4, 1.5) | 0.46 | NA | NA | NA |
| E-5 | | CCCG | < 0.01 | 0.03 | 0.48 | (0.2, 1.1) | 0.07 | NA | NA | NA |

[1] Idiopathic or HIV-associated FSGS.
[2] Those with odds ratio (OR) > 1 (for the most significant genetic model if models differ).
[3] Frequencies are for normal controls.
[4] FET: Fisher's exact test.
[5] Inf: OR has zero in denominator since factor is absent from controls or is always present in cases.

FIG. 4B

Table 2. MYH9 and adjacent gene SNP associations with FSGS for African-Americans and those with only local African ancestry.

| Gene | SNP | Genomic position | Association at SNP p[2] | All African-American FSGS cases (n=247) and controls (n=638) Admixture Association not explained by SNP Chi square | All African-American FSGS cases (n=247) and controls (n=638) Admixture Association not explained by SNP p[2] | locus-specific FSGS association explained by SNP genotype alone | 2x local African Ancestry (n=245)[1] OR[3] | 2x local African Ancestry (n=245)[1] P_FST[4] |
|---|---|---|---|---|---|---|---|---|
| RBM9 | rs5750175 | 34,479 | 0.39 | 57.0 | 4E-14 | 1 | 1.37 | 0.14 |
| | rs5755943 | 34,496 | 0.41 | 49.5 | 2E-12 | 1 | 0.95 | 1 |
| | rs7078 | 35,008 | 0.0009 | 40.6 | 1E-10 | 21 | 3.07 | 0.005 |
| | rs12107 | 35,008 | 0.0009 | 42.2 | 8E-11 | 21 | 3.08 | 0.03 |
| MYH9 | rs735853 | 35,009 | 8E-10 | 22.7 | 2E-06 | 62 | Inf[5] | 0.10 |
| | rs5756129 | 35,014 | 3E-06 | 42.6 | 7E-11 | 34 | 3.39 | 0.0001 |
| | rs5756130 | 35,014 | 0.002 | 55.9 | 8E-14 | 14 | 3.21 | 0.001 |
| | rs11849907 | 35,015 | 0.02 | 52.2 | 5E-13 | 9 | 1.70 | 0.18 |
| | rs875725 | 35,022 | 0.0007 | 56.1 | 7E-14 | 17 | 1.97 | 0.092 |
| | rs2187776 | 35,025 | 0.22 | 46.4 | 1E-11 | 3 | 0.99 | 1 |
| | rs4821480 | 35,025 | 4E-15 | 12.6 | 0.0004 | 83 | 3.24 | 0.003 |
| | rs2032487 | 35,025 | 1E-14 | 15.5 | 8E-05 | 79 | 2.80 | 0.0004 |
| | rs4821481 | 35,026 | 1E-15 | 13.0 | 0.0003 | 83 | 3.21 | 6E-05 |
| | rs3752462 | 35,026 | 3E-11 | 24.5 | 8E-07 | 65 | 3.17 | 1E-04 |
| | rs5756152 | 35,042 | 4E-12 | 33.1 | 9E-09 | 59 | 2.26 | 5E-05 |
| | rs1557539 | 35,044 | 0.02 | 52.3 | 5E-13 | 10 | 3.59 | 0.34 |
| | rs1005570 | 35,045 | 4E-12 | 29.5 | 6E-08 | 62 | 2.30 | 5E-05 |
| | rs16996674 | 35,057 | 4E-07 | 38.4 | 6E-10 | 40 | 1.48 | 0.05 |
| | rs16996677 | 35,062 | 2E-03 | 35.8 | 2E-09 | 47 | 1.59 | 0.02 |
| PVALB | rs736721 | 35,533 | 0.0009 | 38.5 | 5E-10 | 22 | 1.28 | 0.26 |
| | rs739031 | 35,538 | 0.0007 | 39.3 | 4E-10 | 23 | 1.32 | 0.20 |
| | rs2269513 | 35,541 | 0.41 | 41.4 | 1E-10 | 2 | 0.95 | 0.85 |
| TST | rs5756477 | 35,737 | 0.25 | 36.0 | 2E-09 | 4 | 1.06 | 0.85 |
| | rs5130598 | 35,738 | 0.12 | 33.5 | 7E-09 | 7 | 1.08 | 0.80 |
| | rs470029 | 35,740 | 0.01 | 30.1 | 4E-08 | 18 | 1.24 | 0.36 |
| TMPRSS6 | rs8135787 | 35,804 | 2E-06 | 17.2 | 3E-05 | 57 | 2.27 | 0.085 |
| | rs8135787 | 35,805 | 0.10 | 32.4 | 1E-08 | 8 | 0.99 | 1 |
| | rs2543519 | 35,810 | 0.03 | 31.0 | 3E-08 | 13 | 1.34 | 0.13 |
| | rs1421312 | 35,818 | 0.41 | 34.3 | 5E-09 | 2 | 0.88 | 0.55 |

[1] Limited to individuals predicted with greater than 95% confidence to carry two African derived chromosomal segments at the locus.
[2] Chi square and significance (P) are determined from logistic regression deviance log likelihood.
[3] Odds ratio (OR) and P are for the allele genetic model.
[4] FST: Fisher's exact test
[5] Inf: OR has zero in denominator since factor is absent from controls or is always present in cases.

FIG. 4C

Table 3. MYH9 associations in multiple groups: Idiopathic FSGS, HIV-1 associated FSGS, and hypertensive ESKD

| | African Americans | | | | | | | | | | | | European Americans | | | |
|---|---|---|---|---|---|---|---|---|---|---|---|---|---|---|---|---|
| | Idiopathic FSGS (n=587) | | | | HIV-associated FSGS (n=298) | | | | Hypertensive End Stage Kidney Disease (n=602) | | | | Idiopathic FSGS (n=41) | | | |
| | Risk Allele Dominant | | Risk Allele Recessive | | Risk Allele Dominant | | Risk Allele Recessive | | Risk Allele Dominant | | Risk Allele Recessive | | Risk Allele Dominant | | Risk Allele Recessive | |
| Variant | OR | $P_{FET}$ | OR | $P_{FET}$ | OR | $P_{FET}$ | OR | $P_{FET}$ | OR | $P_{FET}$ | OR | $P_{FET}$ | OR | $P_{FET}$ | OR | $P_{FET}$ |
| rs7078 | 1.00 | 1 | 2.12 | 0.001 | Inf | 0.36 | 6.13 | 0.0005 | NT[a] | | 1.36 | 0.20 | 0.88 | 0.85 | 0.97 | 0.91 |
| rs12107 | Inf[b] | 1 | 2.81 | 0.0002 | Inf | 1 | 10.70 | 0.002 | 0 | 0.57 | 1.18 | 0.45 | 0.53 | 0.42 | 1.24 | 0.45 |
| rs739853 | 2.55 | 0.28 | 9.79 | 2E-10 | Inf | 1 | 6.55 | 0.002 | 2.95 | 0.12 | 1.18 | 0.28 | 0.85 | 0.58 | 1.23 | 0.44 |
| rs5756129 | 11.88 | 0.001 | 2.32 | 7E-05 | Inf | 0.22 | 6.62 | 2E-05 | 1.41 | 0.38 | 1.21 | 0.28 | 1.03 | 1 | 0.68 | 0.09 |
| rs5756130 | Inf | 0.10 | 1.86 | 0.01 | Inf | 1 | 3.56 | 0.01 | 1.46 | 0.51 | 1.19 | 0.40 | 0[c] | 0 | 0.40 | 0.03 |
| rs11549903 | 0.97 | 1 | 1.14 | 0.78 | Inf | 1 | 4.98 | 0.02 | NT | 1 | | | 0.00 | 0.35 | 0.94 | 1 |
| rs3752225 | 0.99 | 1 | 1.30 | 0.28 | 0 | 1 | 4.16 | 0.01 | 0 | 1 | | | 0 | 0 | 1.26 | 1 |
| rs2187776 | 1.30 | 0.17 | 1.07 | 0.68 | 1.43 | 0.29 | 1.71 | 0.27 | 1.21 | 0.27 | 1.53 | 0.08 | 1.77 | 0.19 | 1.70 | 1 |
| rs4821480 | 4.12 | 0.0001 | 4.54 | 1E-13 | Inf | 0.006 | 5.28 | 2E-06 | 2.17 | 0.52 | 1.41 | 0.25 | 1.55 | 0.26 | 9.69 | 0.02 |
| rs4821481 | 4.30 | 7E-05 | 3.69 | 7E-12 | Inf | 0.006 | 6.67 | 8E-08 | NT | | 1.40 | 0.05 | 1.55 | 0.26 | 9.69 | 0.02 |
| rs3752462 | 4.32 | 7E-05 | 4.09 | 1E-13 | Inf | 0.007 | 6.55 | 5E-08 | 1.35 | 0.81 | 1.69 | 0.003 | 1.56 | 0.26 | 9.73 | 0.02 |
| rs5756152 | 4.77 | 0.005 | 3.49 | 4E-10 | Inf | 0.13 | 5.90 | 3E-06 | 1.90 | 0.06 | 1.39 | 0.06 | 1.08 | 0.82 | 2.42 | 0.01 |
| rs5756168 | 2.98 | 1E-08 | 5.62 | 2E-10 | 5.53 | 1E-06 | 4.22 | 4E-04 | 1.70 | 0.002 | 2.12 | 0.02 | 1.73 | 0.24 | 0.00 | 1 |
| rs1557539 | Inf | 1 | 1.42 | 0.65 | Inf | 1 | 4.39 | 0.22 | Inf | 1 | 0.64 | 0.35 | 0 | 0 | 0.36 | 0.39 |
| rs1005570 | 4.50 | 4E-10 | 3.48 | 7E-10 | 4.94 | 0.0007 | 5.20 | 5E-07 | 0.92 | 0.71 | 1.36 | 0.15 | 0.92 | 0.88 | 0.00 | 1 |
| rs16996674 | 2.57 | 5E-07 | 4.59 | 1E-07 | 3.08 | 0.0007 | 3.30 | 0.01 | 1.09 | 0.62 | 1.41 | 0.37 | Inf | 0.12 | 0 | 0 |
| rs16996677 | 2.69 | 1E-07 | 4.08 | 7E-08 | 3.41 | 0.0007 | 3.47 | 0.005 | 1.08 | 0.67 | 1.65 | 0.13 | Inf | 0.12 | 0 | 0 |
| Haplotype E-1 | 3.99 | 7E-05 | 4.65 | 9E-16 | Inf | 0.004 | 5.92 | 7E-08 | 1.75 | 0.03 | 1.74 | 0.003 | 1.63 | 0.18 | 7.66 | 0.05 |
| Haplotype E-2 | 0.24 | 1E-09 | 0.16 | 0.003 | 0.12 | 3E-05 | 0 | 0.36 | 0.78 | 0.22 | 0.68 | 0.36 | 0.39 | 0.008 | 0.95 | 0.81 |
| Haplotype E-3 | 0.45 | 0.003 | 0.00 | 0.02 | 0.42 | 0.06 | 0 | 0.36 | 0.66 | 0.06 | 1.43 | 1.00 | 0.99 | 1 | 1.67 | 0.21 |
| Haplotype E-4 | 0.88 | 0.87 | 0 | 0 | 0.28 | 0.21 | 0 | 0 | 0.42 | 0.01 | 0 | 0 | 0 | 0 | 0 | 0 |
| Haplotype E-5 | 0.42 | 0.10 | 0 | 0 | 0.75 | 1 | 0 | 0 | 1.03 | 1 | 0 | 0 | 0 | 0 | 0 | 0 |

[FET: Fisher exact test.
[b] Inf: OR has zero in denominator since factor is absent from controls or is always present in cases.
[a] NT: not genotyped for SNP.
[c] rare genotype or haplotype absent from both cases and controls.

Supplemental Table 1b. MYH9 Haplotype associations with FSGS and End Stage Kidney Disease (ESKD) for longest robustly inferred haplotypes[1]

| | Frequency | | Idiopathic and HIV-associated FSGS (N = 832) | | African-Americans Idiopathic FSGS (N = 540) | | African-Americans HIV-associated FSGS (N = 282) | | African-Americans Type 2 Diabetes-associated ESKD (N = 476) | | African-Americans Hypertensive-associated ESKD (N = 586) | | European Americans Idiopathic FSGS (N = 354) | |
|---|---|---|---|---|---|---|---|---|---|---|---|---|---|---|
| Haplotypes for SNPs rs735853 to rs4821481 | African-American | European-American[2] | OR[3] | $P_{ST}$ | OR | $P_{FT}$ | OR | $P_{ST}$ | OR | $P_{ST}$ | OR | P | OR | P |
| M1-1 | CTCTCGCC | 0.32 | < 0.01 | 2.50 | 2E-15 | 3.07 | 8E-07 | 2.36 | 3E-10 | 1.07 | 0.70 | 1.49 | 0.005 | d | 0 |
| M1-2 | CTCTCGCC | 0.30 | 0.034 | 1.24 | 0.06 | 1.78 | 0.23 | 1.20 | 0.18 | 1.24 | 0.15 | 1.17 | 0.25 | 1.98 | 0.09 |
| M1-3 | CCCTTTT | 0.07 | 0.241 | 0.82 | 0.05 | 0.52 | 0.28 | 0.64 | 0.12 | 0.78 | 0.36 | 0.75 | 0.26 | 0.66 | 0.03 |
| M1-4 | GTCTCGCC | 0.07 | 0.416 | 0.17 | 5E-09 | 0.21 | 0.01 | 0.16 | 2E-07 | 0.72 | 0.21 | 0.74 | 0.20 | 0.95 | 0.81 |
| M1-5 | CTCTCGCC | 0.06 | < 0.01 | 0.89 | 0.15 | 0.73 | 0.08 | 0.88 | 0.58 | 0.72 | 0.30 | 0.72 | 0.26 | 0 | 0 |
| M1-6 | CCCTTTT | 0.06 | 0.18 | 0.22 | 2E-06 | 0 | 0.0012 | 0.28 | 0.0002 | 0.82 | 0.50 | 0.70 | 0.18 | 1.07 | 0.77 |
| M1-7 | CCCTTTT | 0.05 | 0.02 | 0.26 | 2E-05 | 0.26 | 0.06 | 0.26 | 0.0002 | 1.47 | 0.19 | 0.87 | 0.67 | 2.60 | 0.03 |
| M1-8 | CCTTGTT | 0.04 | < 0.01 | 0.93 | 0.66 | 0.25 | 0.22 | 0.97 | 1 | 0.55 | 0.09 | 0.47 | 0.02 | 0 | 0 |

Haplotypes for SNPs rs3752462 to rs1557539

| M2-1 | TGG | 0.45 | 0.31 | 0.79 | 0.04 | 0.92 | 0.39 | 0.78 | 0.02 | 0.94 | 0.64 | 0.86 | 0.23 | 1.17 | 0.39 |
| M2-2 | TAG | 0.30 | 0.02 | 3.00 | 3E-21 | 3.66 | 2E-08 | 2.80 | 5E-14 | 1.21 | 0.24 | 1.73 | 0.0002 | 1.50 | 0.45 |
| M2-3 | CCG | 0.22 | 0.65 | 0.28 | 3E-16 | 0.15 | 3E-07 | 0.31 | 8E-11 | 0.87 | 0.40 | 0.67 | 0.008 | 0.79 | 0.16 |
| M2-4 | TAC | 0.02 | < 0.01 | 0.36 | 0.07 | 0 | 0.09 | 0.73 | 0.78 | 1.39 | 0.63 | 1.03 | 1 | 0 | 0 |

Haplotypes for SNPs rs1557539 to rs16996672

| M3-1 | GGCG | 0.48 | 0.31 | 0.37 | 9E-19 | 0.32 | 1E-06 | 0.37 | 5E-14 | 1.24 | 0.11 | 0.83 | 0.15 | 1.18 | 0.66 |
| M3-2 | GATA | 0.29 | < 0.01 | 2.37 | 2E-13 | 2.49 | 7E-05 | 2.39 | 3E-10 | 0.85 | 0.31 | 1.26 | 0.10 | 0 | 0 |
| M3-3 | GACG | 0.19 | 0.02 | 1.41 | 0.01 | 1.54 | 0.12 | 1.40 | 0.05 | 0.74 | 0.10 | 0.91 | 0.52 | 0.74 | 0.36 |
| M3-4 | GACA | 0.03 | < 0.01 | 1.72 | 0.09 | 1.72 | 0.24 | 1.48 | 0.27 | 1.28 | 0.67 | 1.48 | 0.45 | 0 | 0 |
| M3-5 | CGCG | 0.02 | < 0.01 | 0.30 | 0.06 | 0 | 0.22 | 0.45 | 0.29 | 1.92 | 0.24 | 1.41 | 0.63 | 0 | 0 |

[1] Longest haplotypes that could be inferred with uncertainty < 2% (uncertainty measured as entropy); < 2% of haplotypes unique to European-Americans with frequency > 1%.
[2] Analysis was not done for haplotypes with frequency < 1%. There were no haplotypes unique to European-Americans with frequency > 1%.
[3] OR and P-val (FET: Fisher exact test) are for an allele model
[4] Haplotype frequency < 1% in European-Americans

FIG. 5A

| SNP | position | recOR | min P | significance group |
|---|---|---|---|---|
| start | 35113797 | Intron | #1 | |
| rs2272827 | 35111514 | 2.0 | 7.6E-03 | low |
| rs9610498 | 35107685 | 3.3 | 2.8E-07 | high |
| rs5756168 | 35104758 | 3.9 | 0.035 | low |
| rs1883273 | 35099631 | 2.2 | 9.0E-07 | high |
| rs136213 | 35089761 | 2.5 | 3.0E-07 | high |
| rs136206 | 35085444 | 2.2 | 1.2E-06 | high |
| rs6000254 | 35077529 | 8.8 | 8.1E-03 | low |
| rs6000251 | 35077352 | 4.7 | 5.1E-03 | low |
| end | 35075247 | | | |
| start | 35074894 | Intron | #2 | |
| rs739096 | 35071686 | 6.3 | 2.6E-12 | high |
| end | 35067518 | | | |
| start | 35067360 | Intron | #3 | |
| rs8135022 | 35062938 | 5.4 | 9.9E-03 | low |
| rs5995283 | 35060023 | 4.8 | 0.015 | low |
| rs8143119 | 35057497 | 3.6 | 5.6E-14 | high |
| rs16996677 | 35057229 | 3.9 | 3.6E-10 | high |
| rs16996674 | 35056598 | 4.1 | 4.0E-09 | high |
| rs5756157 | 35053643 | 3.0 | 2.1E-12 | high |
| end | 35053480 | | | |
| start | 35053451 | Intron | #4 | |
| end | 35052653 | | | |
| start | 35052558 | Intron | #5 | |
| rs12159211 | 35049109 | 4.0 | 2.9E-03 | low |
| rs2071731 | 35048804 | 1.7 | 9.2E-03 | low |
| end | 35048513 | | | |
| start | 35048419 | Intron | #6 | |
| end | 35047813 | | | |
| start | 35047748 | Intron | #7 | |
| rs8138583 | 35047578 | 4.2 | 0.010 | low |

FIG. 5B

| | | | | |
|---|---|---|---|---|
| end | 35046888 | | | |
| start | 35046788 | Intron | #8 | |
| end | 35046355 | | | |
| start | 35046210 | Intron | #9 | |
| end | 35045627 | | | |
| start | 35045530 | Intron | #10 | |
| rs1005570 | 35045220 | 3.8 | 2.6E-15 | high |
| rs8141189 | 35044656 | 3.8 | 3.2E-09 | high |
| rs2239784 | 35044581 | 3.2 | 3.1E-13 | high |
| end | 35044317 | | | |
| start | 35044197 | Intron | #11 | |
| rs1557538 | 35042909 | 2.2 | 1.1E-06 | high |
| rs1557536 | 35042756 | 2.2 | 7.3E-07 | high |
| end | 35042661 | | | |
| start | 35042507 | Intron | #12 | |
| rs5756152 | 35042418 | 4.9 | 3.4E-13 | high |
| rs4821484 | 35040465 | 3.9 | 2.2E-14 | high |
| end | 35040310 | | | |
| start | 35040135 | Intron | #13 | |
| rs3752462 | 35040129 | 3.9 | 3.9E-15 | high |
| rs5750250 | 35038429 | 5.6 | 1.5E-26 | high |
| rs2157257 | 35038284 | 3.6 | 1.4E-12 | high |
| end | 35038214 | | | |
| start | 35038039 | Intron | #14 | |
| rs2413396 | 35038030 | 5.7 | 3.4E-27 | high |
| rs2413396 | 35038030 | 4.8 | 1.6E-21 | high |
| rs2157256 | 35037607 | 4.5 | 1.1E-19 | high |
| rs1557529 | 35035475 | 4.1 | 5.1E-14 | high |
| end | 35035388 | | | |
| start | 35035272 | Intron | #15 | |
| rs2239783 | 35035074 | 2.7 | 9.4E-06 | high |
| rs5750248 | 35032838 | 5.1 | 4.1E-24 | high |

FIG. 5C

| | | | | | | |
|---|---|---|---|---|---|---|
| end | 35032600 | | | | | |
| start | 35032405 | Intron | #16 | | | |
| rs1009150 | 35032246 | 3.3 | 2.3E-12 | high | | |
| rs8137674 | 35032048 | 3.4 | 0.015 | low | | |
| end | 35032044 | | | | | |
| start | 35031921 | Intron | #17 | | | |
| end | 35031095 | | | | | |
| start | 35031024 | Intron | #18 | | | |
| rs17806513 | 35030332 | 1.8 | 0.011 | low | | |
| end | 35030148 | | | | | |
| rs9619601 | 35030121 | 3.5 | 4.4E-03 | low | exon 19 | synonymous |
| start | 35029986 | Intron | #19 | | | |
| end | 35028669 | | | | | |
| start | 35028559 | Intron | #20 | | | |
| end | 35027658 | | | | | |
| start | 35027525 | Intron | #21 | | | |
| end | 35027050 | | | | | |
| start | 35026842 | Intron | #22 | | | |
| end | 35026257 | | | | | |
| start | 35026118 | Intron | #23 | | | |
| rs4821481 | 35025888 | 4.5 | 1.3E-20 | high | | |
| rs2032487 | 35025374 | 4.2 | 1.0E-18 | high | | |
| rs4821480 | 35025193 | 4.9 | 4.0E-20 | high | | |
| end | 35025035 | | | | | |
| start | 35024910 | Intron | #24 | | | |
| rs739101 | 35024279 | 3.5 | 4.9E-12 | high | | |
| rs5756133 | 35023926 | 3.7 | 1.7E-09 | high | | |
| rs9622373 | 35023618 | 3.9 | 1.6E-04 | low | | |
| end | 35023007 | | | | | |
| start | 35022834 | Intron | #25 | | | |
| rs16996648 | 35022698 | 4.2 | 5.5E-11 | high | | |
| end | 35021710 | | | | | |

FIG. 5D

| | | | | | | | |
|---|---|---|---|---|---|---|---|
| rs875725 | 35021637 | 1.9 | 8.6E-03 | low | | exon 26 | synonymous |
| start | 35021496 | Intron | #26 | | | | |
| end | 35021069 | | | | | | |
| start | 35020923 | Intron | #27 | | | | |
| end | 35020291 | | | | | | |
| start | 35020083 | Intron | #28 | | | | |
| end | 35019856 | | | | | | |
| start | 35019750 | Intron | #29 | | | | |
| end | 35019474 | | | | | | |
| start | 35019320 | Intron | #30 | | | | |
| end | 35018227 | | | | | | |
| start | 35017977 | Intron | #31 | | | | |
| end | 35015290 | | | | | | |
| start | 35015076 | Intron | | | | | |
| end | 35014932 | | | | | | |
| start | 35014718 | Intron | #33 | | | | |
| rs11912763 | 35014668 | 7.9 | 3.3E-15 | high | | | |
| end | 35014406 | | | | | | |
| rs2269529 | 35014300 | 4.7 | 2.1E-06 | high | | exon 34 | Isoleucine to Valine |
| rs5756130 | 35014277 | 2.1 | 5.1E-04 | low | | | synonymous |
| start | 35014243 | Intron | #34 | | | | |
| rs5756129 | 35014038 | 2.8 | 4.0E-08 | high | | | |
| end | 35012839 | | | | | | |
| start | 35012709 | Intron | #35 | | | | |
| end | 35011946 | | | | | | |
| start | 35011856 | Intron | #36 | | | | |
| end | 35011774 | | | | | | |
| start | 35011649 | Intron | #37 | | | | |
| end | 35011322 | | | | | | |
| start | 35011112 | Intron | #38 | | | | |
| rs2071733 | 35010771 | 4.3 | 1.7E-08 | high | | | |
| rs2071732 | 35010660 | 3.7 | 6.7E-03 | low | | | |

FIG. 5E

| | | | | | | |
|---|---|---|---|---|---|---|
| end | 35010504 | | | | | |
| start | 35010394 | Intron | #39 | | | |
| end | 35010258 | | | | | |
| start | 35010084 | Intron | #40 | | | |
| rs735853 | 35009161 | 8.8 | 5.5E-13 | high | | |
| rs735854 | 35009004 | 4.8 | 2.0E-15 | high | | |
| end | 35008778 | | | | | |
| rs12107 | 35007928 | 3.2 | 3.7E-06 | high | exon 41 | 3'UTR |
| rs7078 | 35007860 | 2.5 | 5.2E-06 | high | | 3'UTR |
| rs136196 | 35005096 | 3.7 | 3.3E-13 | high | | 3'UTR |

FIG. 6A

| SNP | risk | prot | (significance) | flanking sequence | position | location |
|---|---|---|---|---|---|---|
| rs5750250 | G | A | 1.5E-26 | CTGACACCTTTACCCAAGGATCCATCG[A/G]GGGTGGTTTCTCAGCATTAGTGAAA | 35038429 | intron 13 |
| rs5750248 | T | C | 4.1E-24 | TCTCTTGGGGAGCCATGCATCTGCCA[C/T]GGGCACTCACCTTGCTGTCTGACCTA | 35032838 | intron 15 |
| rs2413396 | C | T | 3.4E-27 | AGATCTGGCCAGCACCTCCCGGTGAG[C/T]GCTCCTCACCTTGCCGGCATAGTGG | 35038030 | intron 14 |
| rs11912763 | A | G | 3.3E-15 | TGGAAGGAGAAGAACAGAAGGCTGGGT[A/G]AAGCCAAGGGCAGCGTTGGGACCCA | 35014668 | intron 33 |
| rs4821480 | G | T | 4.0E-20 | ATTTTCCTAGATCAAAGGATAATTT[G/T]AAAGGTCACGAGCTCCCCTGAAACA | 35025193 | intron 23 |
| rs4821481 | C | T | 1.3E-20 | CTCACGGCTGGCAAAGAGCTTGTTAATCCAC[A/G]TAATCCTGTATGGTGGGTCATT | 35025888 | intron 23 |
| rs2157256 | A | G | 1.1E-19 | GGGCCTCAAGAGCTGTTAATCCAC[A/G]TAATCCTGTATGGTGGTCATT | 35037607 | intron 14 |
| rs1005570 | A | G | 2.6E-15 | TAATTCAAGATCTGACATAGTCAC[A/G]GGCAAGGCTCCCATTAAGGAGGAGC | 35045220 | intron 10 |
| rs2032487 | C | T | 1.0E-18 | AGAGGCTGCCACAGGCGCTCACCTG[C/T]GCACCAGGCCACCTTCTCCGTGCC | 35025374 | intron 23 |
| rs5756152 | A | G | 3.4E-13 | AGGPAGATGGCCAACTCGATCGATG[A/G]GGACCATGAGAAGCAGGGTTCTTAA | 35042418 | intron 12 |
| rs1557529 | A | G | 5.1E-14 | CTCGGAGCACAGCTAACCCATGC[A/G]TGGAAAAGTCAGAAACGTGAAGAC | 35035475 | intron 14 |
| rs2239784 | T | C | 3.1E-13 | GGCAGGTGTACCTCCCCTGAAGAGTC[C/T]GGGGCAGAAGAAGGGTCCTGGC | 35044581 | intron 10 |
| rs16996648 | C | T | 5.5E-11 | CCCTGAGTGCAAGAACTGTTTTGC[C/T]ATGAAATAAATGGCTCTTTAAGAAC | 35022698 | intron 25 |
| rs735854 | T | C | 2.0E-15 | GCAAAATGTTTAGGTGTCGGACATCT[C/T]CACAGAAGAACAACAGTAGCACAAAACA | 35009004 | intron 40 |
| rs16996677 | A | G | 3.6E-10 | GGATGGAAGGAAATGGTGTTCCTGTC[A/G]TACAGGGTGTGAGGCAGATGCCAG | 35057229 | intron 3 |
| rs3752462 | T | C | 3.9E-15 | CAGGTGTGAAGGTCAAAGACAAGCCTGG[C/T]ACTCACTGGCTTCTCAATGAGGTCG | 35040129 | intron 13 |
| rs4821484 | C | A | 2.2E-14 | TAGAGCCCGATGCTCCTGGCCTTCC[A/C]TTATCCCAGCAGTGGGCAACA | 35040465 | intron 12 |
| rs8143119 | G | T | 5.6E-14 | CAGGTCAGCAGGCTGGGCCAGAGG[G/T]AGGAAGGGGAACCTGACGGCAGGTA | 35057497 | intron 3 |
| rs16996674 | T | C | 4.0E-09 | GCAACCAGTGGGCTCTTTGGCCTACT[C/T]AGTTTACTCTGCAGCCCACCTCG | 35056598 | intron 3 |
| rs5756157 | T | G | 2.1E-12 | CTCACACCTGGCTAGGAGGAGCATCT[G/T]CGGGGAGAAGTGCATTGGGCAG.CT | 35053643 | intron 3 |
| rs1361196 | A | G | 3.3E-13 | ACTTAGCTGTGTGGAAAACTATATG[A/G]GGTTCTTTGAAAACTTAAACATAG | 35005096 | exon 41 |
| rs2157257 | A | G | 1.4E-12 | GGGCACCCACCCCTTGTTGACAAGCCAA[A/G]CCCGGACATCGAGATCCCCTGAAT | 35038284 | intron 13 |
| rs3735853 | C | G | 5.5E-13 | ACAGGTGGCCTGTTCACAGAAGGCAGT[A/C]AAAGACAAGGCACCCTCTTCTACCA | 35009161 | intron 40 |
| rs5739096 | G | C | 2.6E-12 | TCCTTAGGGACAGGGGGCAAGGGCGTGGG[A/G]TCCTCAGATGACAGGCCAGTGTGC | 35071686 | intron 2 |
| rs5739101 | G | A | 4.9E-12 | ACTCCTCTCAAGGGGACAGGGCTGGAATGTAGGG[C/T]GTATCTCCTGAGTGTAAGAGCAGGGCC | 35024279 | intron 24 |
| rs1009150 | C | T | 2.3E-12 | AGAGGAAGTGCAGGCTGGAAGTAGG[C/T]CCCTCAGAGTGTAAAAGCAGGTCCCT | 35032246 | intron 16 |
| rs8141189 | A | G | 3.2E-09 | GTTCCTCTGTCCACTCAGCCGCAG[A/T]CCCTCAGAGTGTAAAAGCAGGAA | 35044656 | intron 10 |
| rs20711733 | G | C | 1.7E-08 | AACTGGAAAAGAGGTCTGGGCGGCCA[C/G]TGTAAACCCATTCCCTCCAAGGAA | 35010771 | intron 38 |
| rs5756133 | T | A | 1.7E-09 | CATATGTGTCTCTGACAGCTCGGTCC[A/T]CTATGTTAGCCCTATTAGTGTCAA | 35023926 | intron 24 |
| rs5756129 | C | G | 4.0E-08 | TTTATGTACCCAGTCATACACCGTT[C/T]GCAAGTTGCTGTGGACTATCATG | 35014038 | intron 34 |
| rs136206 | A | T | 1.2E-06 | GAGCCAAGTTGAAACACAGAGGGCT[A/G]AAGGGTTATAGCCAACTAATTTGTTA | 35085444 | intron 1 |
| rs136213 | G | C | 3.0E-07 | GAGGGGCAGATGATCCCCTTGAACTG[A/G]GCCCCAGGTTGCTGAAGCGGGTGACAG | 35089761 | intron 1 |
| rs9610498 | G | A | 2.8E-07 | ACGAAGCACGATTTGAACATCACTTTGC[A/G]TCTGGTCTGTTTTTTCACTTAACATA | 35107685 | intron 11 |
| rs1557538 | A | G | 1.1E-06 | aaacTTAGATCTTTGAAATAAAATG[A/G]GACACACTAAGGATTTACAGAAA | 35042909 | intron 11 |
| rs1557536 | C | G | 7.3E-07 | AGTAAATTTCACTTTAGAGTCCTCCC[C/G]CTAGAGGAAGAGCCCTAAGTATGTG | 35042756 | intron 11 |
| rs1883273 | G | A | 9.0E-07 | GTGAAGTGGCATGTTCCTAGGTCTAC[A/G]CTGCGAGCCCTCCAGGTCCTTCAGGTCC | 35099631 | intron 1 |
| rs22669529 | T | C | 2.1E-06 | GTCCCGGTTCTGTTGGCCAGGAGGACCCGGCCA[C/T]GGTGTGTGCGCCTGCAAGGGCAGGTCC | 35014300 | exon 34 |
| rs2239783 | C | T | 9.4E-06 | GCGGCTCCGCCCAGGAGGACCCGGCCA[C/T]GGTGTGTGCGCAAGGGCAGGTCC | 35035074 | intron 15 |
| rs12107 | C | T | 3.7E-06 | GCCTGCCTCTGCCAGGTCCAAGCTGT[C/T]GGGGTCCAAGCTGGAAGGCCAGCAG | 35007928 | exon 41 |

FIG. 6B

| SNP | risk allele | protective | significance | flanking sequence | position | location |
|---|---|---|---|---|---|---|
| rs7078 | T | C | 5.2E-06 | CCCAACACTCTTGGGGACCAAATATA[C/T]TTAATGGTTAAGGGACTTGTCCCAA | 35007860 | exon 41 |

(lower significant SNPs)

| SNP | risk allele | protective | significance | flanking sequence | position | location |
|---|---|---|---|---|---|---|
| rs9622373 | C | T | 1.6E-04 | CCATCACGTGATCTTGAGATGTAGCC[C/T]GTGAAGTTTCGCTGGAATAGATGTG | 35023618 | intron 24 |
| rs5756130 | C | T | 5.1E-04 | TTCCGCAGCTGTTTGATGGCTTCGTC[C/T]CGGTTCTTGTTGGCCGAGTCGATGT | 35014277 | exon 34 |
| rs6000251 | A | C | 5.1E-03 | CCACTCTGCAAGGACCACCCTGAGAG[A/C]AGGCCGGCTCAGAATGAGTCAGAAG | 35077352 | intron 1 |
| rs2071731 | G | A | 9.2E-03 | TCAGCTCTAGGAACCTGGCCCTGGAC[A/G]ACCCATGTGAAAGCAGCACTTAAAC | 35048804 | intron 5 |
| rs12159211 | G | A | 2.9E-03 | CCACTTTGGGGCTCCAGGCTGTTTACT[A/G]AGAATGTCAATAAATCCTACTGTGA | 35049109 | intron 5 |
| rs9619601 | A | G | 4.4E-03 | ACTTTGCTCTGGCCAATGCGGTACAG[A/G]TTGCTGTCGAGCTCGAGGGCTTTTA | 35030121 | exon 19 |
| rs2071732 | C | T | 6.7E-03 | GACACCTATGTGTACCGGCGTTCTTA[C/T]GACGGGCACTGCAAATAGCCCATT | 35010660 | intron 38 |
| rs2272827 | G | A | 7.6E-03 | TGATTAACATGGCTCCTTCATCCTAC[A/G]AGAGAGAAGTTGTCCCATCTCCAAC | 35111514 | intron 1 |
| rs6000254 | G | A | 8.1E-03 | CACTTCACCCTGGCACTCCAGTTCTT[A/G]CAAATCAAGGTTTCTCCCTGCCAG | 35077529 | intron 1 |
| rs875725 | T | C | 8.6E-03 | CGCTCAGACTCCAGGTCTTCTGTCAGC[C/T]CAGAGATGCTTCAGACTCCAGCTCCC | 35021637 | exon 26 |
| rs8135022 | G | C | 9.9E-03 | CATTCTGGCACCTTCTGTCCGTACC[G/T]CCATCGGCCTAATCCAAGGACTACA | 35062938 | intron 3 |
| rs8138583 | T | C | 0.010 | CTGTAAATAAGGAAAGCCTAAAGCTC[C/T]GTGTTGGGTTTGCACTAGCGATCC | 35047578 | intron 7 |
| rs17806513 | G | A | 0.011 | TGTTCCCTATCTCCCGTCACCGAACA[A/G]CAGGCTGTGCACACAGTAGGTGTTG | 35030332 | intron 18 |
| rs5756168 | C | T | 0.035 | GACGAAGGGAGTAGAAGAATAGACTC[C/T]TAAGGAAGAATTAAAGGAGCTCAGT | 35104758 | intron 1 |
| rs8137674 | A | G | 0.015 | GATGCGGGTCCAGCTTGCCGGCCTGG[A/G]GAAGAAAAACACATGCATGCGGTCTC | 35032048 | intron 16 |
| rs5995283 | T | C | 0.015 | TCAGGTTCTAAGAGGCCACTTCCTTT[C/T]TATCTCCCGCTCAGTGGGCCCAGAG | 35060023 | intron 3 |

FIG. 7

| SNP | Position | P (recessive) | Location |
|---|---|---|---|
| rs3752462 | 35040129 | 0.01 | intron 13 |
| rs6000259 | 35094192 | 0.02 | intron 1 |
| rs4821481 | 35025888 | 0.02 | intron 23 |
| rs4821480 | 35025193 | 0.02 | intron 23 |
| rs2032487 | 35025374 | 0.02 | intron 23 |
| rs2157257 | 35038284 | 0.02 | intron 13 |
| rs6000268 | 35111626 | 0.02 | intron 1 |
| rs2413396 | 35038030 | 0.02 | intron 14 |
| rs5756130 | 35014277 | 0.03 | exon 34 |
| rs8143119 | 35057497 | 0.03 | intron 3 |
| rs4821484 | 35040465 | 0.03 | intron 12 |
| rs2157256 | 35037607 | 0.03 | intron 14 |
| rs2239784 | 35044581 | 0.04 | intron 10 |

SEQUENCE LISTING

<160> NUMBER OF SEQ ID NOS: 90

<210> SEQ ID NO 1
<211> LENGTH: 52
<212> TYPE: DNA
<213> ORGANISM: Homo sapiens

<400> SEQUENCE: 1
attttcctag atcaaaggat aattttkaaa ggtcacgagc tcccctgaaa ca                52

<210> SEQ ID NO 2
<211> LENGTH: 52
<212> TYPE: DNA
<213> ORGANISM: Homo sapiens

<400> SEQUENCE: 2
ctcacggctg gcaaagaaga gctttcyaga ggggaaagga caaacccttc cc                52

<210> SEQ ID NO 3
<211> LENGTH: 52
<212> TYPE: DNA
<213> ORGANISM: Homo sapiens

<400> SEQUENCE: 3
taatttcaag atctcgacat agtcacrggc aaggctccca ttaaggagga gc                52

<210> SEQ ID NO 4
<211> LENGTH: 52
<212> TYPE: DNA
<213> ORGANISM: Homo sapiens

<400> SEQUENCE: 4
agaggctgcc acacggcgct cacctgygcc accaggccac cttctccgtg cc                52

<210> SEQ ID NO 5
<211> LENGTH: 52
<212> TYPE: DNA
<213> ORGANISM: Homo sapiens

<400> SEQUENCE: 5
aggagatggc caactcagat cgatgcrgga ccatgagaag cagggttctt aa                52

<210> SEQ ID NO 6
<211> LENGTH: 52
<212> TYPE: DNA
<213> ORGANISM: Homo sapiens

<400> SEQUENCE: 6
ggatggaagg aaatggtgtt cctgtcrtac acggtgtgag gcagatgccc ag                52

<210> SEQ ID NO 7
<211> LENGTH: 52
<212> TYPE: DNA
<213> ORGANISM: Homo sapiens

<400> SEQUENCE: 7
caggtgtgag gtcaaagcaa gcctggyact cactggcttc tcaatgaggt cg                52

<210> SEQ ID NO 8
<211> LENGTH: 52
<212> TYPE: DNA
<213> ORGANISM: Homo sapiens

<400> SEQUENCE: 8
gcaaccagtg ggctctttgg cctactyagt ttactctgca gcccacctcc cc                52

<210> SEQ ID NO 9
<211> LENGTH: 52
<212> TYPE: DNA
<213> ORGANISM: Homo sapiens

-continued

<400> SEQUENCE: 9
acaggtgtgc tgttcacac agagtasaaa gacaggcacc ctctttctac ca      52

<210> SEQ ID NO 10
<211> LENGTH: 52
<212> TYPE: DNA
<213> ORGANISM: Homo sapiens

<400> SEQUENCE: 10
tttatgtacc cagtcataca ccgtttygca agtttgctgt tggactatca tg      52

<210> SEQ ID NO 11
<211> LENGTH: 52
<212> TYPE: DNA
<213> ORGANISM: Homo sapiens

<400> SEQUENCE: 11
gcctgcctct gccacagcaa ggctgtyggg gtcaagctgg aaaggccagc ag      52

<210> SEQ ID NO 12
<211> LENGTH: 52
<212> TYPE: DNA
<213> ORGANISM: Homo sapiens

<400> SEQUENCE: 12
cccaacactc ttggggacca aatataytta atggttaagg gacttgtccc aa      52

<210> SEQ ID NO 13
<211> LENGTH: 52
<212> TYPE: DNA
<213> ORGANISM: Homo sapiens

<400> SEQUENCE: 13
ttccgcagct gtttgatggc ttcgtcycgg ttcttgttgg ccgagtcgat gt      52

<210> SEQ ID NO 14
<211> LENGTH: 52
<212> TYPE: DNA
<213> ORGANISM: Homo sapiens

<400> SEQUENCE: 14
actttgctct ggccaatgcg gtacagrttg ctgtcgagct ccagggcttt ta      52

<210> SEQ ID NO 15
<211> LENGTH: 52
<212> TYPE: DNA
<213> ORGANISM: Homo sapiens

<400> SEQUENCE: 15
cgctcagact ccaggtcttc ctggagytca gagatctgag attccagctc cc      52

<210> SEQ ID NO 16
<211> LENGTH: 52
<212> TYPE: DNA
<213> ORGANISM: Homo sapiens

<400> SEQUENCE: 16
cccaacactc ttggggacca aatataytta atggttaagg gacttgtccc aa      52

<210> SEQ ID NO 17
<211> LENGTH: 52
<212> TYPE: DNA
<213> ORGANISM: Homo sapiens

<400> SEQUENCE: 17
gcctgcctct gccacagcaa ggctgtyggg gtcaagctgg aaaggccagc ag    52

<210> SEQ ID NO 18
<211> LENGTH: 52
<212> TYPE: DNA
<213> ORGANISM: Homo sapiens

<400> SEQUENCE: 18
acaggtgtgc ctgttcacac agagtasaaa gacaggcacc ctctttctac ca    52

<210> SEQ ID NO 19
<211> LENGTH: 52
<212> TYPE: DNA
<213> ORGANISM: Homo sapiens

<400> SEQUENCE: 19
tttatgtacc cagtcataca ccgtttygca agtttgctgt tggactatca tg    52

<210> SEQ ID NO 20
<211> LENGTH: 52
<212> TYPE: DNA
<213> ORGANISM: Homo sapiens

<400> SEQUENCE: 20
ttccgcagct gtttgatggc ttcgtcycgg ttcttgttgg ccgagtcgat gt    52

<210> SEQ ID NO 21
<211> LENGTH: 52
<212> TYPE: DNA
<213> ORGANISM: Homo sapiens

<400> SEQUENCE: 21
aaggatgatg tgggcaagag tgtccaygag ctggagaagt ccaagcgggc cc    52

<210> SEQ ID NO 22
<211> LENGTH: 52
<212> TYPE: DNA
<213> ORGANISM: Homo sapiens

<400> SEQUENCE: 22
cgctcagact ccaggtcttc ctggagytca gagatctgag attccagctc cc    52

<210> SEQ ID NO 23
<211> LENGTH: 52
<212> TYPE: DNA
<213> ORGANISM: Homo sapiens

<400> SEQUENCE: 23
cctcaaagca tgactcgccc ggaaatytgg ggctgaatgg agagggcttt ag    52

<210> SEQ ID NO 24
<211> LENGTH: 52
<212> TYPE: DNA
<213> ORGANISM: Homo sapiens

<400> SEQUENCE: 24
attttcctag atcaaaggat aattttkaaa ggtcacgagc tcccctgaaa ca    52

<210> SEQ ID NO 25
<211> LENGTH: 52
<212> TYPE: DNA
<213> ORGANISM: Homo sapiens

<400> SEQUENCE: 25
agaggctgcc acacggcgct cacctgygcc accaggccac cttctccgtg cc    52

<210> SEQ ID NO 26
<211> LENGTH: 52
<212> TYPE: DNA
<213> ORGANISM: Homo sapiens

<400> SEQUENCE: 26
ctcacggctg gcaaagaaga gctttcyaga ggggaaagga caaacccttc cc    52

<210> SEQ ID NO 27
<211> LENGTH: 52
<212> TYPE: DNA
<213> ORGANISM: Homo sapiens

<400> SEQUENCE: 27
actttgctct ggccaatgcg gtacagrttg ctgtcgagct ccagggcttt ta    52

<210> SEQ ID NO 28
<211> LENGTH: 52
<212> TYPE: DNA
<213> ORGANISM: Homo sapiens

<400> SEQUENCE: 28
caggtgtgag gtcaaagcaa gcctggyact cactggcttc tcaatgaggt cg    52

<210> SEQ ID NO 29
<211> LENGTH: 52
<212> TYPE: DNA
<213> ORGANISM: Homo sapiens

<400> SEQUENCE: 29
aggagatggc caactcagat cgatgcrgga ccatgagaag cagggttctt aa    52

<210> SEQ ID NO 30
<211> LENGTH: 52
<212> TYPE: DNA
<213> ORGANISM: Homo sapiens

<400> SEQUENCE: 30
tgaagcttct ccagtgctct agatggsgtt atgccacctc tctccgggtt gc    52

<210> SEQ ID NO 31
<211> LENGTH: 52
<212> TYPE: DNA
<213> ORGANISM: Homo sapiens

<400> SEQUENCE: 31
taatttcaag atctcgacat agtcacrggc aaggctccca ttaaggagga gc    52

<210> SEQ ID NO 32
<211> LENGTH: 52
<212> TYPE: DNA
<213> ORGANISM: Homo sapiens

<400> SEQUENCE: 32
gcaaccagtg ggctctttgg cctactyagt ttactctgca gcccacctcc cc    52

<210> SEQ ID NO 33
<211> LENGTH: 52
<212> TYPE: DNA
<213> ORGANISM: Homo sapiens

```
<400> SEQUENCE: 33
ggatggaagg aaatggtgtt cctgtcrtac acggtgtgag gcagatgccc ag          52

<210> SEQ ID NO 34
<211> LENGTH: 52
<212> TYPE: DNA
<213> ORGANISM: Homo sapiens

<400> SEQUENCE: 34
ctgacacctt tacccaagga tccatcrcgg tggttctcca gcattagtga aa          52

<210> SEQ ID NO 35
<211> LENGTH: 52
<212> TYPE: DNA
<213> ORGANISM: Homo sapiens

<400> SEQUENCE: 35
tctcttgggg agccatgcat ctgccayggc cacctcacct tcctgtcacc ta          52

<210> SEQ ID NO 36
<211> LENGTH: 52
<212> TYPE: DNA
<213> ORGANISM: Homo sapiens

<400> SEQUENCE: 36
agatctggcc agcacctccc cgtgagygct cctcaccttg ccggcatagt gg          52

<210> SEQ ID NO 37
<211> LENGTH: 52
<212> TYPE: DNA
<213> ORGANISM: Homo sapiens

<400> SEQUENCE: 37
tggaaggaga gaacagaagc ctgcgtraag ccaaggcagc cttgggcacc ca          52

<210> SEQ ID NO 38
<211> LENGTH: 52
<212> TYPE: DNA
<213> ORGANISM: Homo sapiens

<400> SEQUENCE: 38
attttcctag atcaaaggat aattttkaaa ggtcacgagc tccctgaaa ca           52

<210> SEQ ID NO 39
<211> LENGTH: 52
<212> TYPE: DNA
<213> ORGANISM: Homo sapiens

<400> SEQUENCE: 39
ctcacggctg gcaaagaaga gctttcyaga ggggaaagga caaacccttc cc          52

<210> SEQ ID NO 40
<211> LENGTH: 52
<212> TYPE: DNA
<213> ORGANISM: Homo sapiens

<400> SEQUENCE: 40
gggcctcaag agcttgttta atccacrtaa tcctgtatgg tgggtggtca tt          52

<210> SEQ ID NO 41
<211> LENGTH: 52
<212> TYPE: DNA
<213> ORGANISM: Homo sapiens
```

<400> SEQUENCE: 41
taatttcaag atctcgacat agtcacrggc aaggctccca ttaaggagga gc    52

<210> SEQ ID NO 42
<211> LENGTH: 52
<212> TYPE: DNA
<213> ORGANISM: Homo sapiens

<400> SEQUENCE: 42
agaggctgcc acacggcgct cacctgygcc accaggccac cttctccgtg cc    52

<210> SEQ ID NO 43
<211> LENGTH: 52
<212> TYPE: DNA
<213> ORGANISM: Homo sapiens

<400> SEQUENCE: 43
aggagatggc caactcagat cgatgcrgga ccatgagaag cagggttctt aa    52

<210> SEQ ID NO 44
<211> LENGTH: 52
<212> TYPE: DNA
<213> ORGANISM: Homo sapiens

<400> SEQUENCE: 44
ctccggagca caggctaacc ccatgcrtgg aaaagtcaga aaacgtgaag ac    52

<210> SEQ ID NO 45
<211> LENGTH: 52
<212> TYPE: DNA
<213> ORGANISM: Homo sapiens

<400> SEQUENCE: 45
ggcagctgta cctcccctga gccccayggg gcagagagga aggcgtcctg gc    52

<210> SEQ ID NO 46
<211> LENGTH: 52
<212> TYPE: DNA
<213> ORGANISM: Homo sapiens

<400> SEQUENCE: 46
ccctgagtgc acaagaactg ttttgcyatg aaataaatgg ctcttttaag ac    52

<210> SEQ ID NO 47
<211> LENGTH: 52
<212> TYPE: DNA
<213> ORGANISM: Homo sapiens

<400> SEQUENCE: 47
gcaaaatgtt taggtgtcgg acatctycac acacaacagt agcacaaaaa ca    52

<210> SEQ ID NO 48
<211> LENGTH: 52
<212> TYPE: DNA
<213> ORGANISM: Homo sapiens

<400> SEQUENCE: 48
ggatggaagg aaatggtgtt cctgtcrtac acggtgtgag gcagatgccc ag    52

<210> SEQ ID NO 49
<211> LENGTH: 52
<212> TYPE: DNA
<213> ORGANISM: Homo sapiens

```
<400> SEQUENCE: 49
caggtgtgag gtcaaagcaa gcctggyact cactggcttc tcaatgaggt cg          52

<210> SEQ ID NO 50
<211> LENGTH: 52
<212> TYPE: DNA
<213> ORGANISM: Homo sapiens

<400> SEQUENCE: 50
tagagcccgg atgctcctgg ccttccmttt atccacccag cagtgggcaa ca          52

<210> SEQ ID NO 51
<211> LENGTH: 52
<212> TYPE: DNA
<213> ORGANISM: Homo sapiens

<400> SEQUENCE: 51
cagctcagca ggctgggccc aggaggkagg aagggggaacc tgaccgcagg ta          52

<210> SEQ ID NO 52
<211> LENGTH: 52
<212> TYPE: DNA
<213> ORGANISM: Homo sapiens

<400> SEQUENCE: 52
gcaaccagtg ggctctttgg cctactyagt ttactctgca gcccacctcc cc          52

<210> SEQ ID NO 53
<211> LENGTH: 52
<212> TYPE: DNA
<213> ORGANISM: Homo sapiens

<400> SEQUENCE: 53
ctcacacctg gctaggagga gcatctkcgg gggagagtgc cattgggcag ct          52

<210> SEQ ID NO 54
<211> LENGTH: 52
<212> TYPE: DNA
<213> ORGANISM: Homo sapiens

<400> SEQUENCE: 54
acttagctgc tgtggaaaac tatatgrcgg ttctttgaaa acttaaacat ag          52

<210> SEQ ID NO 55
<211> LENGTH: 52
<212> TYPE: DNA
<213> ORGANISM: Homo sapiens

<400> SEQUENCE: 55 gggcaccca cccttcaaga agccaargcc cggacatcag aatcccctga at           52

<210> SEQ ID NO 56
<211> LENGTH: 52
<212> TYPE: DNA
<213> ORGANISM: Homo sapiens

<400> SEQUENCE: 56
acaggtgtgc ctgttcacac agagtasaaa gacaggcacc ctctttctac ca          52

<210> SEQ ID NO 57
<211> LENGTH: 52
<212> TYPE: DNA
```

-continued

<400> SEQUENCE: 57
tccttaggga cagggccctt taatttsgtc cacatgataa tcttatcaag ca     52

<210> SEQ ID NO 58
<211> LENGTH: 52
<212> TYPE: DNA
<213> ORGANISM: Homo sapiens

<400> SEQUENCE: 58
actcctctca aggggcaggg ctggggrtcc tcagacagcc acggacctgt gc     52

<210> SEQ ID NO 59
<211> LENGTH: 51
<212> TYPE: DNA
<213> ORGANISM: Homo sapiens

<400> SEQUENCE: 59
agaggaagtg caggctgtga atgtagygta tctcctaagc gagccaaggc c      51

<210> SEQ ID NO 60
<211> LENGTH: 52
<212> TYPE: DNA
<213> ORGANISM: Homo sapiens

<400> SEQUENCE: 60
gttcctctgt ccactctcag ccgcacwcct cagagtgtaa aagcaggtcc ct     52

<210> SEQ ID NO 61
<211> LENGTH: 52
<212> TYPE: DNA
<213> ORGANISM: Homo sapiens

<400> SEQUENCE: 61
aactggaaaa gaggtctggg ggcctastgt aaaccccatt ccctccaagg aa     52

<210> SEQ ID NO 62
<211> LENGTH: 52
<212> TYPE: DNA
<213> ORGANISM: Homo sapiens

<400> SEQUENCE: 62
catatgtgtg ctctgacagc tccgtgwcta tgttagccct tattagtgtc aa     52

<210> SEQ ID NO 63
<211> LENGTH: 52
<212> TYPE: DNA
<213> ORGANISM: Homo sapiens

<400> SEQUENCE: 63
tttatgtacc cagtcataca ccgtttygca agtttgctgt tggactatca tg     52

<210> SEQ ID NO 64
<211> LENGTH: 52
<212> TYPE: DNA
<213> ORGANISM: Homo sapiens

<400> SEQUENCE: 64
gagccaagtt gaaaccacac acgcgtragg gttatagcca cctaatttgt ta     52

<210> SEQ ID NO 65
<211> LENGTH: 52
<212> TYPE: DNA
<213> ORGANISM: Homo sapiens -continued

<400> SEQUENCE: 65
gaggggcaga tgatcccctt tgactcrccc ccaggttgga agcggctgac ag     52

<210> SEQ ID NO 66
<211> LENGTH: 52
<212> TYPE: DNA
<213> ORGANISM: Homo sapiens

<400> SEQUENCE: 66
acgaagcacc atttacacta ctttgcrtct ggtgttttc acttacaaca ta     52

<210> SEQ ID NO 67
<211> LENGTH: 52
<212> TYPE: DNA
<213> ORGANISM: Homo sapiens

<400> SEQUENCE: 67
aaacttagat cttttgaaat aaaatgrgga cacactaaag gatttacaga aa    52

<210> SEQ ID NO 68
<211> LENGTH: 52
<212> TYPE: DNA
<213> ORGANISM: Homo sapiens

<400> SEQUENCE: 68
agtaatttca cttttagagt cctcccscta gaggaacagc cctaagtatg tg     52

<210> SEQ ID NO 69
<211> LENGTH: 52
<212> TYPE: DNA
<213> ORGANISM: Homo sapiens

<400> SEQUENCE: 69
gtgaagtggc atgttcctag gtctacrctg cgagcccct ccaggacagg gc     52

<210> SEQ ID NO 70
<211> LENGTH: 52
<212> TYPE: DNA
<213> ORGANISM: Homo sapiens

<400> SEQUENCE: 70
gtcccggttc ttgttggccg agtcgaygtg cgcctccagg tccttcaggt cc     52

<210> SEQ ID NO 71
<211> LENGTH: 52
<212> TYPE: DNA
<213> ORGANISM: Homo sapiens

<400> SEQUENCE: 71
gcgctccgcc caggaggacc cggccayggt gtgtgcgcaa gggcagtggc ct     52

<210> SEQ ID NO 72
<211> LENGTH: 52
<212> TYPE: DNA
<213> ORGANISM: Homo sapiens

<400> SEQUENCE: 72
gcctgcctct gccacagcaa ggctgtyggg gtcaagctgg aaaggccagc ag     52

<210> SEQ ID NO 73
<211> LENGTH: 52
<212> TYPE: DNA
<213> ORGANISM: Homo sapiens

<400> SEQUENCE: 73
cccaacactc ttggggacca aatataytta atggttaagg acttgtccc aa         52

<210> SEQ ID NO 74
<211> LENGTH: 52
<212> TYPE: DNA
<213> ORGANISM: Homo sapiens

<400> SEQUENCE: 74
ccatcacgtg atcttgagat gtagccygtg aagtttcgct ggaatagatg tg         52

<210> SEQ ID NO 75
<211> LENGTH: 52
<212> TYPE: DNA
<213> ORGANISM: Homo sapiens

<400> SEQUENCE: 75
ttccgcagct gtttgatggc ttcgtcycgg ttcttgttgg ccgagtcgat gt         52

<210> SEQ ID NO 76
<211> LENGTH: 52
<212> TYPE: DNA
<213> ORGANISM: Homo sapiens

<400> SEQUENCE: 76
ccactctgca aggaccaccc tgagagmagg ccgggctcag aatgagtcag ag         52

<210> SEQ ID NO 77
<211> LENGTH: 52
<212> TYPE: DNA
<213> ORGANISM: Homo sapiens

<400> SEQUENCE: 77
tcagctctag gaacctggcc ctggacracc catgtgaaag cagcacttaa ac         52

<210> SEQ ID NO 78
<211> LENGTH: 52
<212> TYPE: DNA
<213> ORGANISM: Homo sapiens

<400> SEQUENCE: 78
ccactttggg ctccaggctg tttactraga atgtcaataa atcctactgt ga         52

<210> SEQ ID NO 79
<211> LENGTH: 52
<212> TYPE: DNA
<213> ORGANISM: Homo sapiens

<400> SEQUENCE: 79
actttgctct ggccaatgcg gtacagrttg ctgtcgagct ccagggcttt ta         52

<210> SEQ ID NO 80
<211> LENGTH: 52
<212> TYPE: DNA
<213> ORGANISM: Homo sapiens

<400> SEQUENCE: 80
gacacctatg tgtacccggc ttcttaygac gggcactgca aatagcccca tt         52

<210> SEQ ID NO 81
<211> LENGTH: 52
<212> TYPE: DNA
<213> ORGANISM: Homo sapiens

<400> SEQUENCE: 81
tgattaacat gcgtccttca tcctacraga gagaagttgt cccatctcca ac        52

<210> SEQ ID NO 82
<211> LENGTH: 52
<212> TYPE: DNA
<213> ORGANISM: Homo sapiens

<400> SEQUENCE: 82
cacttcaccc tggccagtcc attcaarcaa atccaaggtt tctccctgcc ag        52

<210> SEQ ID NO 83
<211> LENGTH: 52
<212> TYPE: DNA
<213> ORGANISM: Homo sapiens

<400> SEQUENCE: 83
cgctcagact ccaggtcttc ctggagytca gagatctgag attccagctc cc        52

<210> SEQ ID NO 84
<211> LENGTH: 52
<212> TYPE: DNA
<213> ORGANISM: Homo sapiens

<400> SEQUENCE: 84
cattctggca ccttctgtca cctacckcca cggcctaatc caaggcacta ca        52

<210> SEQ ID NO 85
<211> LENGTH: 52
<212> TYPE: DNA
<213> ORGANISM: Homo sapiens

<400> SEQUENCE: 85
ctgtaaataa ggaaagccct aagctcygtg ttgggtttgc actagccgat cc        52

<210> SEQ ID NO 86
<211> LENGTH: 52
<212> TYPE: DNA
<213> ORGANISM: Homo sapiens

<400> SEQUENCE: 86
tgttccctat ctccccgtca ccgaacrcag gctgtgcaca cagtaggtgt tg        52

<210> SEQ ID NO 87
<211> LENGTH: 52
<212> TYPE: DNA
<213> ORGANISM: Homo sapiens

<400> SEQUENCE: 87
gacgaaggga gtagaagaat agactcytaa ggaaagatta aaggagctca gt        52

<210> SEQ ID NO 88
<211> LENGTH: 52
<212> TYPE: DNA
<213> ORGANISM: Homo sapiens

<400> SEQUENCE: 88
gatgcgggtc cagcttgccg gcctggrgaa gaaaacacat gcatgcggtc tc        52

<210> SEQ ID NO 89
<211> LENGTH: 52
<212> TYPE: DNA
<213> ORGANISM: Homo sapiens

<400> SEQUENCE: 89
tcaggttcta agaggccact tcctttytat ctcccgctca gtgggcccag ag    52

<210> SEQ ID NO 90
<211> LENGTH: 1960
<212> TYPE: PRT
<213> ORGANISM: Homo sapiens

<400> SEQUENCE: 90

```
Met Ala Gln Gln Ala Ala Asp Lys Tyr Leu Tyr Val Asp Lys Asn Phe
1               5                   10                  15

Ile Asn Asn Pro Leu Ala Gln Ala Asp Trp Ala Ala Lys Lys Leu Val
            20                  25                  30

Trp Val Pro Ser Asp Lys Ser Gly Phe Glu Pro Ala Ser Leu Lys Glu
        35                  40                  45

Glu Val Gly Glu Glu Ala Ile Val Glu Leu Val Glu Asn Gly Lys Lys
    50                  55                  60

Val Lys Val Asn Lys Asp Asp Ile Gln Lys Met Asn Pro Pro Lys Phe
65                  70                  75                  80

Ser Lys Val Glu Asp Met Ala Glu Leu Thr Cys Leu Asn Glu Ala Ser
                85                  90                  95

Val Leu His Asn Leu Lys Glu Arg Tyr Tyr Ser Gly Leu Ile Tyr Thr
            100                 105                 110

Tyr Ser Gly Leu Phe Cys Val Val Ile Asn Pro Tyr Lys Asn Leu Pro
        115                 120                 125

Ile Tyr Ser Glu Glu Ile Val Glu Met Tyr Lys Gly Lys Lys Arg His
    130                 135                 140

Glu Met Pro Pro His Ile Tyr Ala Ile Thr Asp Thr Ala Tyr Arg Ser
145                 150                 155                 160

Met Met Gln Asp Arg Glu Asp Gln Ser Ile Leu Cys Thr Gly Glu Ser
                165                 170                 175

Gly Ala Gly Lys Thr Glu Asn Thr Lys Lys Val Ile Gln Tyr Leu Ala
            180                 185                 190

Tyr Val Ala Ser Ser His Lys Ser Lys Lys Asp Gln Gly Glu Leu Glu
        195                 200                 205

Arg Gln Leu Leu Gln Ala Asn Pro Ile Leu Glu Ala Phe Gly Asn Ala
    210                 215                 220

Lys Thr Val Lys Asn Asp Asn Ser Ser Arg Phe Gly Lys Phe Ile Arg
225                 230                 235                 240

Ile Asn Phe Asp Val Asn Gly Tyr Ile Val Gly Ala Asn Ile Glu Thr
                245                 250                 255

Tyr Leu Leu Glu Lys Ser Arg Ala Ile Arg Gln Ala Lys Glu Glu Arg
            260                 265                 270

Thr Phe His Ile Phe Tyr Tyr Leu Leu Ser Gly Ala Gly Glu His Leu
        275                 280                 285

Lys Thr Asp Leu Leu Leu Glu Pro Tyr Asn Lys Tyr Arg Phe Leu Ser
    290                 295                 300

Asn Gly His Val Thr Ile Pro Gly Gln Gln Asp Lys Asp Met Phe Gln
305                 310                 315                 320

Glu Thr Met Glu Ala Met Arg Ile Met Gly Ile Pro Glu Glu Glu Gln
                325                 330                 335

Met Gly Leu Leu Arg Val Ile Ser Gly Val Leu Gln Leu Gly Asn Ile
            340                 345                 350
```

```
Val Phe Lys Lys Glu Arg Asn Thr Asp Gln Ala Ser Met Pro Asp Asn
            355                 360                 365

Thr Ala Ala Gln Lys Val Ser His Leu Leu Gly Ile Asn Val Thr Asp
370                 375                 380

Phe Thr Arg Gly Ile Leu Thr Pro Arg Ile Lys Val Gly Arg Asp Tyr
385                 390                 395                 400

Val Gln Lys Ala Gln Thr Lys Glu Gln Ala Asp Phe Ala Ile Glu Ala
                405                 410                 415

Leu Ala Lys Ala Thr Tyr Glu Arg Met Phe Arg Trp Leu Val Leu Arg
            420                 425                 430

Ile Asn Lys Ala Leu Asp Lys Thr Lys Arg Gln Gly Ala Ser Phe Ile
        435                 440                 445

Gly Ile Leu Asp Ile Ala Gly Phe Glu Ile Phe Asp Leu Asn Ser Phe
    450                 455                 460

Glu Gln Leu Cys Ile Asn Tyr Thr Asn Glu Lys Leu Gln Gln Leu Phe
465                 470                 475                 480

Asn His Thr Met Phe Ile Leu Glu Gln Glu Glu Tyr Gln Arg Glu Gly
                485                 490                 495

Ile Glu Trp Asn Phe Ile Asp Phe Gly Leu Asp Leu Gln Pro Cys Ile
            500                 505                 510

Asp Leu Ile Glu Lys Pro Ala Gly Pro Pro Gly Ile Leu Ala Leu Leu
        515                 520                 525

Asp Glu Glu Cys Trp Phe Pro Lys Ala Thr Asp Lys Ser Phe Val Glu
    530                 535                 540

Lys Val Met Gln Glu Gln Gly Thr His Pro Lys Phe Gln Lys Pro Lys
545                 550                 555                 560

Gln Leu Lys Asp Lys Ala Asp Phe Cys Ile Ile His Tyr Ala Gly Lys
                565                 570                 575

Val Asp Tyr Lys Ala Asp Glu Trp Leu Met Lys Asn Met Asp Pro Leu
            580                 585                 590

Asn Asp Asn Ile Ala Thr Leu Leu His Gln Ser Ser Asp Lys Phe Val
        595                 600                 605

Ser Glu Leu Trp Lys Asp Val Asp Arg Ile Ile Gly Leu Asp Gln Val
    610                 615                 620

Ala Gly Met Ser Glu Thr Ala Leu Pro Gly Ala Phe Lys Thr Arg Lys
625                 630                 635                 640

Gly Met Phe Arg Thr Val Gly Gln Leu Tyr Lys Glu Gln Leu Ala Lys
                645                 650                 655

Leu Met Ala Thr Leu Arg Asn Thr Asn Pro Asn Phe Val Arg Cys Ile
            660                 665                 670

Ile Pro Asn His Glu Lys Lys Ala Gly Lys Leu Asp Pro His Leu Val
        675                 680                 685

Leu Asp Gln Leu Arg Cys Asn Gly Val Leu Glu Gly Ile Arg Ile Cys
    690                 695                 700

Arg Gln Gly Phe Pro Asn Arg Val Val Phe Gln Glu Phe Arg Gln Arg
705                 710                 715                 720

Tyr Glu Ile Leu Thr Pro Asn Ser Ile Pro Lys Gly Phe Met Asp Gly
                725                 730                 735

Lys Gln Ala Cys Val Leu Met Ile Lys Ala Leu Glu Leu Asp Ser Asn
            740                 745                 750

Leu Tyr Arg Ile Gly Gln Ser Lys Val Phe Phe Arg Ala Gly Val Leu
        755                 760                 765
```

```
Ala His Leu Glu Glu Arg Asp Leu Lys Ile Thr Asp Val Ile Ile
    770                 775                 780

Gly Phe Gln Ala Cys Cys Arg Gly Tyr Leu Ala Arg Lys Ala Phe Ala
785                 790                 795                 800

Lys Arg Gln Gln Gln Leu Thr Ala Met Lys Val Leu Gln Arg Asn Cys
                805                 810                 815

Ala Ala Tyr Leu Lys Leu Arg Asn Trp Gln Trp Trp Arg Leu Phe Thr
            820                 825                 830

Lys Val Lys Pro Leu Leu Gln Val Ser Arg Gln Glu Glu Met Met
                835                 840                 845

Ala Lys Glu Glu Glu Leu Val Lys Val Arg Glu Lys Gln Leu Ala Ala
850                 855                 860

Glu Asn Arg Leu Thr Glu Met Glu Thr Leu Gln Ser Gln Leu Met Ala
865                 870                 875                 880

Glu Lys Leu Gln Leu Gln Glu Gln Leu Gln Ala Glu Thr Glu Leu Cys
                885                 890                 895

Ala Glu Ala Glu Glu Leu Arg Ala Arg Leu Thr Ala Lys Lys Gln Glu
            900                 905                 910

Leu Glu Glu Ile Cys His Asp Leu Glu Ala Arg Val Glu Glu Glu Glu
                915                 920                 925

Glu Arg Cys Gln His Leu Gln Ala Glu Lys Lys Lys Met Gln Gln Asn
930                 935                 940

Ile Gln Glu Leu Glu Glu Gln Leu Glu Glu Glu Ser Ala Arg Gln
945                 950                 955                 960

Lys Leu Gln Leu Glu Lys Val Thr Thr Glu Ala Lys Leu Lys Lys Leu
                965                 970                 975

Glu Glu Glu Gln Ile Ile Leu Glu Asp Gln Asn Cys Lys Leu Ala Lys
                980                 985                 990

Glu Lys Lys Leu Leu Glu Asp Arg Ile Ala Glu Phe Thr Thr Asn Leu
                995                 1000                1005

Thr Glu Glu Glu Glu Lys Ser Lys Ser Leu Ala Lys Leu Lys Asn
    1010                1015                1020

Lys His Glu Ala Met Ile Thr Asp Leu Glu Glu Arg Leu Arg Arg
    1025                1030                1035

Glu Glu Lys Gln Arg Gln Glu Leu Glu Lys Thr Arg Arg Lys Leu
    1040                1045                1050

Glu Gly Asp Ser Thr Asp Leu Ser Asp Gln Ile Ala Glu Leu Gln
    1055                1060                1065

Ala Gln Ile Ala Glu Leu Lys Met Gln Leu Ala Lys Lys Glu Glu
    1070                1075                1080

Glu Leu Gln Ala Ala Leu Ala Arg Val Glu Glu Glu Ala Ala Gln
    1085                1090                1095

Lys Asn Met Ala Leu Lys Lys Ile Arg Glu Leu Glu Ser Gln Ile
    1100                1105                1110

Ser Glu Leu Gln Glu Asp Leu Glu Ser Glu Arg Ala Ser Arg Asn
    1115                1120                1125

Lys Ala Glu Lys Gln Lys Arg Asp Leu Gly Glu Glu Leu Glu Ala
    1130                1135                1140

Leu Lys Thr Glu Leu Glu Asp Thr Leu Asp Ser Thr Ala Ala Gln
    1145                1150                1155

Gln Glu Leu Arg Ser Lys Arg Glu Gln Glu Val Asn Ile Leu Lys
    1160                1165                1170
```

-continued

```
Lys Thr Leu Glu Glu Glu Ala Lys Thr His Glu Ala Gln Ile Gln
1175                1180                1185

Glu Met Arg Gln Lys His Ser Gln Ala Val Glu Glu Leu Ala Glu
1190                1195                1200

Gln Leu Glu Gln Thr Lys Arg Val Lys Ala Asn Leu Glu Lys Ala
1205                1210                1215

Lys Gln Thr Leu Glu Asn Glu Arg Gly Glu Leu Ala Asn Glu Val
1220                1225                1230

Lys Val Leu Leu Gln Gly Lys Gly Asp Ser Glu His Lys Arg Lys
1235                1240                1245

Lys Val Glu Ala Gln Leu Gln Glu Leu Gln Val Lys Phe Asn Glu
1250                1255                1260

Gly Glu Arg Val Arg Thr Glu Leu Ala Asp Lys Val Thr Lys Leu
1265                1270                1275

Gln Val Glu Leu Asp Asn Val Thr Gly Leu Leu Ser Gln Ser Asp
1280                1285                1290

Ser Lys Ser Ser Lys Leu Thr Lys Asp Phe Ser Ala Leu Glu Ser
1295                1300                1305

Gln Leu Gln Asp Thr Gln Glu Leu Leu Gln Glu Glu Asn Arg Gln
1310                1315                1320

Lys Leu Ser Leu Ser Thr Lys Leu Lys Gln Val Glu Asp Glu Lys
1325                1330                1335

Asn Ser Phe Arg Glu Gln Leu Glu Glu Glu Glu Glu Ala Lys His
1340                1345                1350

Asn Leu Glu Lys Gln Ile Ala Thr Leu His Ala Gln Val Ala Asp
1355                1360                1365

Met Lys Lys Lys Met Glu Asp Ser Val Gly Cys Leu Glu Thr Ala
1370                1375                1380

Glu Glu Val Lys Arg Lys Leu Gln Lys Asp Leu Glu Gly Leu Ser
1385                1390                1395

Gln Arg His Glu Glu Lys Val Ala Ala Tyr Asp Lys Leu Glu Lys
1400                1405                1410

Thr Lys Thr Arg Leu Gln Gln Glu Leu Asp Asp Leu Leu Val Asp
1415                1420                1425

Leu Asp His Gln Arg Gln Ser Ala Cys Asn Leu Glu Lys Lys Gln
1430                1435                1440

Lys Lys Phe Asp Gln Leu Leu Ala Glu Glu Lys Thr Ile Ser Ala
1445                1450                1455

Lys Tyr Ala Glu Glu Arg Asp Arg Ala Glu Ala Glu Ala Arg Glu
1460                1465                1470

Lys Glu Thr Lys Ala Leu Ser Leu Ala Arg Ala Leu Glu Glu Ala
1475                1480                1485

Met Glu Gln Lys Ala Glu Leu Glu Arg Leu Asn Lys Gln Phe Arg
1490                1495                1500

Thr Glu Met Glu Asp Leu Met Ser Ser Lys Asp Asp Val Gly Lys
1505                1510                1515

Ser Val His Glu Leu Glu Lys Ser Lys Arg Ala Leu Glu Gln Gln
1520                1525                1530

Val Glu Glu Met Lys Thr Gln Leu Glu Glu Leu Glu Asp Glu Leu
1535                1540                1545

Gln Ala Thr Glu Asp Ala Lys Leu Arg Leu Glu Val Asn Leu Gln
1550                1555                1560
```

```
Ala Met Lys Ala Gln Phe Glu Arg Asp Leu Gln Gly Arg Asp Glu
    1565                1570                1575

Gln Ser Glu Glu Lys Lys Gln Leu Val Arg Gln Val Arg Glu
    1580                1585                1590

Met Glu Ala Glu Leu Glu Asp Glu Arg Lys Gln Arg Ser Met Ala
    1595                1600                1605

Val Ala Ala Arg Lys Lys Leu Glu Met Asp Leu Lys Asp Leu Glu
    1610                1615                1620

Ala His Ile Asp Ser Ala Asn Lys Asn Arg Asp Glu Ala Ile Lys
    1625                1630                1635

Gln Leu Arg Lys Leu Gln Ala Gln Met Lys Asp Cys Met Arg Glu
    1640                1645                1650

Leu Asp Asp Thr Arg Ala Ser Arg Glu Glu Ile Leu Ala Gln Ala
    1655                1660                1665

Lys Glu Asn Glu Lys Lys Leu Lys Ser Met Glu Ala Glu Met Ile
    1670                1675                1680

Gln Leu Gln Glu Glu Leu Ala Ala Ala Glu Arg Ala Lys Arg Gln
    1685                1690                1695

Ala Gln Gln Glu Arg Asp Glu Leu Ala Asp Glu Ile Ala Asn Ser
    1700                1705                1710

Ser Gly Lys Gly Ala Leu Ala Leu Glu Glu Lys Arg Arg Leu Glu
    1715                1720                1725

Ala Arg Ile Ala Gln Leu Glu Glu Glu Leu Glu Glu Glu Gln Gly
    1730                1735                1740

Asn Thr Glu Leu Ile Asn Asp Arg Leu Lys Lys Ala Asn Leu Gln
    1745                1750                1755

Ile Asp Gln Ile Asn Thr Asp Leu Asn Leu Glu Arg Ser His Ala
    1760                1765                1770

Gln Lys Asn Glu Asn Ala Arg Gln Gln Leu Glu Arg Gln Asn Lys
    1775                1780                1785

Glu Leu Lys Val Lys Leu Gln Glu Met Glu Gly Thr Val Lys Ser
    1790                1795                1800

Lys Tyr Lys Ala Ser Ile Thr Ala Leu Glu Ala Lys Ile Ala Gln
    1805                1810                1815

Leu Glu Glu Gln Leu Asp Asn Glu Thr Lys Glu Arg Gln Ala Ala
    1820                1825                1830

Cys Lys Gln Val Arg Arg Thr Glu Lys Lys Leu Lys Asp Val Leu
    1835                1840                1845

Leu Gln Val Asp Asp Glu Arg Arg Asn Ala Glu Gln Tyr Lys Asp
    1850                1855                1860

Gln Ala Asp Lys Ala Ser Thr Arg Leu Lys Gln Leu Lys Arg Gln
    1865                1870                1875

Leu Glu Glu Ala Glu Glu Glu Ala Gln Arg Ala Asn Ala Ser Arg
    1880                1885                1890

Arg Lys Leu Gln Arg Glu Leu Glu Asp Ala Thr Glu Thr Ala Asp
    1895                1900                1905

Ala Met Asn Arg Glu Val Ser Ser Leu Lys Asn Lys Leu Arg Arg
    1910                1915                1920

Gly Asp Leu Pro Phe Val Val Pro Arg Arg Met Ala Arg Lys Gly
    1925                1930                1935
```

-continued

```
Ala Gly Asp Gly Ser Asp Glu  Glu Val Asp Gly Lys  Ala Asp Gly
    1940            1945              1950

Ala Glu Ala Lys Pro Ala Glu
    1955            1960
```

SINGLE NUCLEOTIDE POLYMORPHISMS ASSOCIATED WITH RENAL DISEASE

CROSS REFERENCE TO RELATED APPLICATION

This is the U.S. National Stage of International Application No. PCT/US2009/032754, filed Jan. 30, 2009, which was published in English under PCT Article 21(2), which in turn claims the benefit of U.S. Provisional Application No. 61/024,863, filed Jan. 30, 2008, and U.S. Provisional Application No. 61/095,590, filed Sep. 9, 2008, all of which are incorporated herein by reference in their entirety.

FIELD

This disclosure relates to the field of individualized medicine, specifically to the detection of renal disease such as focal segmental glomerulosclerosis (FSGS) or end stage kidney disease (ESKD), determination of risk of a subject to develop renal disease such as FSGS or ESKD, confirmation of the diagnosis of renal disease such as FSGS or ESKD, and the determination of the prognosis of a subject with renal disease such as FSGS or ESKD.

BACKGROUND

The prevalence of chronic kidney disease (CKD) in the United States is now estimated at 13%, and is associated with significant morbidity and mortality (Coresh et al., Am J Kidney Dis 2003; 41(1):1-12). In particular, approximately 100,000 Americans develop end-stage kidney disease (ESKD) each year. The cumulative life-time risk for ESKD varies by race, and is approximately 7.5% for African-Americans and 2.1% for European Americans (Kiberd et al., J Am Soc Nephrol 2002; 13(6):1635-44). In particular, African-Americans have a disproportionate risk for several forms of CKD, among them diabetic nephropathy (Cowie et al., N Engl J Med 1989; 321(16):1074-9), hypertensive nephrosclerosis (Toto, Kidney Int Suppl 2004(92):S102-4), lupus nephritis (Fernandez et al., Arthritis Rheum 2007; 57(4):576-84), focal segmental glomerulosclerosis (Kitiyakara et al., Am J Kidney Dis 2004; 44(5):815-25) (FSGS), and HIV-associated nephropathy (a distinct form of FSGS, also termed collapsing glomerulopathy).

FSGS is a clinical syndrome involving podocyte injury and glomerular scarring, and includes genetic forms with Mendelian inheritance, reactive forms associated with other illnesses (including HIV-1 disease) or medications, and an idiopathic form, which accounts for the majority of cases (Barisoni et al., Clin J Am Soc Nephrol 2007; 2(3):529-42). African-Americans have a 4-fold increased risk for sporadic FSGS (Kitiyakara et al., Semin Nephrol 2003; 23(2):172-82) and an 18-fold to 50-fold increased risk for HIV-1-associated FSGS (Kopp et al., Kidney Int Suppl 2003(83):S43-9; Eggers et al., J Am Soc Nephrol 2004; 15(9):2477-85). Individuals of African ancestry also have increased risk for FSGS in other geographic regions, suggesting that genetic factors contribute to these disparities (Kitiyakara et al., Semin Nephrol 2003; 23(2):172-82).

A need remains for methods for identifying subjects that are at risk for renal disease, including methods that use genetic means of identification.

SUMMARY

Methods are disclosed for detecting a genetic predisposition to focal segmental glomerulosclerosis (FSGS) or hypertensive end-stage kidney disease (ESKD) or both in a human subject. In one embodiment, the human subject is of African ancestry. In another embodiment, the human subject is of European ancestry. The methods include detecting the presence of at least one haplotype including at least two tag single nucleotide polymorphism (SNPs) in a non-coding region of the MYH9 gene encoding myosin heavy chain IIA, such as a haplotype associated with disease risk, and/or detecting the presence of at least one allele for a tag SNP in the MYH9 gene. The presence of the haplotype or the allele determines the genetic predisposition to focal segmental glomerulosclerosis or hypertensive end-stage kidney disease or both.

In a further embodiment, methods are disclosed for detecting a genetic predisposition to renal disease in a human subject by detecting the presence of at least one tag single nucleotide polymorphism in a non-coding region of a MYH9 gene, or a haplotype comprising at least two tag single nucleotide polymorphisms (SNPs) in a non-coding region of a MYH9 gene and wherein the presence of the haplotype or at least one tag single nucleotide polymorphism in the non-coding region of the MYH9 gene determines the genetic predisposition to renal disease in the human subject. In one embodiment the methods utilize the detection of at least one tag SNP present in an intron of the MYH9 gene.

In additional embodiments, the method includes detecting the presence of at least one tag SNP in a non-coding region of the MYH9 gene. In another embodiment, the methods can include detecting multiple haplotype blocks and/or multiple tag SNPs in a non-coding region of the MYH9 gene. The methods can also include detecting the haplotypes and/or the at least one SNP in a non-coding region of the MYH9 gene on one or both chromosomes.

Disclosed herein are methods for detecting a genetic predisposition to renal disease in a human subject of African ancestry by identifying a risk allele associated with renal disease, detecting at least one tag single nucleotide polymorphism, or a haplotype comprising at least two tag single nucleotide polymorphisms (SNPs) associated with the risk allele in a MYH9 gene of the subject, wherein the frequency of the risk allele is at least 5% in subjects of African ancestry. The presence of the haplotype or at least one tag single nucleotide polymorphism in the MYH9 gene determines the genetic predisposition of the human subject to renal disease.

In another embodiment, arrays are provided for detecting a genetic predisposition to renal disease in a human subject. Probes complementary to a tag single nucleotide polymorphism in a non-coding region of a MYH9 gene encoding non-muscle myosin heavy chain IIA are placed in the array. The probes complementary to the tag single nucleotide polymorphisms hybridize specific non-coding regions in the MYH9 gene.

In further embodiments, methods are provided for detecting the presence of at least one tag SNP in a non-coding region of the MYH9 gene that is associated with hypertension, idiopathic FSGS, human immunodeficiency virus, diabetes mellitus, sickle cell anemia, systemic lupus erythematosus, preeclampsia, systemic sclerosis, asthma, lacunar stroke, glaucoma or cerebral malaria.

The foregoing and other features and advantages will become more apparent from the following detailed description of several embodiments, which proceeds with reference to the accompanying figures.

BRIEF DESCRIPTION OF THE FIGURES

FIGS. 1A-1C show the whole genome and chromosome 22 MALD results. FIG. 1A is a graph showing the change in African ancestry, compared to the genome average, across the genome for cases (black) and controls (grey). A horizontal line, indicating the average African ancestry for the genome, is included at 0. FIG. 1B is a graph of the LOD scores of the case control statistic (black) and the locus genome score (grey) across the genome. The horizontal line at a LOD of 2 shows statistical significance at the 0.05 level. Chromosomes and marker locations are plotted along each x axis. FIG. 1C is a graph of the 95% Credible Interval for the location of a genetic factor responsible for the chromosome 22 MALD peak. The probability distribution for the location of the gene responsible for the observed association is shown, with the 95% credible interval, extending from 35.7 to 34.4 Mb, shaded.

FIG. 2 shows the HapMap R squared plot for 152 SNPs polymorphic in YRI; FIG. 2 also shows the exons and introns of MYH9; 17 MYH9 SNPs and their frequency in African-American and European-American controls and in FSGS and ESKD disease groups. Frequencies in bold are significantly (P<0.05) different from frequencies in the appropriate control group. The MALD max SNP is indicated with an asterix, and the four SNP alleles contained in the most strongly associated haplotype are boxed in red. HapMap data and SNPs are shown in gene order (5' to 3'), which for MYH9 is the reverse of genome order; thus the haplotype TCCG shown corresponds to the haplotype GCCT in genome order (Table 1).

FIGS. 3A-3B are a set of digital images showing the localization of myosin IIA protein in mouse glomeruli and cultured human podocytes. For the results shown in FIG. 3A, mouse glomeruli were immunostained for myosin IIA and synaptopodin; the merged image demonstrates extensive colocalization of these two proteins. For the results shown in FIG. 3B, in cultured human podocytes, myosin IIA and F-actin are partially colocalized, suggesting that myosin IIA may contribute to the formation of the actin cytoskeleton. On the other hand, myosin IIA and the slit diaphragm protein nephrin showed no colocalization, suggesting distinct functional roles for these proteins.

Figure 4D:
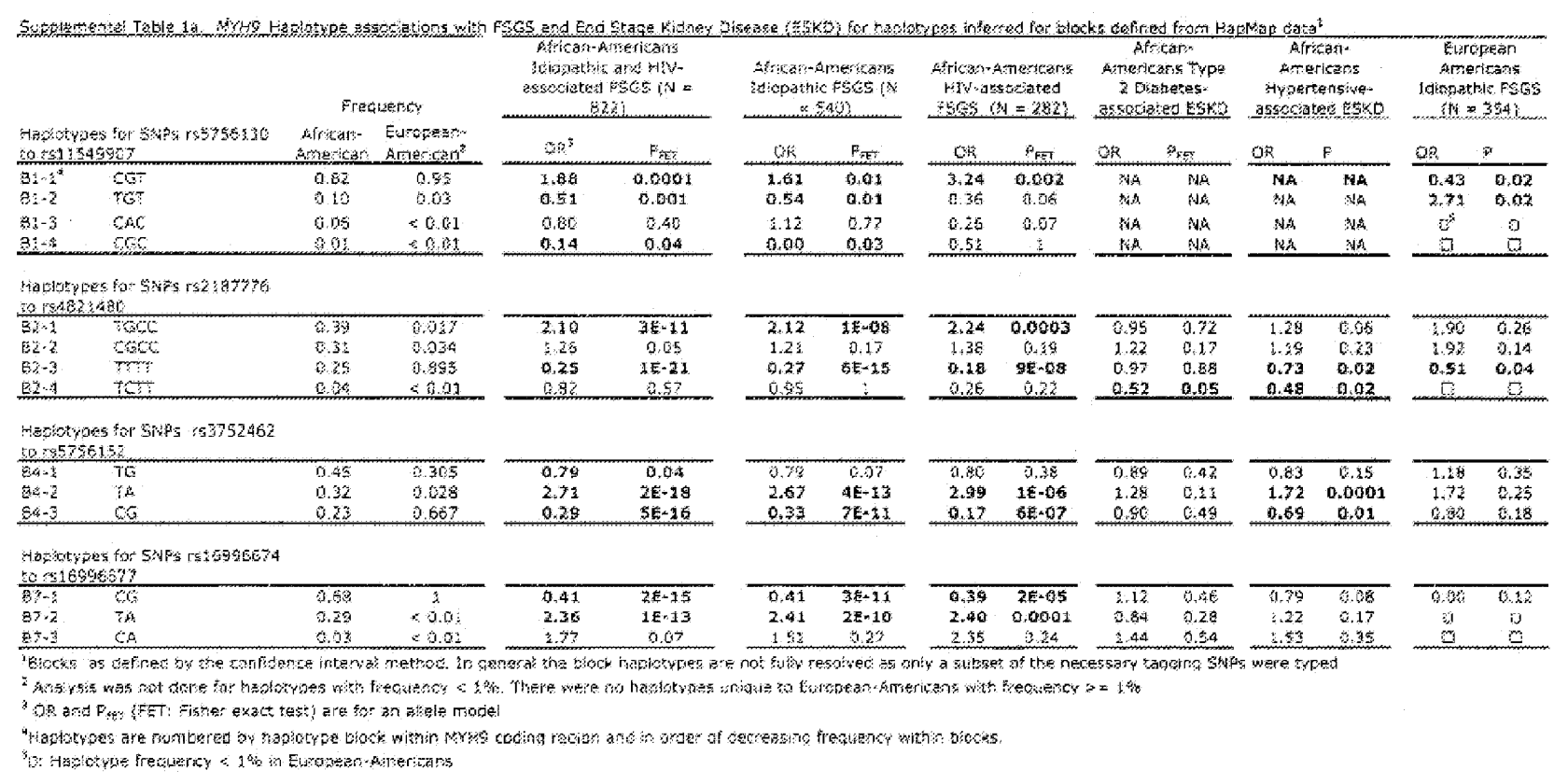

FIGS. 4A-4E are a set of Tables (Table 1a, Table 2, Table 3, Supplmental Table 1a and Supplemental Table 1b) showing the MYH9 allele frequencies, SNP associations with FSGS and SNP associations with ESKD in different populations.

FIGS. 5A-5E are a Table (Table 7) showing the location of SNPs in the non-coding region of the MYH9 gene, the relative significance group of each SNP, the minimum p value and the odds ratio of each SNP.

FIGS. 6A-6B are a Table (Table 8) showing the risk allele and protective allele for SNPs in the non-coding region of the MYH9 gene and the flanking sequence. The sequences shown in FIG. 6 are provided in SEQ ID NOS: 34 to 89 respectively, from top to bottom in the table.

FIG. 7 is a Table (Table 9) showing representative p values and risk alleles in the non-coding region of the MYH9 gene in European-Americans.

SEQUENCE LISTING

Figure 1A:
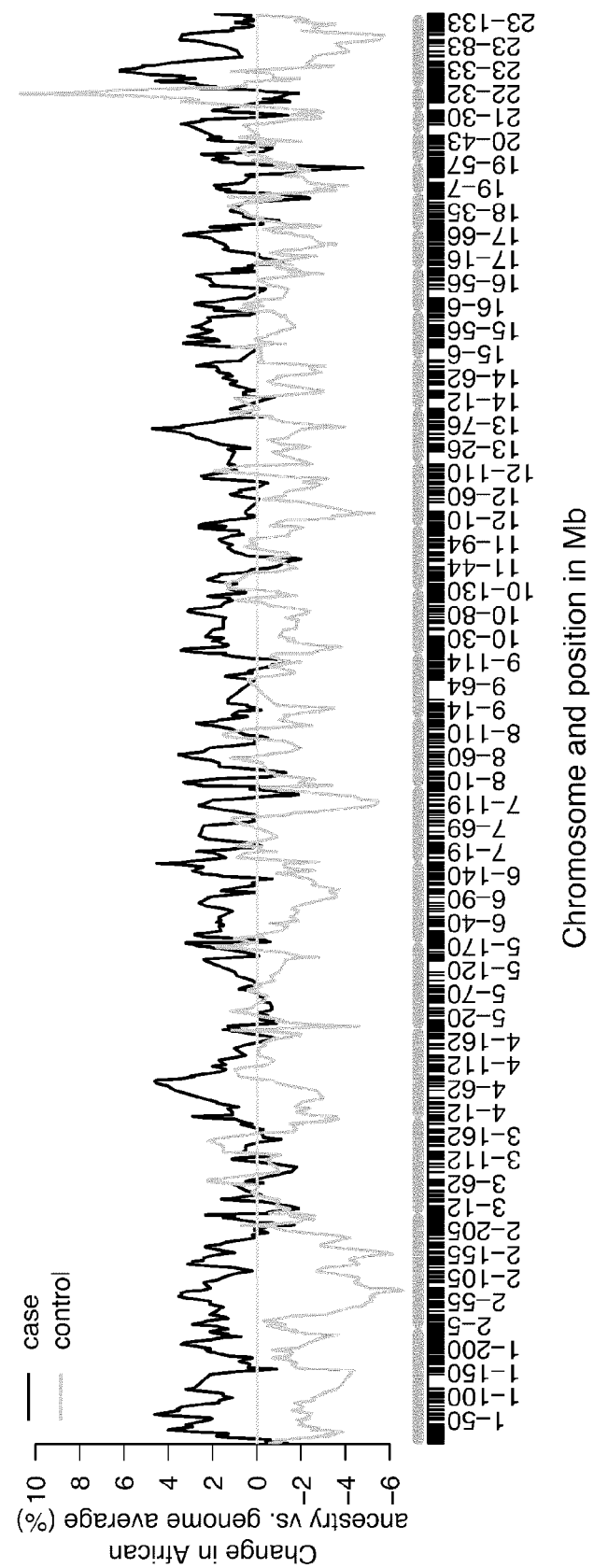

The nucleic acid sequences and amino acid sequences listed are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. It should be noted that single nucleotide polypmorphisms are identified in the leading strand, wherein the risk nucleotide is listed first, and the protective nucleotide is listed second. Due to the complementary nature of DNA, the single nucleotide polymorphism is present in both DNA strands, and thus can also be identified in the lagging strand.

SEQ ID NOs: 1-89 are nucleic acid sequences from the MYH9 gene, each include a single nucleotide polymorphism of interest.

SEQ ID NO: 90 is the amino acid sequence of the human heavy chain myosin IIA.

DETAILED DESCRIPTION

I. Abbreviations
AF: attributal fraction
CKD: chronic kidney disease
EF: explained fraction
ESKD: end-stage kidney disease
FET: Fisher's exact test
FSGS: focal segmental glomerulosclerosis
HIV: human immunodeficiency virus
LD: linkage disequilibrium
LOD: logarithm of the odds
MALD: mapping by admixture linkage disequilibrium
SNP: single nucleotide polymorphism II. Terms Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

African ancestry: An individual whose ancestors are from Sub-Saharan Africa prior to the era of European expansion (prior to about 1500). There are a number of programs that can be used to analyze DNA to determine if an individual is of African ancestry, such as STRUCTURE™ (version 2.2, software available on the internet at the University of Chicago website on Jan. 28, 2009). In one example, African American individuals are those individuals who reside in the United States and self-identify themselves as being of African origin. In another example, African-Americans are individuals who reside in the United States and self-identify as being of African origin, and are of African ancestry as determined by a program that analyzes DNA ancestry, such as STRUCTURE™, version 2.2, Jan. 28, 2009).

Allele: A particular form of a genetic locus, distinguished from other forms by its particular nucleotide sequence, or one of the alternative polymorphisms found at a polymorphic site.

Allele frequency: A measure of the relative frequency of an allele at a genetic locus in a population. Usually allele frequency is expressed as a proportion or a percentage. In population genetics, allele frequencies are used to depict the amount of genetic diversity at the individual, population, or species level. There are various databases in the public domain that contain SNPs and a user may for example, determine the relative allele frequency in some instances using such publicly available databases.

In the instant application the allele frequency for a risk allele is greater than 5% in subjects of African ancestry. In a further embodiment, the allele frequency for a risk allele is greater than at least 10%, at least 15%, at least 20%, at least 25%, at least 30%, at least 35%, at least 40% or at least 50% in subjects of African ancestry. In some embodiments, an uninfected population is used to calculate allele frequency. Risk is elevated in individuals that carry the risk allele.

There are a number of diseases or disorders that are associated with the identification of one or more SNPs or risk alleles. In many cases, the diseases or disorders are autosomal dominant mutations and any associated SNPs are observed only in individuals who present with clinical manifestations of the disease. In other circumstances, the occurrence of a disease-associated SNP is so rare that no-known frequency can be determined (for example, through the use of public domain SNP databases or by comparison with the literature) and these diseases/disorders are correctly defined as having an allele frequency significantly lower than 1%.

Amplification: To increase the number of copies of a nucleic acid molecule. The resulting amplification products are called "amplicons." Amplification of a nucleic acid molecule (such as a DNA or RNA molecule) refers to use of a technique that increases the number of copies of a nucleic acid molecule in a sample. An example of amplification is the polymerase chain reaction (PCR), in which a sample is contacted with a pair of oligonucleotide primers under conditions that allow for the hybridization of the primers to a nucleic acid template in the sample. The primers are extended under suitable conditions, dissociated from the template, re-annealed, extended, and dissociated to amplify the number of copies of the nucleic acid. This cycle can be repeated. The product of amplification can be characterized by such techniques as electrophoresis, restriction endonuclease cleavage patterns, oligonucleotide hybridization or ligation, and/or nucleic acid sequencing.

Other examples of in vitro amplification techniques include quantitative real-time PCR; reverse transcriptase PCR (RT-PCR); real-time PCR (rt PCR); real-time reverse transcriptase PCR (rt RT-PCR); nested PCR; strand displacement amplification (see U.S. Pat. No. 5,744,311); transcription-free isothermal amplification (see U.S. Pat. No. 6,033,881); repair chain reaction amplification (see PCT Publication No. WO 90/01069); ligase chain reaction amplification (see European patent publication No. EP-A-320 308); gap filling ligase chain reaction amplification (see U.S. Pat. No. 5,427,930); coupled ligase detection and PCR (see U.S. Pat. No. 6,027,889); and NASBA™ RNA transcription-free amplification (see U.S. Pat. No. 6,025,134), amongst others.

Array: An arrangement of molecules, such as biological macromolecules (such as polypeptides or nucleic acids) or biological samples (such as tissue sections), in addressable locations on or in a substrate. A "microarray" is an array that is miniaturized so as to require or be aided by microscopic examination for evaluation or analysis. Arrays are sometimes called DNA chips or biochips.

The array of molecules ("features") makes it possible to carry out a very large number of analyses on a sample at one time. In certain example arrays, one or more molecules (such as an oligonucleotide probe) will occur on the array a plurality of times (such as twice), for instance to provide internal controls. The number of addressable locations on the array can vary, for example from a few (such as three) to at least six, at least 20, at least 25, or more. In particular examples, an array includes nucleic acid molecules, such as oligonucleotide sequences that are at least 15 nucleotides in length, such as about 15-40 nucleotides in length, such as at least 18 nucleotides in length, at least 21 nucleotides in length, or even at least 25 nucleotides in length. In one example, the molecule includes oligonucleotides attached to the array via their 5'- or 3'-end.

Within an array, each arrayed sample is addressable, in that its location can be reliably and consistently determined within at least two dimensions of the array. The feature application location on an array can assume different shapes. For example, the array can be regular (such as arranged in uniform rows and columns) or irregular. Thus, in ordered arrays the location of each sample is assigned to the sample at the time when it is applied to the array, and a key may be provided in order to correlate each location with the appropriate target or feature position. Often, ordered arrays are arranged in a symmetrical grid pattern, but samples could be arranged in other patterns (such as in radially distributed lines, spiral lines, or ordered clusters). Addressable arrays usually are computer readable, in that a computer can be programmed to correlate a particular address on the array with information about the sample at that position (such as hybridization or binding data, including for instance signal intensity). In some examples of computer readable formats, the individual features in the array are arranged regularly, for instance in a Cartesian grid pattern, which can be correlated to address information by a computer.

Caucasian: A human racial classification traditionally distinguished by physical characteristics such as very light to brown skin pigmentation and straight to wavy or curly hair, which includes persons having origins in any of the original peoples of Europe, North Africa, or the Middle East. Popularly, the word "white" is used synonymously with "Caucasian" in North America. Such persons retain substantial genetic similarity to natives or inhabitants of Europe, North Africa, or the Middle East. In a particular example, a Caucasian is at least 1/64 Caucasian.

Concordance: The presence of two or more loci or traits (or combination thereof) derived from the same parental chromosome. The opposite of concordance is discordance, that is, the inheritance of only one (of two or more) parental alleles and/or traits associated with a parental chromosome.

Correlation: A correlation between a phenotypic trait and the presence or absence of a genetic marker (or haplotype or genotype) can be observed by measuring the phenotypic trait and comparing it to data showing the presence or absence of one or more genetic markers. Some correlations are stronger than others, meaning that in some instances subjects with FSGS will display a particular genetic marker (i.e., 100% correlation). In other examples the correlation will not be as strong, meaning that a subject with FSGS will only display a particular genetic marker 90%, 85%, 70%, 60%, 55%, or 50% of the time. In some instances, a haplotype which contains information relating to the presence or absence of multiple markers can also be correlated to a genetic predisposition such as the development of FSGS, or the type of onset. Correlations can be described using various statistical analyses known to the skilled artisan.

Decrease: Becoming less or smaller, as in number, amount, size, or intensity. In one example, decreasing the risk of a disease (such as FSGS) includes a decrease in the likelihood of developing the disease by at least about 20%, for example by at least about 30%, 40%, 50%, 60%, 70%, 80%, or 90%. In another example, decreasing the risk of a disease includes a delay in the development of the disease, for example a delay of at least about six months, such as about one year, such as about two years, about five years, or about ten years.

In one example, decreasing the signs and symptoms of FSGS includes decreasing the effects of the disease such as podocyte injury or glomerular scarring by a desired amount, for example by at least 5%, at least 10%, at least 15%, at least 20%, at least 25%, at least 30%, at least 50%, at least 75%, or even at least 90%, as compared to a response in the absence of a therapeutic composition.

DNA (deoxyribonucleic acid): DNA is a long chain polymer which comprises the genetic material of most living organisms (some viruses have genes comprising ribonucleic acid (RNA)). The repeating units in DNA polymers are four different nucleotides, each of which comprises one of the four bases, adenine, guanine, cytosine and thymine bound to a deoxyribose sugar to which a phosphate group is attached. Triplets of nucleotides (referred to as codons) code for each amino acid in a polypeptide, or for a stop signal (termination codon). The term codon is also used for the corresponding (and complementary) sequences of three nucleotides in the mRNA into which the DNA sequence is transcribed.

Unless otherwise specified, any reference to a DNA molecule is intended to include the reverse complement of that DNA molecule. Except where single-strandedness is required by the text herein, DNA molecules, though written to depict only a single strand, encompass both strands of a double-stranded DNA molecule. Thus, a reference to the nucleic acid molecule that encodes a protein, or a fragment thereof, encompasses both the sense strand and its reverse complement. Thus, for instance, it is appropriate to generate probes or primers from the reverse complement sequence of the disclosed nucleic acid molecules.

Dominant Model: A genetic based model that tests the association of having at least one minor allele (e.g. Dd or DD) versus not having the allele at all (dd).

End-stage kidney disease (ESKD) or end-stage renal disease (ESRD): A stage of kidney impairment that is irreversible and cannot be controlled by conservative management alone. ESKD requires dialysis or kidney transplantation to maintain life.

European ancestry: A type of ancestry shared by people who derived from the fertile crescent of the Middle East some 50,000 years ago and spread to occupy Europe, the Middle East, parts of Eurasia and South Asia. There are a number of programs that can be used to analyze DNA to determine if an individual is of European ancestry, such as STRUCTURE™ (version 2.2, software available on the internet at the University of Chicago website on Jan. 28, 2009) and EURODNA™ and ANCESTRYBYDNA™ (available through the DNA print website). In one example, European American individuals are those individuals who reside in the United States and self-identify themselves as being of European origin. In another example, European-Americans are individuals who reside in the United States and self-identify as being of European origin, and are of European ancestry as determined by a program that analyzes DNA ancestry.

Focal segmental glomerulosclerosis (FSGS): A clinical syndrome involving podocyte injury and glomerular scarring, and includes genetic forms with Mendelian inheritance, reactive forms associated with other illnesses (including HIV-1 disease) or medications, and an idiopathic form, which accounts for the majority of cases. The name refers to the appearance of the kidney tissue on biopsy: focal—only some of the glomeruli are involved; segmental—only part of an entire glomerulus is involved; glomerulosclerosis—scarring of the glomerulus. FSGS presents as a nephrotic syndrome (which is characterized by edema (associated with weight gain), hypoalbuminemia (low serum albumin (a protein) in the blood), hyperlipidemia and hypertension (high blood pressure). In adults it may also present as kidney failure and proteinuria, without a full-blown nephrotic syndrome.

There are five mutually exclusive variants of focal segmental glomerulosclerosis that can be distinguished by the pathologic findings seen on renal biopsy: collapsing variant, glomerular tip lesion variant, cellular variant, perihilar variant, and not otherwise specified (NOS) variant. Determining the type of variant can have prognostic value in individuals with primary focal segmental glomerulosclerosis (where no underlying cause is determined). The collapsing variant is associated with higher rate of progression to end-stage renal disease, whereas glomerular tip lesion variant has low rate of progression to end-stage renal disease in most patients. The cellular variant shows a similar clinical presentation to collapsing and glomerular tip variant but has intermediate outcomes between these two variants.

Genetic predisposition: Susceptibility of a subject to a disease, such as renal disease, including FSGS and hypertensive end stage renal disease. Detecting a genetic predisposition can include, but does not necessarily include, detecting the presence of the disease itself, such as but not limited to an early stage of the disease process. Detecting a genetic predisposition also includes detecting the risk of developing the disease, and determining the susceptibility of that subject to developing the disease or to having a poor prognosis for the disease. Thus, if a subject has a genetic predisposition to a disease they do not necessarily develop the disease but are at risk for developing the disease.

Genomic target sequence: A sequence of nucleotides located in a particular region in the human genome that corresponds to one or more specific genetic abnormalities, such as a nucleotide polymorphism, a deletion, an insertion, or an amplification. The target can be for instance a coding sequence; it can also be the non-coding strand that corresponds to a coding sequence. The target can also be a non-coding sequence, such as an intronic sequence. In several examples, genomic target sequences are genomic sequences of genes that encode heavy chain myosin IIA, (MYH9).

Gene: A segment of DNA that contains the coding sequence for a protein, wherein the segment may include promoters, exons, introns, and other untranslated regions that control expression.

Genotype: An unphased 5' to 3' sequence of nucleotide pair(s) found at a set of one or more polymorphic sites in a locus on a pair of homologous chromosomes in an individual. "Genotyping" is a process for determining a genotype of an individual.

Haplotype: A 5' to 3' sequence of nucleotides found at a set of one or more polymorphic sites in a locus on a single chromosome from a single individual. "Haplotype pair" is the two haplotypes found for a locus in a single individual. With regard to a population, haplotypes are the ordered, linear combination of polymorphisms (e.g., single nucleotide polymorphisms (SNPs) in the sequence of each form of a gene (on individual chromosomes) that exist in the population. "Haplotyping" is a process for determining one or more haplotypes in an individual and includes use of family pedigrees, molecular techniques and/or statistical inference. "Haplotype data" is the information concerning one or more of the following for a specific gene: a listing of the haplotype pairs in an individual or in each individual in a population; a listing of the different haplotypes in a population; frequency of each haplotype in that or other populations, and any known associations between one or more haplotypes and a trait.

Haplotype block: Sites of closely located SNPs which are inherited in blocks. A haplotype block includes a group of SNP locations that do not appear to recombine independently and that can be grouped together. Regions corresponding to blocks have a few common haplotypes which account for a large proportion of chromosomes. Identification of haplotype blocks is a way of examining the extent of linkage disequilibrium (LD) in the genome. The "Hap-Map" project (see the internet at the Hap-Map website) describes the mapping of haplotype blocks in the human genome.

There are programs available on the internet for the identification of haplotype blocks, such as the program HAPBLOCK™ which runs on both PC and Unix and is available from the University of Southern California website on the internet. A further program, which in addition to block identification also has visualization and selection of "tagging" SNPs is HAPLOBLOCKFINDER™, which runs interactively on the web or can be downloaded for local machine use (Unix or PC). It can be accessed at the program website available on the internet.

Hybridization: Oligonucleotides and their analogs hybridize by hydrogen bonding, which includes Watson-Crick, Hoogsteen or reversed Hoogsteen hydrogen bonding, between complementary bases. Generally, nucleic acids consist of nitrogenous bases that are either pyrimidines (cytosine (C), uracil (U), and thymine (T)) or purines (adenine (A) and guanine (G)). These nitrogenous bases form hydrogen bonds between a pyrimidine and a purine, and the bonding of the pyrimidine to the purine is referred to as "base pairing." More specifically, A will hydrogen bond to T or U, and G will bond to C. "Complementary" refers to the base pairing that occurs between two distinct nucleic acid sequences or two distinct regions of the same nucleic acid sequence. For example, an oligonucleotide can be complementary to a specific genetic locus, so it specifically hybridizes with a mutant allele (and not the reference allele) or so that it specifically hybridizes with a reference allele (and not the mutant allele).

"Specifically hybridizable" and "specifically complementary" are terms that indicate a sufficient degree of complementarity such that stable and specific binding occurs between the oligonucleotide (or its analog) and the DNA or RNA target. The oligonucleotide or oligonucleotide analog need not be 100% complementary to its target sequence to be specifically hybridizable. An oligonucleotide or analog is specifically hybridizable when binding of the oligonucleotide or analog to the target DNA or RNA molecule interferes with the normal function of the target DNA or RNA, and there is a sufficient degree of complementarity to avoid non-specific binding of the oligonucleotide or analog to non-target sequences under conditions where specific binding is desired, for example under physiological conditions in the case of in vivo assays or systems. Such binding is referred to as specific hybridization. In one example, an oligonucleotide is specifically hybridizable to DNA or RNA nucleic acid sequences including an allele of a gene, wherein it will not hybridize to nucleic acid sequences containing a polymorphism.

Hybridization conditions resulting in particular degrees of stringency will vary depending upon the nature of the hybridization method of choice and the composition and length of the hybridizing nucleic acid sequences. Generally, the temperature of hybridization and the ionic strength (especially the $Na^+$ concentration) of the hybridization buffer will determine the stringency of hybridization, though wash times Also influence stringency. Calculations regarding hybridization conditions required for attaining particular degrees of stringency are discussed by Sambrook et al. (ed.), *Molecular Cloning: A Laboratory Manual,* 2nd ed., vol. 1-3, Cold Spring Harbor Laboratory Press, Cold Spring Harbor, N.Y., 1989, chapters 9 and 11.

The following is an exemplary set of hybridization conditions and is not limiting:

| Very High Stringency (detects sequences that share at least 90% identity) | |
|---|---|
| Hybridization: | 5x SSC at 65° C. for 16 hours |
| Wash twice: | 2x SSC at room temperature (RT) for 15 minutes each |
| Wash twice: | 0.5x SSC at 65° C. for 20 minutes each |

| High Stringency (detects sequences that share at least 80% identity) | |
|---|---|
| Hybridization: | 5x-6x SSC at 65° C.-70° C. for 16-20 hours |
| Wash twice: | 2x SSC at RT for 5-20 minutes each |
| Wash twice: | 1x SSC at 55° C.-70° C. for 30 minutes each |

| Low Stringency (detects sequences that share at least 50% identity) | |
|---|---|
| Hybridization: | 6x SSC at RT to 55° C. for 16-20 hours |
| Wash at least twice: | 2x-3x SSC at RT to 55° C. for 20-30 minutes each. |

Hypertension: High blood pressure; transitory or sustained elevation of systemic arterial blood pressure to a level likely to induce cardiovascular damage or other adverse consequences. Hypertension has been arbitrarily defined as a systolic blood pressure above 140 mm Hg or a diastolic blood pressure above 90 mm Hg. Consequences of uncontrolled hypertension include retinal vascular damage (Keith-Wagener-Barker changes), cerebrovascular disease and stroke, left ventricular hypertrophy and failure, myocardial infarction, dissecting aneurysm, and renovascular disease. An underlying disorder (such as renal disease, Cushing syndrome, pheochromocytoma) is identified in fewer than 10% of all cases of hypertension. The remainder, traditionally labeled "essential" hypertension, probably arise from a variety of disturbances in normal pressure-regulating mechanisms (which involve baroreceptors, autonomic influences on the rate and force of cardiac contraction and vascular tone, renal retention of salt and water, formation of angiotensin II under the influence of renin and angiotensin-converting enzyme, and other factors known and unknown), and most are probably genetically conditioned.

Isolated: An "isolated" biological component (such as a nucleic acid molecule, protein or organelle) has been substantially separated or purified away from other biological components in the cell of the organism in which the component naturally occurs, i.e., other chromosomal and extra-chromosomal DNA and RNA, proteins and organelles. Nucleic acids and proteins that have been "isolated" include nucleic acids and proteins purified by standard purification methods. The term also embraces nucleic acids and proteins prepared by recombinant expression in a host cell as well as chemically synthesized nucleic acids.

Linkage: The association of two or more loci at positions on the same chromosome, such that recombination between the two loci is reduced to a proportion significantly less than 50%. The term linkage can also be used in reference to the association between one or more loci and a trait if an allele (or alleles) and the trait, or absence thereof, are observed together in significantly greater than 50% of occurrences. A linkage group is a set of loci, in which all members are linked either directly or indirectly to all other members of the set.

Linkage Disequilibrium: Co-occurrence of two genetic loci (e.g., markers) at a frequency greater than expected for independent loci based on the allele frequencies. Linkage disequilibrium (LD) typically occurs when two loci are located close together on the same chromosome. When alleles of two genetic loci (such as a marker locus and a causal locus) are in strong LD, the allele observed at one locus (such as a marker locus) is predictive of the allele found at the other locus (for example, a causal locus contributing to a phenotypic trait). The linkage disequilibrium (LD) measure $r^2$ (the squared correlation coefficient) can be used to evaluate how SNPs are related on a haplotype block. For each tag SNP, the $r^2$ between that tag SNP and each additional SNP in a genotyping set can be calculated. The highest of these values is the maximum $r^2$ value, m. In several embodiments, a haplotype block can be identified by SNPs that have an $r^2$ value of greater than or equal to 0.75, greater than or equal to 0.8, greater than or equal to about 0.85, greater than or equal to 0.9, or greater than or equal to 0.95 from the tag SNP. A low $r^2$ value such as less than or equal to 0.3, less than or equal to 0.2, less than or equal to 0.1, is generally considered to be less predictive than a higher $r^2$ value, which is considered a stronger predictor of linkage disequilibrium, such as greater than or equal to 0.75.

Locus: A location on a chromosome or DNA molecule corresponding to a gene or a physical or phenotypic feature, where physical features include polymorphic sites.

MYH9: A gene encoding human heavy chain myosin HA. Myosin II contains two heavy chains, each about 2000 amino acids in length, which constitute the head and tail domains. Each of these heavy chains contains the N-terminal head domain, while the C-terminal tails take on a coiled-coil morphology, holding the two heavy chains together. It also contains 4 light chains (2 per head), which bind the heavy chains in the "neck" region between the head and tail. Mysoin II is an essential component of muscles. Myosin IIA is a non-muscle myosin that is involved in the motion of, and in maintaining the structure of, cells other than muscle cells.

Mutation: Any change of a nucleic acid sequence as a source of genetic variation. For example, mutations can occur within a gene or chromosome, including specific changes in non-coding regions of a chromosome, for instance changes in or near regulatory regions of genes. Types of mutations include, but are not limited to, base substitution point mutations (which are either transitions or transversions), deletions, and insertions. Missense mutations are those that introduce a different amino acid into the sequence of the encoded protein; nonsense mutations are those that introduce a new stop codon; and silent mutations are those that introduce the same amino acid often with a base change in the third position of the codon. In the case of insertions or deletions, mutations can be in-frame (not changing the frame of the overall sequence) or frame shift mutations, which may result in the misreading of a large number of codons (and often leads to abnormal termination of the encoded product due to the presence of a stop codon in the alternative frame).

Non-coding: A change in nucleotide sequence that does not result in the production of a codon that encodes for an amino acid other than the wild-type human sequence, and therefore does not result in the production of any alteration in polypeptide sequence. In the instant application, the term "non-coding" refers to the exclusion of non-synonymous SNPs or haplotypes. In addition, the term "non-coding" also excludes promoter regions of a gene and is therefore limited to intronic and exonic domains of the gene.

Odds Ratio: A calculation performed by analysis of a two by two contingency table. In one example, the first column provides a risk indicator in the absence of a disease (e.g., FSGS). The second column provides the same risk indicator in the presence of the same disease. The first row lists the risk indicator in the absence of a risk factor (such as race) and the second row lists the same risk indicator in the presence of the same risk factor (i.e., race). The Odds Ratio (OR) is determined as the product of the two diagonal entries in the contingency table divided by the product of the two off-diagonal entries of the contingency table. An OR of 1 is indicative of no association. Accordingly, very large or very small ORs are indicative of a strong association between the factors under investigation. The OR is independent of the ratio of cases or controls in a study, group or subset.

Oligonucleotide: An oligonucleotide is a plurality of joined nucleotides joined by native phosphodiester bonds, between about 6 and about 300 nucleotides in length. An oligonucleotide analog refers to moieties that function similarly to oligonucleotides but have non-naturally occurring portions. For example, oligonucleotide analogs can contain non-naturally occurring portions, such as altered sugar moieties or inter-sugar linkages, such as a phosphorothioate oligodeoxynucleotide. Functional analogs of naturally occurring polynucleotides can bind to RNA or DNA, and include peptide nucleic acid (PNA) molecules.

In several examples, oligonucleotides and oligonucleotide analogs can include linear sequences up to about 200 nucleotides in length, for example a sequence (such as DNA or RNA) that is at least 6 bases, for example at least 8, 10, 15, 20, 25, 30, 35, 40, 45, 50, 100 or even 200 bases long, or from about 6 to about 70 bases, for example about 10-25 bases, such as 12, 15 or 20 bases.

Phased: As applied to a sequence of nucleotide pairs for two or more polymorphic sites in a locus, phased means the combination of nucleotides present at those polymorphic sites on a copy of the DNA for the locus.

Polymorphism: A variation in a gene sequence. The polymorphisms can be those variations (DNA sequence differences) which are generally found between individuals or different ethnic groups and geographic locations which, while having a different sequence, produce functionally equivalent gene products. Typically, the term can also refer to variants in the sequence which can lead to gene products that are not functionally equivalent. Polymorphisms also encompass variations which can be classified as alleles and/or mutations which can produce gene products which may have an altered function. Polymorphisms also encompass variations which can be classified as alleles and/or mutations which either produce no gene product or an inactive gene product or an active gene product produced at an abnormal rate or in an inappropriate tissue or in response to an inappropriate stimulus. Alleles are the alternate forms that occur at the polymorphism.

Polymorphisms can be referred to, for instance, by the nucleotide position at which the variation exists, by the change in amino acid sequence caused by the nucleotide variation, or by a change in some other characteristic of the nucleic acid molecule or protein that is linked to the variation.

In the instant application "polymorphism" refers a traditional definition, in that the definition "polymorphism" means that the minor allele frequency must be greater than at least 1%.

A "single nucleotide polymorphism (SNP)" is a single base (nucleotide) polymorphism in a DNA sequence among individuals in a population. Typically in the literature, a single nucleotide polymorphism (SNP) may fall within coding sequences of genes, non-coding regions of genes, or in the intergenic regions between genes. SNPs within a coding sequence will not necessarily change the amino acid sequence of the protein that is produced, due to degeneracy of the genetic code. A SNP in which both forms lead to the same polypeptide sequence is termed "synonymous" (sometimes called a silent mutation)—if a different polypeptide sequence is produced they are "nonsynonymous". A nonsynonymous change may either be missense or "nonsense", where a missense change results in a different amino acid, while a nonsense change results in a premature stop codon.

A tag SNP is a SNP that by itself or in combination with additional Tag SNPs indicates the presence of a specific haplotype, or of one member of a group of haplotypes. The haplotype or haplotypes can indicate a genetic factor is associated with risk for disease, thus a tag SNP or combination of tag SNPs indicates the presence or absence of risk factors for disease. A "tag SNP" is a representative single nucleotide polymorphism (SNP) in a region of the genome with high linkage disequilibrium (the non-random association of alleles at two or more loci) that is associated with a disease, such as renal disease, for example FSGS or ESKD. A tag SNP can be used to identify other SNPs, such as those with a specified $r^2$ value from the tag SNP, which are associated with a disease, such as FSGS or ESKD. Statistical methods to identify a tag SNP are known (see Hoperin et al., Bioinformatics 21 (suppl): i195-i203, 2005, herein incorporated by reference). In the instant disclosure the term "detecting the presence of at least one tag SNP in a non-coding region of a MYH9 gene" means, and is interchangeable with, "detecting the presence of a risk allele of a tag SNP in a non-coding region of a MYH9 gene".

Probes and primers: A probe comprises an isolated nucleic acid capable of hybridizing to a target nucleic acid. A detectable label or reporter molecule can be attached to a probe or primer. Typical labels include radioactive isotopes, enzyme substrates, co-factors, ligands, chemiluminescent or fluorescent agents, haptens, and enzymes. Methods for labeling and guidance in the choice of labels appropriate for various purposes are discussed, for example in Sambrook et al. (In *Molecular Cloning: A Laboratory Manual*, CSHL, New York, 1989) and Ausubel et al. (In *Current Protocols in Molecular Biology*, John Wiley & Sons, New York, 1998).

In a particular example, a probe includes at least one fluorophore, such as an acceptor fluorophore or donor fluorophore. For example, a fluorophore can be attached at the 5'- or 3'-end of the probe. In specific examples, the fluorophore is attached to the base at the 5'-end of the probe, the base at its 3'-end, the phosphate group at its 5'-end or a modified base, such as a T internal to the probe.

Probes are generally at least 15 nucleotides in length, such as at least 15, at least 16, at least 17, at least 18, at least 19, least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50 at least 51, at least 52, at least 53, at least 54, at least 55, at least 56, at least 57, at least 58, at least 59, at least 60, at least 61, at least 62, at least 63, at least 64, at least 65, at least 66, at least 67, at least 68, at least 69, at least 70, or more contiguous nucleotides complementary to the target nucleic acid molecule, such as 20-70 nucleotides, 20-60 nucleotides, 20-50 nucleotides, 20-40 nucleotides, or 20-30 nucleotides.

Primers are short nucleic acid molecules, for instance DNA oligonucleotides are 10 nucleotides or more in length, which can be annealed to a complementary target nucleic acid molecule by nucleic acid hybridization to form a hybrid between the primer and the target nucleic acid strand. A primer can be extended along the target nucleic acid molecule by a polymerase enzyme. Therefore, primers can be used to amplify a target nucleic acid molecule.

The specificity of a primer increases with its length. Thus, for example, a primer that includes 30 consecutive nucleotides will anneal to a target sequence with a higher specificity than a corresponding primer of only 15 nucleotides. Thus, to obtain greater specificity, probes and primers can be selected that include at least 15, 20, 25, 30, 35, 40, 45, 50, 55, 60, 65, 70 or more consecutive nucleotides. In particular examples, a primer is at least 15 nucleotides in length, such as at least 15 contiguous nucleotides complementary to a target nucleic acid molecule. Particular lengths of primers that can be used to practice the methods of the present disclosure include primers having at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 45, at least 50, at least 55, at least 60, at least 65, at least 70, or more contiguous nucleotides complementary to the target nucleic acid molecule to be amplified, such as a primer of 15-70 nucleotides, 15-60 nucleotides, 15-50 nucleotides, or 15-30 nucleotides.

Primer pairs can be used for amplification of a nucleic acid sequence, for example, by PCR, real-time PCR, or other nucleic-acid amplification methods known in the art. An "upstream" or "forward" primer is a primer 5' to a reference point on a nucleic acid sequence. A "downstream" or "reverse" primer is a primer 3' to a reference point on a nucleic acid sequence. In general, at least one forward and one reverse primer are included in an amplification reaction.

Nucleic acid probes and primers can be readily prepared based on the nucleic acid molecules provided herein. It is also appropriate to generate probes and primers based on fragments or portions of these disclosed nucleic acid molecules, for instance regions that encompass the identified polymorphisms of interest. PCR primer pairs can be derived from a known sequence by using computer programs intended for that purpose such as Primer (Version 0.5, © 1991, Whitehead Institute for Biomedical Research, Cambridge, Mass.) or PRIMER EXPRESS® Software (Applied Biosystems, AB, Foster City, Calif.).

Recessive Model: A genetic based model that tests the association of having at least two minor alleles (e.g. DD) versus having at least one major allele (e.g., Dd or dd).

Renal Disease (Nephropathy): A disorder that specifically leads to damage of the kidneys. Renal diseases include FSGS, hypertensive end-stage kidney disease, nephropathy secondary to systemic lupus erythematosus, diabetic nephropathy, hypertensive nephropathy, IgA nephropathy, nephritis or xanthine oxidase deficiency.

Renal disease can be chronic or acute. Chronic renal disease, or the type detected with the assays disclosed herein can progress from stage 1 to stage 2, stage 3, stage 4 or stage 5. The stages of chronic renal disease are:

Stage 1: Slightly diminished kidney function; Kidney damage with normal or increased GFR (>90 mL/min/1.73 m2). Kidney damage is defined as pathologic abnormalities or markers of damage, including abnormalities in blood or urine test or imaging studies.

Stage 2: Mild reduction in GFR (60-89 mL/min/1.73 m2) with kidney damage. Kidney damage is defined as pathologic abnormalities or markers of damage, including abnormalities in blood or urine test or imaging studies.

Stage 3: Moderate reduction in GFR (30-59 mL/min/1.73 m2)

Stage 4: Severe reduction in GFR (15-29 mL/min/1.73 m2)

Stage 5: Established kidney failure (GFR<15 mL/min/1.73 m2, or permanent renal replacement therapy (RRT)

The disclosed assays can be used to detect renal disease, such as FSGS, at any of these stages, or prior to stage 1.

Risk Allele: A "risk" allele is an allele associated with a particular type or form of disease. The risk allele identifies a tag single nucleotide polymorphism that can be used to detect or determine the risk for a disease, such as FSGS or hypertensive end stage kidney disease.

Hypertensive nephropathy (or "hypertensive nephrosclerosis", or "Hypertensive renal disease" or "hypertensive kidney disease"): A medical condition referring to damage to the kidney due to chronic high blood pressure. In the kidneys, as a result of benign arterial hypertension, hyaline (pink, amorphous, homogeneous material) accumulates in the wall of small arteries and arterioles, producing the thickening of their walls and the narrowing of the lumens—hyaline arteriolosclerosis. Consequent ischemia produces tubular atrophy, interstitial fibrosis, glomerular alterations (smaller glomeruli with different degrees of hyalinization—from mild to sclerosis of glomeruli) and periglomerular fibrosis. In advanced stages ("end-stage"), renal failure will occur.

Sample: A sample, such as a biological sample, is a sample obtained from a subject. As used herein, biological samples include all clinical samples useful for detection of renal disease in subjects, including, but not limited to, cells, tissues, and bodily fluids, such as: blood; derivatives and fractions of blood, such as serum; extracted galls; biopsied or surgically removed tissue, including tissues that are, for example, unfixed, frozen, fixed in formalin and/or embedded in paraffin; tears; milk; skin scrapes; surface washings; urine; sputum; cerebrospinal fluid; prostate fluid; pus; or bone marrow aspirates. In a particular example, a sample includes blood obtained from a human subject, such as whole blood or serum. In another particular example, a sample includes buccal cells, for example collected using a swab or by an oral rinse.

Sequence identity/similarity: The identity/similarity between two or more nucleic acid sequences, or two or more amino acid sequences, is expressed in terms of the identity or similarity between the sequences. Sequence identity can be measured in terms of percentage identity; the higher the percentage, the more identical the sequences are. Sequence similarity can be measured in terms of percentage similarity (which takes into account conservative amino acid substitutions); the higher the percentage, the more similar the sequences are. Homologs or orthologs of nucleic acid or amino acid sequences possess a relatively high degree of sequence identity/similarity when aligned using standard methods. This homology is more significant when the orthologous proteins or cDNAs are derived from species which are more closely related (such as human and mouse sequences), compared to species more distantly related (such as human and C. elegans sequences).

Methods of alignment of sequences for comparison are well known in the art. Various programs and alignment algorithms are described in: Smith & Waterman, *Adv. Appl. Math.* 2:482, 1981; Needleman & Wunsch, *J. Mol. Biol.* 48:443, 1970; Pearson & Lipman, *Proc. Natl. Acad. Sci. USA* 85:2444, 1988; Higgins & Sharp, *Gene,* 73:237-44, 1988; Higgins & Sharp, *CABIOS* 5:151-3, 1989; Corpet et al., *Nuc. Acids Res.* 16:10881-90, 1988; Huang et al. *Computer Appls. in the Biosciences* 8, 155-65, 1992; and Pearson et al., *Meth. Mol. Bio.* 24:307-31, 1994. Altschul et al., *J. Mol. Biol.* 215: 403-10, 1990, presents a detailed consideration of sequence alignment methods and homology calculations.

The NCBI Basic Local Alignment Search Tool (BLAST) (Altschul et al., *J. Mol. Biol.* 215:403-10, 1990) is available from several sources, including the National Center for Biological Information (NCBI, National Library of Medicine, Building 38A, Room 8N805, Bethesda, Md. 20894) and on the Internet, for use in connection with the sequence analysis programs blastp, blastn, blastx, tblastn and tblastx. Additional information can be found at the NCBI web site.

BLASTN is used to compare nucleic acid sequences, while BLASTP is used to compare amino acid sequences. To compare two nucleic acid sequences, the options can be set as follows: -i is set to a file containing the first nucleic acid sequence to be compared (such as C:\seq1.txt); -j is set to a file containing the second nucleic acid sequence to be compared (such as C:\seq2.txt); -p is set to blastn; -o is set to any desired file name (such as C:\output.txt); -q is set to −1; -r is set to 2; and all other options are left at their default setting. For example, the following command can be used to generate an output file containing a comparison between two sequences: C:\Bl2seq -i c:\seq1.txt -j c:\seq2.txt -p blastn -o c:\output.txt -q -1 -r 2.

To compare two amino acid sequences, the options of Bl2seq can be set as follows: -i is set to a file containing the first amino acid sequence to be compared (such as C:\seq1.txt); -j is set to a file containing the second amino acid sequence to be compared (such as C:\seq2.txt); -p is set to blastp; -o is set to any desired file name (such as C:\output-.txt); and all other options are left at their default setting. For example, the following command can be used to generate an output file containing a comparison between two amino acid sequences: C:\Bl2seq -i c:\seq1.txt -j c:\seq2.txt -p blastp -o c:\output.txt. If the two compared sequences share homology, then the designated output file will present those regions of homology as aligned sequences. If the two compared sequences do not share homology, then the designated output file will not present aligned sequences.

Once aligned, the number of matches is determined by counting the number of positions where an identical nucleotide or amino acid residue is presented in both sequences. The percent sequence identity is determined by dividing the number of matches either by the length of the sequence set forth in the identified sequence, or by an articulated length (such as 100 consecutive nucleotides or amino acid residues from a sequence set forth in an identified sequence), followed by multiplying the resulting value by 100. For example, a nucleic acid sequence that has 1166 matches when aligned with a test sequence having 1154 nucleotides is 75.0 percent identical to the test sequence (i.e., 1166÷1554*100=75.0). The percent sequence identity value is rounded to the nearest tenth. For example, 75.11, 75.12, 75.13, and 75.14 are rounded down to 75.1, while 75.15, 75.16, 75.17, 75.18, and 75.19 are rounded up to 75.2. The length value will always be an integer. In another example, a target sequence containing a 20-nucleotide region that aligns with 20 consecutive nucleotides from an identified sequence as follows contains a region that shares 75 percent sequence identity to that identified sequence (that is, 15÷20*100=75).

One indication that two nucleic acid molecules are closely related is that the two molecules hybridize to each other under stringent conditions, as described above. Nucleic acid sequences that do not show a high degree of identity may nevertheless encode identical or similar (conserved) amino acid sequences, due to the degeneracy of the genetic code. Changes in a nucleic acid sequence can be made using this degeneracy to produce multiple nucleic acid molecules that all encode substantially the same protein. Such homologous nucleic acid sequences can, for example, possess at least 60%, at least 70%, at least 80%, at least 90%, at least 95%, at least 98%, or at least 99% sequence identity determined by this method. An alternative (and not necessarily cumulative)

indication that two nucleic acid sequences are substantially identical is that the polypeptide which the first nucleic acid encodes is immunologically cross reactive with the polypeptide encoded by the second nucleic acid. One of skill in the art will appreciate that the particular sequence identity ranges are provided for guidance only.

Subject: Living multi-cellular vertebrate organisms, a category that includes human and non-human mammals (such as laboratory or veterinary subjects).

Therapeutically effective amount: An amount of a therapeutic agent that alone, or together with one or more additional therapeutic agents, induces the desired response, such as decreasing the risk of developing FSGS or decreasing the signs and symptoms of FSGS. Ideally, a therapeutically effective amount provides a therapeutic effect without causing a substantial cytotoxic effect in the subject. The preparations disclosed herein are administered in therapeutically effective amounts.

In one example, a desired response is to prevent the development of FSGS. In another example, a desired response is to delay the development or progression of FSGS, for example, by at least about three months, at least about six months, at least about one year, at least about two years, at least about five years, or at least about ten years. In another example, a desired response is to decrease the signs and symptoms of FSGS, such as the neurological symptoms in the limbs or associated with speaking. In general, a therapeutically effective amount of a composition administered to a human subject will vary depending upon a number of factors associated with that subject, for example the overall health of the subject, the condition to be treated, or the severity of the condition. A therapeutically effective amount of a composition can be determined by varying the dosage of the product and measuring the resulting therapeutic response. The therapeutically effective amount can be dependent on the source applied, the subject being treated, the severity and type of the condition being treated, and the manner of administration.

Reference Allele: A genotype that predominates in a natural population of organisms that do not have a disease process, such as renal disease, for example FSGS. The reference genotype differs from mutant forms.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The term "comprises" means "includes." All publications, patent applications, patents, and other references mentioned herein are incorporated by reference in their entirety. In case of conflict, the present specification, including explanations of terms, will control. In addition, the materials, methods, and examples are illustrative only and not intended to be limiting.

Methods for Detecting a Genetic Predisposition to Renal Disease

Methods for determining the genetic predisposition of a subject to renal disease are provided herein. Disclosed herein are methods for determining the genetic predisposition to FSGS, as well as methods for determining the genetic predisposition of a subject to hypertensive end-stage kidney disease. However, the methods disclosed herein also can be used to detect any form of renal disease, such as, but not limited to, FSGS or hypertensive end-stage kidney disease. The methods also can be used to determine the risk of developing renal disease. The methods are also useful in genetic confirmations of a diagnosis of renal disease, or to determine a therapeutic regimen for a subject. The methods are useful not only in determining risk, but for genetic confirmation of suspected chronic renal disease, for example a subject who presents with a reduced glomerular filtration rate (GFR) or other laboratory evidence of renal impairment (such as elevated blood urea nitrogen (BUN) or abnormal renal histology), or someone with clinical presentation (symptoms) of renal disease, such as fatigue and liquid retention. The methods disclosed herein can be used to determine the genetic predisposition, detect, or determine the risk of developing nephropathy secondary to systemic lupus erythematosus and other nephropathies.

In some embodiments, the method includes detecting the presence of a genotype, such that both alleles of the genotype of the subject are risk alleles of a tag SNP. In other embodiments, the method includes detecting the presence of a genotype, such that one of the alleles of the genotype is a risk allele of a tag SNP.

In some embodiments, the method uses two or more tag SNPs to identify the presence in the genome of a subject of one or two risk haplotypes. In some embodiments, both of the haplotypes identified as carried by the subject are copies of a risk haplotype. In other embodiments, one of the haplotypes is a risk haplotype.

In some embodiments, the method includes detecting the presence of a genotype, such that both alleles of the genotype of the subject are a haplotype that includes at least two tag SNPs. In another embodiment, at least one SNP is present in the non-coding region of a gene of interest, for example, MYH9. Thus, two copies of the tag SNP are present in the genome of the subject. In other embodiments, the single allele is detected such that either of the alleles of the subject includes the tag SNP. Thus, the disclosed methods include detecting one or two copies of the tag SNP in the genome of the subject. In a further embodiment, the presence of a single allele is detected in a non-coding region of a gene of interest, such that either of the alleles of the subject includes a tag SNP.

In some embodiments, the methods disclosed herein can be used to determine the genetic predisposition of a human subject to renal disease, wherein the subject is of African ancestry, such as an African-American subject (a subject who is of African ancestry who resides in the United States) or an African-European subject (a subject who is of African ancestry who resides in Europe). In additional embodiments, the methods disclosed herein can be used to determine the genetic predisposition of a human subject to renal disease, wherein the subject is of European ancestry. The human subject can self-identify themselves (such as on a questionnaire) as being of European ancestry, such as identifying themselves as Caucasian. There are a number of programs available to confirm European ancestry, if such confirmation is desired. These include the program STRUCTURE™ (version 2.2, available on the University of Chicago website on Jan. 28, 2009) and the program EURASIANDNA™, version 1.0 and 2.0 (available from DNAPRINT™). In other embodiments, the subject can self-identify themselves (such as on a questionnaire) as being of a specific ancestry. However, there are a number of programs available to confirm ancestry, if such confirmation is desired. These include the program STRUCTURE™ (version 2.2, available on the University of Chicago website on Jan. 28, 2009). In several examples, the subject is infected with a human immunodeficiency virus, such as HIV-1 or HIV-2.

As noted above, the methods are useful not only in determining risk, but also can be used for genetic confirmation of suspected renal disease, for example a subject who presents with a reduced glomerular filtration rate (GFR) or other laboratory evidence of renal impairment (such as elevated blood urea nitrogen (BUN) or abnormal renal histology), or an individual, such as an individual of African or European ancestry, with clinical presentation (symptoms) of renal disease, such as fatigue and liquid retention. The methods are also of use for determining a therapeutic regimen of use in treating a subject of interest, or determining if a subject will benefit from treatment with a therapeutic regimen of interest.

In some embodiments, the methods include obtaining a sample including nucleic acids from a human subject of interest, and analyzing the sample for the presence of a haplotype including a tag SNP in these nucleic acids. In other embodiments, a sample is obtained that contains nucleic acids from a human subject of interest, and the sample is analyzed for the presence of a haplotype including at least two tag SNPs in a non-coding region of a gene of interest. The methods can include selecting a subject in need of detecting the presence of the haplotype, and obtaining a sample including nucleic acids from this subject. For example, a subject can be selected who is suspected to possess a genetic predisposition to renal disease, such as FSGS or hypertensive end-stage kidney disease. In another example, a subject can be selected that is of African ancestry and/or is infected with HIV. In a further example, a subject can be selected who has renal disease, such as, but not limited to FSGS or hypertensive end-stage kidney disease. Thus, the subject's risk for progressing to another stage of renal disease can be detected. The methods disclosed herein can also be used to confirm the presence of renal disease in the subject. In yet another example, a subject with renal disease is selected to determine if a particular therapeutic regimen is appropriate for the subject. A subject of interest can also be selected to determine if preventative or prophylactic treatment should be undertaken.

Biological samples include all clinical samples useful for detection of renal disease in subjects, such as cells, tissues, and bodily fluids, for example blood; derivatives and fractions of blood, such as serum; extracted galls; biopsied or surgically removed tissue, including tissues that are, for example, unfixed, frozen, fixed in formalin and/or embedded in paraffin; tears; milk; skin scrapes; surface washings; urine; sputum; cerebrospinal fluid; prostate fluid; pus; or bone marrow aspirates. In a particular example, a sample includes blood obtained from a human subject, such as whole blood or serum. In another particular example, a sample includes buccal cells, for example collected using a swab or by an oral rinse. In additional embodiments, the method includes analyzing DNA sequence data previously obtained from the subject of interest.

Generally, the methods utilize the detection of one or more haplotype(s) comprising at least two tag SNPs in a non-coding region of a gene of interest, for example MYH9. In several embodiments, the methods include detecting the presence of one or more tag SNPs or the risk allele associated with a tag SNP. In other embodiments, the methods include detecting the presence of at least two tag SNPs in a non-coding region of the gene under investigation. In some embodiments, identifying the presence of one or more tag SNPs, or haplotype blocks including these SNPs in a non-coding region of a gene of interest, determines if a therapeutic agent can be used for treatment of the subject. Thus, the methods can be used to determine if preventative or prophylactic treatment should be administered to a subject at risk for developing renal disease, or if a treatment should be administered to a subject to prevent the progression of existing renal disease, such as from early stage to a more advanced stage of renal disease. The methods can also be used to confirm a diagnosis of renal disease in the subject.

In one example, a method for detecting a genetic predisposition to renal disease, such as FSGS or hypertensive end-stage kidney disease, in a human subject is performed by detecting the presence of one or more haplotypes including a tag SNP in a non-coding region of a MYH9 gene. Each haplotype is identified by (and includes) a tag SNP. Thus, detecting the presence of the haplotype can include detecting a SNP with $r^2$ value of greater than about 0.75, about 0.8, about 0.85, about 0.9 or about 0.95 from a tag SNP. While it will be appreciated by one of ordinary skill in the art that $r^2$ values for a particular tag SNP may differ between different geographic populations as a result of human migration, it is reasonable to conclude that a strongly associated $r^2$ value is associated with an increased risk for the development of a disease under investigation, such as FSGS.

In another example, a method for detecting a genetic predisposition to renal disease, such as FSGS or hypertensive end-stage kidney disease, in a human subject can be determined by detecting the presence of one or two haplotypes including at least two tag SNPs in a non-coding region of a gene of interest, such as MYH9. Each haplotype is identified by (and includes) at least two tag SNPs in the non-coding region of the gene of interest. Thus, detecting the presence of the haplotype can include detecting at least one SNP with a $r^2$ value of greater than about 0.75, about 0.8, about 0.85, about 0.9 or about 0.95 from a tag SNP.

In one example, specific haplotypes of use to identify a genetic predisposition to renal disease, such as FSGS or hypertensive end stage kidney disease in a subject of African ancestry, such as an African American subject, include the following tag SNPs: a G at rs4821480; a C at rs4821481; an A at rs1005570; a C at rs2032487; an A at rs5756152; an A it rs16996677; a T at rs3752462; a T at rs16996674; a C at rs735853; a T at rs5756129; a G at rs12107; an A at rs7078; a C at rs5756130; an A at rs9619601; a T at rs875725 and combinations thereof.

In another example, specific haplotypes of use to identify a genetic predisposition to renal disease, such as FSGS or hypertensive end stage kidney disease in a subject of African ancestry, such as an African American subject, include the following tag SNPs in a non-coding region of the gene of interest: a G at rs5750250; a T at rs5750248; a C at rs2413396; a A at rs11912763; a G at rs4821480; a C at rs4821481; an A at rs2157256; an A at rs1005570; a C at rs2032487; an A at rs5756152; an A at rs1557529; a T at rs2239784; a C at rs16996648; a T at rs735854; an A at rs16996677; a T at rs3752462; a C at rs4821484; a G at rs8143119; a T at rs16996674; a T at rs5756157; an A at rs136196; an A at rs2157257; a C at rs735853; a G at rs739096; a G at rs739101; a C at rs1009150; an A at rs8141189; a G at rs2071733; a T at rs5756133; a T at rs5756129; an A at rs136206; an A at rs136213; a G at rs9610498; an A at rs1557538; a C at rs1557536; a G at rs1883273; a C at rs2239783; a C at rs12107; a T at rs7078 and combinations thereof.

In one example, specific haplotypes of use to identify a genetic predisposition to renal disease, such as FSGS or hypertensive end stage kidney disease in a subject of African ancestry, such as an African American subject, include the following tag SNPs in a non-coding region of the gene of interest: a C at rs9622373; a C at rs5756130; an A at rs6000251; a G at rs2071731; a G at rs12159211; an A at rs9619601; a C at rs2071732; a G at rs2272827; a G at rs6000254; a T at rs875725; a T at rs8135022; a T at rs8138583; a G at rs17806513; a C at rs5756168; an A at rs8137674; a T at rs5995283 and combinations thereof.

In other examples, the haplotype includes one, two, three, four, five, six, seven, eight, nine, ten, eleven, twelve, thirteen, fourteen or fifteen tag SNPs. The haplotype can be detected in both alleles (on both chromosomes) of the DNA of the subject of interest.

The presence of the haplotype determines the genetic predisposition to renal disease in the human subject. In some embodiments, the method includes detecting the presence of a haplotype including at least two, at least three, at least four, at least five, at least ten or at least fifteen different tag SNPs. In further embodiments, the method includes detecting the presence of a haplotype including at least two, at least three, at least four, at least five, at least ten or at least fifteen different tag SNPs in the non-coding region of the gene of interest.

The method can also include detecting one of more of the tag SNPs themselves. Thus, the method can include detecting at least one, at least two, at least three, at least four, at least five, at least six, at least seven, at least eight, at least nine, at least ten, at least eleven, at least twelve, at least thirteen, at least fourteen, or at least fifteen different tag SNPs. In some embodiments, the groups of tag SNPs can be in any combination, of at least two, at least three, at least four, at least five, at least ten or at least fifteen different tag SNPs. Detection of all of the tag SNPs disclosed herein can also be used to detect a genetic predisposition to renal disease, such as FSGS or hypertensive end-stage kidney disease.

In one embodiment, the method can include detecting at least one tag SNP in a non-coding region of a gene of interest. Thus, the method can include detecting at least one, at least two, at least three, at least four, at least five, at least six, at least seven, at least eight, at least nine, at least ten, at least eleven, at least twelve, at least thirteen, at least fourteen, or at least fifteen different tag SNPs in the non-coding region of the gene(s) under investigation. In some embodiments, the groups of tag SNPs can be in any combination, of at least two, at least three, at least four, at least five, at least ten or at least fifteen different tag SNPs. Detection of all of the tag SNPs can also be used to detect a genetic predisposition to renal disease, such as FSGS or hypertensive end-stage kidney disease.

With regard to the SNPs, the SNPs can be identified by name. The exact sequence of the SNP can be determined from the database of SNPs available at the NCBI website (Entrez SNP, dbSNP build 128, Jan. 28, 2009). The "position" of the nucleotide of interest is the location in the genome of the SNP, referring to the nucleotide position from the p-terminus of the chromosome in the human genome, see the NCBI SNP website, available on the internet. Sequence information for each of the tag SNPs listed above is provided in the following tables.

TABLE 4 tag single nucleotide polymorphisms (SNPs)

| SNP | risk allele | protective allele | flanking sequence |
|---|---|---|---|
| rs4821480 | G | T | ATTTTCCTAGATCAAAGGATAATTTT[G/T]AA AGGTCACGAGCTCCCCTGAAACA (SEQ ID NO: 1) |
| rs4821481 | C | T | CTCACGGCTGGCAAAGAAGAGCTTTC[C/T]AG AGGGGAAAGGACAAACCCTTCCC (SEQ ID NO: 2) |
| rs1005570 | A | G | TAATTTCAAGATCTCGACATAGTCAC[A/G]GG CAAGGCTCCCATTAAGGAGGAGC (SEQ ID NO: 3) |
| rs2032487 | C | T | AGAGGCTGCCACACGGCGCTCACCTG[C/T]GC CACCAGGCCACCTTCTCCGTGCC (SEQ ID NO: 4) |
| rs5756152 | A | G | AGGAGATGGCCAACTCAGATCGATGC[A/G]G GACCATGAGAAGCAGGGTTCTTAA (SEQ ID NO: 5) |
| rs16996677 | A | G | GGATGGAAGGAAATGGTGTTCCTGTC[A/G]TA CACGGTGTGAGGCAGATGCCCAG (SEQ ID NO: 6) |
| rs3752462 | T | C | CAGGTGTGAGGTCAAAGCAAGCCTGG[C/T]A CTCACTGGCTTCTCAATGAGGTCG (SEQ ID NO: 7) |
| rs16996674 | T | C | GCAACCAGTGGGCTCTTTGGCCTACT[C/T]AG TTTACTCTGCAGCCCACCTCCCC (SEQ ID NO: 8) |
| rs735853 | C | G | ACAGGTGTGCCTGTTCACACAGAGTA[C/G]AA AGACAGGCACCCTCTTTCTACCA (SEQ ID NO: 9) |
| rs5756129 | T | C | TTTATGTACCCAGTCATACACCGTTT[C/T]GC AAGTTTGCTGTTGGACTATCATG (SEQ ID NO: 10) |

TABLE 4-continued tag single nucleotide polymorphisms (SNPs)

| SNP | risk allele | protective allele | flanking sequence |
|---|---|---|---|
| rs12107 | G | A | GCCTGCCTCTGCCACAGCAAGGCTGT[C/T]G GGGTCAAGCTGGAAAGGCCAGCAG (SEQ ID NO: 11) |
| rs7078 | A | G | CCCAACACTCTTGGGGACCAAATATA[C/T]T TAATGGTTAAGGGACTTGTCCCAA (SEQ ID NO: 12) |
| rs5756130 | C | T | TTCCGCAGCTGTTTGATGGCTTCGTC[C/T]CG GTTCTTGTTGGCCGAGTCGATGT (SEQ ID NO: 13) |
| rs9619601 | A | G | ACTTTGCTCTGGCCAATGCGGTACAG[A/G]T TGCTGTCGAGCTCCAGGGCTTTTA (SEQ ID NO: 14) |
| rs875725 | T | C | CGCTCAGACTCCAGGTCTTCCTGGAG[C/T]TC AGAGATCTGAGATTCCAGCTCCC (SEQ ID NO: 15) |
| rs7078 | A | G | CCCAACACTCTTGGGGACCAAATATA[C/T]TT AA TGGTTAAGGGACTTGTCCCAA (SEQ ID NO: 16) |
| rs12107 | G | A | GCCTGCCTCTGCCACAGCAAGGCTGT[C/T]G GGG TCAAGCTGGAAAGGCCAGCAG (SEQ ID NO: 17) |
| rs735853 | C | G | ACAGGTGTGCCTGTTCACACAGAGTA[C/G]A AAG ACAGGCACCCTCTTTCTACCA (SEQ ID NO: 18) |
| rs5756129 | T | C | TTTATGTACCCAGTCATACACCGTTT[C/T]GC AAG TTTGCTGTTGGACTATCATG (SEQ ID NO: 19) |
| rs5756130 | C | T | TTCCGCAGCTGTTTGATGGCTTCGTC[C/T]CG GT TCTTGTTGGCCGAGTCGATGT (SEQ ID NO: 20 |
| rs11549907 | A | G | AAGGATGATGTGGGCAAGAGTGTCCA[C/T]G AGC TGGAGAAGTCCAAGCGGGCCC (SEQ ID NO: 21) |
| rs875725 | T | C | CGCTCAGACTCCAGGTCTTCCTGGAG[C/T]TC AG AGATCTGAGATTCCAGCTCCC (SEQ ID NO: 22) |
| rs2187776 | T | C | CCTCAAAGCATGACTCGCCCGGAAAT[C/T]T GGG GCTGAATGGAGAGGGCTTTAG (SEQ ID NO: 23) |
| rs4821480 | G | T | ATTTTCCTAGATCAAAGGATAATTTT[G/T]AA AG GTCACGAGCTCCCCTGAAACA (SEQ ID NO: 24) |
| rs2032487 | C | T | AGAGGCTGCCACACGGCGCTCACCTG[C/T]G CCA CCAGGCCACCTTCTCCGTGCC (SEQ ID NO: 25) |
| rs4821481 | C | T | CTCACGGCTGGCAAAGAAGAGCTTTC[C/T]A GAG GGGAAAGGACAAACCCTTCCC (SEQ ID NO: 26) |

TABLE 4-continued tag single nucleotide polymorphisms (SNPs)

| SNP | risk allele | protective allele | flanking sequence |
|---|---|---|---|
| rs9619601 | A | G | ACTTTGCTCTGGCCAATGCGGTACAG[A/G]TTGC TGTCGAGCTCCAGGGCTTTTA (SEQ ID NO: 27) |
| rs3752462 | T | C | CAGGTGTGAGGTCAAAGCAAGCCTGG[C/T]ACTC ACTGGCTTCTCAATGAGGTCG (SEQ ID NO: 28) |
| rs5756152 | A | G | AGGAGATGGCCAACTCAGATCGATGC[A/G]GGAC CATGAGAAGCAGGGTTCTTAA (SEQ ID NO: 29) |
| rs1557539 | C | G | TGAAGCTTCTCCAGTGCTCTAGATGG[C/G]GTTA TGCCACCTCTCTCCGGGTTGC (SEQ ID NO: 30) |
| rs1005570 | A | G | TAATTTCAAGATCTCGACATAGTCAC[A/G]GGCA AGGCTCCCATTAAGGAGGAGC (SEQ ID NO: 31) |
| rs16996674 | T | C | GCAACCAGTGGGCTCTTTGGCCTACT[C/T]AGTT TACTCTGCAGCCCACCTCCCC (SEQ ID NO: 32) |
| rs16996677 | A | G | GGATGGAAGGAAATGGTGTTCCTGTC[A/G]TACA CGGTGTGAGGCAGATGCCCAG (SEQ ID NO: 33) |

In additional embodiments, sequence information for the tag SNPs is provided in the following table (Table 5):

TABLE 5 tag single nucleotide polymorphisms (SNPs)

| SNP | risk allele | protective allele | flanking sequence |
|---|---|---|---|
| rs5750250 | G | A | CTGACACCTTTACCCAAGGATCCATC[A/G]CGGTGGTTCTCCAGCATTAGTGAAA (SEQ ID NO: 34) |
| rs5750248 | T | C | TCTCTTGGGGAGCCATGCATCTGCCA[C/T]GGCCACCTCACCTTCCTGTCACCTA (SEQ ID NO: 35) |
| rs2413396 | C | T | AGATCTGGCCAGCACCTCCCCGTGAG[C/T]GCTCCTCACCTTGCCGGCATAGTGG (SEQ ID NO: 36) |
| rs11912763 | A | G | TGGAAGGAGAGAACAGAAGCCTGCGT[A/G]AAGCCAAGGCAGCCTTGGGCACCCA (SEQ ID NO: 37) |
| rs4821480 | G | T | ATTTTCCTAGATCAAAGGATAATTTT[G/T]AAAGGTCACGAGCTCCCCTGAAACA (SEQ ID NO: 38) |
| rs4821481 | C | T | CTCACGGCTGGCAAAGAAGAGCTTTC[C/T]AGAGGGGAAAGGACAAACCCTTCCC (SEQ ID NO: 39) |
| rs2157256 | A | G | GGGCCTCAAGAGCTTGTTTAATCCAC[A/G]TAATCCTGTATGGTGGGTGGTCATT (SEQ ID NO: 40) |

TABLE 5-continued tag single nucleotide polymorphisms (SNPs)

| SNP | risk allele | protective allele | flanking sequence |
|---|---|---|---|
| rs1005570 | A | G | TAATTTCAAGATCTCGACATAGTCAC[A/G]G GCAAGGCTCCCATTAAGGAGGAGC (SEQ ID NO: 41) |
| rs2032487 | C | T | AGAGGCTGCCACACGGCGCTCACCTG[C/T]G CCACCAGGCCACCTTCTCCGTGCC (SEQ ID NO: 42) |
| rs5756152 | A | G | AGGAGATGGCCAACTCAGATCGATGC[A/G] GGACCATGAGAAGCAGGGTTCTTAA (SEQ ID NO: 43) |
| rs1557529 | A | G | CTCCGGAGCACAGGCTAACCCCATGC[A/G]T GGAAAAGTCAGAAAACGTGAAGAC (SEQ ID NO: 44) |
| rs2239784 | T | C | GGCAGCTGTACCTCCCCTGAGCCCCA[C/T]G GGGCAGAGAGGAAGGCGTCCTGGC (SEQ ID NO: 45) |
| rs16996648 | C | T | CCCTGAGTGCACAAGAACTGTTTTGC[C/T]A TGAAATAAATGGCTCTTTTAAGAC (SEQ ID NO: 46) |
| rs735854 | T | C | GCAAAATGTTTAGGTGTCGGACATCT[C/T]C ACACACAACAGTAGCACAAAAACA (SEQ ID NO: 47) |
| rs16996677 | A | G | GGATGGAAGGAAATGGTGTTCCTGTC[A/G]T ACACGGTGTGAGGCAGATGCCCAG (SEQ ID NO: 48) |
| rs3752462 | T | C | CAGGTGTGAGGTCAAAGCAAGCCTGG[C/T] ACTCACTGGCTTCTCAATGAGGTCG (SEQ ID NO: 49) |
| rs4821484 | C | A | TAGAGCCCGGATGCTCCTGGCCTTCC[A/C]T TTATCCACCCAGCAGTGGGCAACA (SEQ ID NO: 50) |
| rs8143119 | G | T | CAGCTCAGCAGGCTGGGCCCAGGAGG[G/T] AGGAAGGGGAACCTGACCGCAGGTA (SEQ ID NO: 51) |
| rs16996674 | T | C | GCAACCAGTGGGCTCTTTGGCCTACT[C/T]A GTTTACTCTGCAGCCCACCTCCCC (SEQ ID NO: 52) |
| rs5756157 | T | G | CTCACACCTGGCTAGGAGGAGCATCT[G/T]C GGGGGAGAGTGCCATTGGGCAGCT (SEQ ID NO: 53) |
| rs136196 | A | G | ACTTAGCTGCTGTGGAAAACTATATG[A/G]C GGTTCTTTGAAAACTTAAACATAG (SEQ ID NO: 54) |
| rs2157257 | A | G | GGGCACCCCACCCTTCAAGAAGCCAA[A/G] GCCCGGACATCAGAATCCCCTGAAT (SEQ ID NO: 55) |
| rs735853 | C | G | ACAGGTGTGCCTGTTCACACAGAGTA[C/G]A AAGACAGGCACCCTCTTTCTACCA (SEQ ID NO: 56) |
| rs739096 | G | C | TCCTTAGGGACAGGGGCCTTTAATTT[C/G]G TCCACATGATAATCTTATCAAGCa (SEQ ID NO: 57) |
| rs739101 | G | A | ACTCCTCTCAAGGGGCAGGGCTGGGG[A/G] TCCTCAGACAGCCACGGACCTGTGC (SEQ ID NO: 58) |
| rs1009150 | C | T | AGAGGAAGTGCAGGCTGTGAATGTAG[C/T] GTATCTCCTAAGCGAGCCAAGGCC (SEQ ID NO: 59) |

TABLE 5-continued tag single nucleotide polymorphisms (SNPs)

| SNP | risk allele | protective allele | flanking sequence |
|---|---|---|---|
| rs8141189 | A | T | GTTCCTCTGTCCACTCTCAGCCGCAC[A/T]C CTCAGAGTGTAAAAGCAGGTCCCT (SEQ ID NO: 60) |
| rs2071733 | G | C | AACTGGAAAAGAGGTCTGGGGGCCTA[C/G] TGTAAACCCCATTCCCTCCAAGGAA (SEQ ID NO: 61) |
| rs5756133 | T | A | CATATGTGTGCTCTGACAGCTCCGTG[A/T]C TATGTTAGCCCTTATTAGTGTCAA (SEQ ID NO: 62) |
| rs5756129 | T | C | TTTATGTACCCAGTCATACACCGTTT[C/T]G CAAGTTTGCTGTTGGACTATCATG (SEQ ID NO: 63) |
| rs136206 | A | G | GAGCCAAGTTGAAACCACACACGCGT[A/G] AGGGTTATAGCCACCTAATTTGTTA (SEQ ID NO: 64) |
| rs136213 | A | G | GAGGGGCAGATGATCCCCTTTGACTC[A/G]C CCCCAGGTTGGAAGCGGCTGACAG (SEQ ID NO: 65) |
| rs9610498 | G | A | ACGAAGCACCATTTACACTACTTTGC[A/G]T CTGGTGTTTTTCACTTACAACATA (SEQ ID NO: 66) |
| rs1557538 | A | G | AAACTTAGATCTTTTGAAATAAAATG[A/G]G GACACACTAAAGGATTTACAGAAA (SEQ ID NO: 67) |
| rs1557536 | C | G | AGTAATTTCACTTTTAGAGTCCTCCC[C/G]C TAGAGGAACAGCCCTAAGTATGTG (SEQ ID NO: 68) |
| rs1883273 | G | A | GTGAAGTGGCATGTTCCTAGGTCTAC[A/G]C TGCGAGCCCCCTCCAGGACAGGGC (SEQ ID NO: 69) |
| rs2269529 | T | C | GTCCCGGTTCTTGTTGGCCGAGTCGA[C/T]G TGCGCCTCCAGGTCCTTCAGGTCC (SEQ ID NO: 70) |
| rs2239783 | C | T | GCGCTCCGCCCAGGAGGACCCGGCCA[C/T] GGTGTGTGCGCAAGGGCAGTGGCCT (SEQ ID NO: 71) |
| rs12107 | C | T | GCCTGCCTCTGCCACAGCAAGGCTGT[C/T]G GGGTCAAGCTGGAAAGGCCAGCAG (SEQ ID NO: 72) |
| rs7078 | T | C | CCCAACACTCTTGGGGACCAAATATA[C/T]T TAATGGTTAAGGGACTTGTCCCAA (SEQ ID NO: 73) |

In these tables, the "risk" allele identifies the tag SNP that can be used to detect or determine the risk for renal disease, such as FSGS or hypertensive end stage kidney disease. The "reference" allele is a different allele not associated with renal disease, and thus is a "protective allele" as this allele indicates that the subject does not have or is not a risk for developing renal disease, such as FSGS or hypertensive end stage kidney disease. In the sequences provided above, the notation "[X/Y]" is used, wherein one of X or Y is the risk allele and one of X or Y is the reference (protective) allele. For each sequence, the allele associated with renal disease (the "risk" allele) is listed. The allele that is associated with a decreased risk (or absence) of renal disease is also listed (the "protective" allele).

The disclosed methods can include detecting the risk allele on one or both chromosomes, detecting the presence of a protective allele on one or both chromosomes, or detecting the absence of the protective allele on one or both chromosomes. The method can include detecting one or more risk alleles and/or the tag SNPs from at least one of Tables 4 and 5, or Table 6.

TABLE 6 tag single nucleotide polymorphisms.

| SNP | risk | prot | flanking sequence |
|---|---|---|---|
| rs9622373 | C | T | CCATCACGTGATCTTGAGATGTAGCC[C/T]GTGAAGTTTCGCTGGAATAGATGTG (SEQ ID NO: 74) |
| rs5756130 | C | T | TTCCGCAGCTGTTTGATGGCTTCGTC[C/T]CGGTTCTTGTTGGCCGAGTCGATGT (SEQ ID NO: 75) |
| rs6000251 | A | C | CCACTCTGCAAGGACCACCCTGAGAG[A/C]AGGCCGGGCTCAGAATGAGTCAGAG (SEQ ID NO: 76) |
| rs2071731 | G | A | TCAGCTCTAGGAACCTGGCCCTGGAC[A/G]ACCCATGTGAAAGCAGCACTTAAAC (SEQ ID NO: 77) |
| rs12159211 | G | A | CCACTTTGGGCTCCAGGCTGTTTACT[A/G]AGAATGTCAATAAATCCTACTGTGA (SEQ ID NO: 78) |
| rs9619601 | A | G | ACTTTGCTCTGGCCAATGCGGTACAG[A/G]TTGCTGTCGAGCTCCAGGGCTTTTA (SEQ ID NO: 79) |
| rs2071732 | C | T | GACACCTATGTGTACCCGGCTTCTTA[C/T]GACGGGCACTGCAAATAGCCCCATT (SEQ ID NO: 80) |
| rs2272827 | G | A | TGATTAACATGCGTCCTTCATCCTAC[A/G]AGAGAGAAGTTGTCCCATCTCCAAC (SEQ ID NO: 81) |
| rs6000254 | G | A | CACTTCACCCTGGCCAGTCCATTCAA[A/G]CAAATCCAAGGTTTCTCCCTGCCAG (SEQ ID NO: 82) |
| rs875725 | T | C | CGCTCAGACTCCAGGTCTTCCTGGAG[C/T]TCAGAGATCTGAGATTCCAGCTCCC (SEQ ID NO: 83) |
| rs8135022 | T | G | CATTCTGGCACCTTCTGTCACCTACC[G/T]CCACGGCCTAATCCAAGGCACTACA (SEQ ID NO: 84) |
| rs8138583 | T | C | CTGTAAATAAGGAAAGCCCTAAGCTC[C/T]GTGTTGGGTTTGCACTAGCCGATCC (SEQ ID NO: 85) |
| rs17806513 | G | A | TGTTCCCTATCTCCCCGTCACCGAAC[A/G]CAGGCTGTGCACACAGTAGGTGTTG (SEQ ID NO: 86) |
| rs5756168 | C | T | GACGAAGGGAGTAGAAGAATAGACTC[C/T]TAAGGAAAGATTAAAGGAGCTCAGT (SEQ ID NO: 87) |
| rs8137674 | A | G | GATGCGGGTCCAGCTTGCCGGCCTGG[A/G]GAAGAAAACACATGCATGCGGTCTC (SEQ ID NO: 88) |
| rs5995283 | T | C | TCAGGTTCTAAGAGGCCACTTCCTTT[C/T]TATCTCCCGCTCAGTGGGCCCAGAG (SEQ ID NO: 89) |

In some embodiments, detecting the presence of the haplotype (or the tag SNP) of the risk allele indicates that the subject has a genetic predisposition to renal disease, and detecting the absence of the protective allele indicates that the subject has a genetic predisposition to renal disease. Similarly, detecting the absence of the haplotype (and/or tag SNP) of the risk allele indicates that the subject does not have a genetic predisposition to renal disease, and detecting the presence of the protective allele indicates that the subject does not have a genetic predisposition to renal disease.

Thus, the disclosed methods can detect a low risk of developing renal disease, or identify a subject that does not have a genetic pre-disposition to developing renal disease. For example, subjects that have a haplotype associated with the reference allele are not genetically pre-disposed to developing renal disease, such as FSGS or hypertensive end stage kidney disease. These subjects do not have renal disease and/or have a low risk for developing renal disease.

In one embodiment, a haplotype is detected by detecting a single nucleotide polymorphism with an $r^2$ value of about 0.75 or greater from a tag SNP, wherein the tag SNP is a G at rs4821480; a C at rs4821481; an A at rs1005570; a C at rs2032487; an A at rs5756152; an A it rs16996677; a T at rs3752462; a T at rs16996674; a C at rs735853; a T at rs5756129; a G at rs12107; an A at rs7078; a C at rs5756130; an A at rs9619601; a T at rs875725.

Alternatively, a haplotype is detected by detecting at least one tag single nucleotide polymorphism in the non-coding region of the gene of interest, with an $r^2$ value of about 0.75 or greater, wherein the at least one tag SNP is a G at rs5750250; a T at rs5750248; a C at rs2413396; a A at rs11912763; a G at rs4821480; a C at rs4821481; an A at rs2157256; an A at rs1005570; a C at rs2032487; an A at rs5756152; an A at rs1557529; a T at rs2239784; a C at rs16996648; a T at rs735854; an A at rs16996677; a T at rs3752462; a C at rs4821484; a G at rs8143119; a T at rs16996674; a T at rs5756157; an A at rs136196; an A at rs2157257; a C at rs735853; a G at rs739096; a G at rs739101; a C at rs1009150; an A at rs8141189; a G at rs2071733; a T at rs5756133; a T at rs5756129; an A at rs136206; an A at rs136213; a G at rs9610498; an A at rs1557538; a C at rs1557536; a G at rs1883273; a C at rs2239783; a C at rs12107; or a T at rs7078.

In another embodiment, the at least one tag SNP is a C at rs9622373; a C at rs5756130; an A at rs6000251; a G at rs2071731; a G at rs12159211; an A at rs9619601; a C at rs2071732; a G at rs2272827; a G at rs6000254; a T at rs875725; a T at rs8135022; a Tat rs8138583; a G at rs17806513; a C at rs5756168; an A at rs8137674; or a T at rs5995283.

In other embodiments, a single nucleotide polymorphism is detected with an $r^2$ value of 0.75 or greater, 0.8 or greater, 0.85 or greater, 0.9 or greater, or 0.95 or greater, or 0.97 or greater from one or more tag SNPs such as those indicated above. One of skill in the art can readily identify additional single nucleotide polymorphisms with an $r^2$ value of about 0.75 or greater, about 0.85 or greater, about 0.9 or greater, or about 0.95 or greater from one of the tag SNPs of use in the methods disclosed herein.

In some embodiments, the method includes detecting the presence of one or more tag SNPs. Thus, the method can include detecting at least one, at least two, at least three, at least four, at least five, at least ten or at least fifteen different of the tag SNPs themselves, wherein the tag SNPs are an A in rs7078; a G in rs12107; a C in rs735853; a T in rs5756129; a C in rs5756130; a G in rs11549907; a T in rs875725; a C in rs2187776; a G in rs4821480; a C in rs2032487; a C in rs4821481; a Tin rs3752462; an A in rs5756152; a G in rs1557539; an A in rs1005570; a Gin rs16996674; and an A in rs16996677.

In several embodiments, at least one tag SNP is detected in the non-coding region of the MYH9 gene. Thus, the method can include detecting at least one, at least two, at least three, at least four, at least five, at least ten or at least fifteen different tag SNPs in the non-coding region of the gene of interest, wherein at least one or more tag SNPs in the non-coding region of the gene is a G at rs5750250; a T at rs5750248; a C at rs2413396; a A at rs11912763; a G at rs4821480; a C at rs4821481; an A at rs2157256; an A at rs1005570; a C at rs2032487; an A at rs5756152; an A at rs1557529; a T at rs2239784; a C at rs16996648; a T at rs735854; an A at rs16996677; a T at rs3752462; a C at rs4821484; a G at rs8143119; a Tat rs16996674; a T at rs5756157; an A at rs136196; an A at rs2157257; a C at rs735853; a G at rs739096; a G at rs739101; a C at rs1009150; an A at rs8141189; a G at rs2071733; a T at rs5756133; a T at rs5756129; an A at rs136206; an A at rs136213; a G at rs9610498; an A at rs1557538; a C at rs1557536; a G at rs1883273; a C at rs2239783; a C at rs12107; or a T at rs7078.

In another embodiment, the method detects the presence of at least one, at least two, at least three, at least four, at least five, at least ten or at least fifteen different tag SNPs in the non-coding region of the gene of interest, wherein at least one or more tag SNPs in the non-coding region of the gene is a C at rs9622373; a C at rs5756130; an A at rs6000251; a G at rs2071731; a G at rs12159211; an A at rs9619601; a C at rs2071732; a G at rs2272827; a G at rs6000254; a T at rs875725; a T at rs8135022; a Tat rs8138583; a G at rs17806513; a C at rs5756168; an A at rs8137674; or a T at rs5995283.

In one embodiment, the method comprises detecting a haplotype including two tag SNPs, wherein at least one of the two tag SNPs is a G at rs4821480; a C at rs4821481; an A at rs1005570; a C at rs2032487; a T at rs3752462; an A at rs16996674; an A at rs5756152; an A it rs16996677; a C at rs735853; or a T at rs5756129. However, the method can also include detecting more than one of these tag SNPs.

In another embodiment, at least two tag SNPs are detected in the non-coding region of the MYH9 gene, and the at least two tag SNPs are from the group comprising a G at rs5750250; a T at rs5750248; a C at rs2413396; a A at rs11912763; a G at rs4821480; a C at rs4821481; an A at rs2157256; an A at rs1005570; a C at rs2032487; an A at rs5756152; an A at rs1557529; a T at rs2239784; a C at rs16996648; a T at rs735854; an A at rs16996677; a T at rs3752462; a C at rs4821484; a G at rs8143119; a T at rs16996674; a T at rs5756157; an A at rs136196; an A at rs2157257; a C at rs735853; a G at rs739096; a G at rs739101; a C at rs1009150; an A at rs8141189; a G at rs2071733; a T at rs5756133; a T at rs5756129; an A at rs136206; an A at rs136213; a G at rs9610498; an A at rs1557538; a C at rs1557536; a G at rs1883273; a C at rs2239783; a C at rs12107; or a T at rs7078. In more specific examples, the at least two tag SNPs are a C at rs9622373; a C at rs5756130; an A at rs6000251; a G at rs2071731; a G at rs12159211; an A at rs9619601; a C at rs2071732; a G at rs2272827; a G at rs6000254; a T at rs875725; a T at rs8135022; a T at rs8138583; a G at rs17806513; a C at rs5756168; an A at rs8137674; or a T at rs5995283.

In another embodiment, the method includes detecting the absence of a haplotype including at least two tag single nucleotide polymorphisms, wherein the at least two tag single nucleotide polymorphisms are from the group comprising a G at rs5756152; a G at rs1005570; a G at rs16996677; or a C at rs16996674.

In one embodiment, the method includes detecting the absence of a haplotype including at least two tag single nucleotide polymorphisms in the non-coding region of the MYH9 gene, wherein the at least two tag single nucleotide polymorphisms are an A at rs5750250; a C at rs5750248; a T at rs2413396; a G at rs11912763; a T at rs4821480; a T at rs4821481; a G at rs2157256; a G at rs1005570; a T at rs2032487; a G at rs5756152; a G at rs1557529; a C at rs2239784; a T at rs16996648; a C at rs735854; a G at rs16996677; a C at rs3752462; an A at rs4821484; a T at rs8143119; a C at rs16996674; a G at rs5756157; a G at rs136196; a G at rs2157257; a G at rs735853; a C at rs739096; an A at rs739101; a T at rs1009150; a T at rs8141189; a C at rs2071733; an A at rs5756133; a C at rs5756129; a G at rs136206; a G at rs136213; an A at rs9610498; a G at rs1557538; a G at rs1557536; an A at rs1883273; a T at rs2239783; a T at rs12107; or a C at rs7078. The method can include detecting the absence of one or more of these tag SNPs.

In a further embodiment, the method includes detecting the absence of a haplotype including at least two tag single nucleotide polymorphisms in the non-coding region of the MYH9 gene, wherein the at least two tag single nucleotide polymorphisms are a T at rs9622373; a T at rs5756130; a C at rs6000251; an A at rs2071731; an A at rs12159211; a G at rs9619601; a T at rs2071732; an A at rs2272827; an A at rs6000254; a C at rs875725; a G at rs8135022; a C at rs8138583; an A at rs17806513; a T at rs5756168; a G at rs8137674; or a C at rs5995283.

The method can include determining the presence of the haplotype on both chromosomes. For example, the method can include detecting on both chromosomes the presence of a haplotype including at least two tag SNPs, when one or more of the tag SNPs is a G at rs4821480; a C at rs4821481; an A at rs1005570; a C at rs2032487; an A at rs5756152; an A at rs16996677; a T at rs3752462; a T at rs16996674; a haplotype including a C at rs735853; and/or a T at rs5756129 in a subject of African ancestry. The method can include detecting on both chromosomes the presence of a G at rs4821480; a C at rs4821481; an A at rs1005570; a C at rs2032487; and/or an A at rs5756152 in a subject of African ancestry.

Alternatively, the presence of the haplotype is detected on either one or both chromosomes, wherein the identification of the haplotype (or the SNP) on at least one chromosome indicates the subject is at risk for developing renal disease, the subject has renal disease, or has an early stage of renal disease. For example, a subject who does not have laboratory evidence of renal disease or insufficiency, such as a reduced glomerular filtration rate (GF) or an increased blood urea nitrogen (BUN) level. In another example, a haplotype is detected that includes at least two tag SNPs, wherein at least one of the two tag SNPs is a G at rs4821480; a C at rs4821481; an A at rs1005570; a C at rs2032487; an A at rs5756152; an A it rs16996677; a T at rs3752462; a T at rs16996674; a C at rs735853; a T at rs5756129; a G at rs12107; an A at rs7078; a C at rs5756130; an A at rs9619601; a T at rs875725 or any combination thereof, in a subject of African ancestry, such as an African-American subject. The method can also include detecting the presence of the SNPs themselves. In some examples, a haplotype is detected that includes at least two tag SNPs and at least one of the two tag SNPs is a G at rs4821480; a C at rs4821481; a C at rs2032487, or any combination thereof in a subject of African ancestry. The method can also include detecting the presence of these SNPs themselves. In addition, the method includes detecting the presence of both the haplotype including a T at rs3752462 and an A at rs5756152, detecting the presence of both a T at rs3752462 and an A at rs5756152. The method can also include detecting the absence of the haplotype including a C at rs3752462 and a G at rs5756152; and the absence of both a C at rs3752462 and a G at rs5756152; and the presence of a haplotype including all of a T at rs2187776, a G at rs4821480, a C at rs2032487, and a C at rs4821481. In yet a further embodiment, the method includes detecting the absence of the haplotypes including a T at rs2187776, a T at rs4821480, a T at rs2032487, or a T at rs4821481. In one embodiment, the method includes detecting the absence of all of a T at rs2187776, a T at rs4821480, a T at rs2032487, and a T at rs4821481. In yet a further embodiment, the method includes detecting the presence of a haplotype including all of: a T at rs375462; an A at rs5756152; and a G at rs15575339. In an additional embodiment, the method includes detecting the presence of a haplotype including all of (a) a T at rs4821480; (b) a C at rs2032487; (c) a C at rs4821481; and (d) a G at rs3752462 wherein each of (a)-(d) are present on both chromosomes.

In subjects of African ancestry, the methods include detecting the presence a haplotype including at least two tag SNPs in intron 23 of the MYH9 gene, which encodes heavy chain myosin HA. An exemplary amino acid sequence for heavy chain myosin HA is:

```
                                                      (SEQ ID NO: 90)
maqqaadkyl  yvdknfinnp  laqadwaakk  lvwvpsdksg  fepaslkeev geeaivelve  ngkkvkvnkd  diqkmnppkf  skvedmaelt  clneasvlhn lkeryysgli  ytysglfcvv  inpyknlpiy  seeivemykg  kkrhempphi yaitdtayrs  mmqdredqsi  lctgesgagk  tentkkviqy  layvasshks kkdqgelerq  llqanpilea  fgnaktvknd  nssrfgkfir  infdvngyiv ganietylle  ksrairqake  ertfhifyyl  lsgagehlkt  dlllepynky rflsnghvti  pgqqdkdmfq  etmeamrimg  ipeeeqmgll  rvisgvlqlg nivfkkernt  dqasmpdnta  aqkvshllgi  nvtdftrgil  tprikvgrdy vqkaqtkeqa  dfaiealaka  tyermfrwlv  lrinkaldkt  krqgasfigi ldiagfeifd  lnsfeqlcin  ytneklqqlf  nhtmfileqe  eyqregiewn fidfgldlqp  cidliekpag  ppgilallde  ecwfpkatdk  sfvekvmqeq gthpkfqkpk  qlkdkadfci  ihyagkvdyk  adewlmknmd  plndniatll hqssdkfvse  lwkdvdriig  ldqvagmset  alpgafktrk  gmfrtvgqly keqlaklmat  lrntnpnfvr  ciipnhekka  gkldphlvld  qlrcngvleg iricrqgfpn  rvvfqefrqr  yeiltpnsip  kgfmdgkqac  vlmikaleld snlyrigqsk  vffragvlah  leeerdlkit  dviigfqacc  rgylarkafa krqqqltamk  vlqrncaayl  klrnwqwwrl  ftkvkpllqv  srqeeemmak eeelvkvrek  glaaenrlte  metlqsqlma  eklqlqeqlq  aetelcaeae elrarltakk  geleeichdl  earveeeeer  cqhlqaekkk  mqqniqelee qleeeesarq  klqlekvtte  aklkkleeeq  iiledqnckl  akekklledr iaefttnlte  eeekskslak  lknkheamit  dleerlrree  kqrqelektr rklegdstdl  sdqiaelqaq  iaelkmqlak  keeelqaala  rveeeaaqkn malkkirele  sqiselqedl  eserasrnka  ekqkrdlgee  lealkteled tldstaaqqe  lrskreqevn  ilkktleeea  ktheaqiqem  rqkhsqavee
```

```
laeqleqtkr vkanlekakq tlenergela nevkvllqgk gdsehkrkkv eaqlqelqvk fnegervrte ladkvtklqv eldnvtglls qsdsksskkt kdfsalesql qdtgellqee nrqklslstk lkqvedekns freqleeeee akhnlekqia tlhaqvadmk kkmedsvgcl etaeevkrkl qkdleglsqr heekvaaydk lektktrlqq elddllvdld hqrqsacnle kkqkkfdqll aeektisaky aeerdraeae areketkals laraleeame qkaelerlnk qfrtemedlm sskddvgksv helekskral eqqveemktq leeledelqa tedaklrlev nlqamkaqfe rdlqgrdeqs eekkkqlvrq vremeaeled erkqrsmava arkklemdlk dleahidsan knrdeaikql rklqaqmkdc mrelddtras reeilaqake nekklksmea emiqlqeela aaerakrqaq qerdeladei anssgkgala leekrrlear iaqleeelee eqgntelind rlkkanlqid qintdlnler shaqknenar qqlerqnkel kvklqemegt vkskykasit aleakiaqle eqldnetker qaackqvrrt ekklkdvllq vdderrnaeq ykdqadkast rlkqlkrqle eaeeeaqran asrrklqrel edatetadam nrevsslknk lrrgdlpfvv prrmarkgag dgsdeevdgk adgaeakpae
```

The method can include detecting a haplotype comprising at least two tag SNPs, wherein one of the two tag SNPs is a T at rs2187776, a G at rs4821480, a C at rs2032487 and/or a C at rs4821481. Thus, the method can include detecting a T at rs2187776, a G at rs4821480, a C at rs2032487, a C at rs4821481 or any combination thereof.

Generally, the disclosed methods for detecting a genetic predisposition to renal disease in a human subject comprises detecting the presence of at least one tag single nucleotide polymorphism in a non-coding region of a MYH9 gene encoding non-muscle myosin heavy chain HA, or a haplotype comprising at least two tag single nucleotide polymorphism (SNPs) in a non-coding region of a MYH9 gene encoding non-muscle myosin heavy chain IIA, and the presence of the haplotype or at least one tag single nucleotide polymorphism in the non-coding region of the MYH9 gene determines the genetic predisposition to renal disease in the human subject.

In a further embodiment, the detected renal disease is FSGS or ESKD. In some examples the disease is detected in a human subject, such as a subject is infected with HIV. In other examples, the subject is of African ancestry, such as an African American.

With respect to the gene MYH9, the method can be used to detect at least one tag SNP in the non-coding region of the MYH9 gene or a haplotype comprising at least two tag SNPs in the non-coding region of the MYH9 gene, wherein the haplotype or at least one tag SNP is present in an exon of the MYH9 gene. In other embodiments, the haplotype or at least one tag SNP is present in an intron of the MYH9 gene.

Methods are also disclosed for detecting a genetic predisposition to focal segmental glomerulosclerosis or hypertensive end-stage kidney disease or both in a human subject, by detecting at least one haplotype comprising at least two tag single nucleotide polymorphisms (SNPs) in a non-coding region of a MYH9 gene encoding non-muscle myosin heavy chain HA, and the presence of the hapolotype indicates the genetic predisposition to segmental glomerulosclerosis or hypertensive end-stage kidney disease or both in the human subject.

In a further embodiment, the detected renal disease is FSGS or ESKD. In some examples the disease is detected in a human subject, such as a subject is infected with HIV. In other examples, the subject is of African ancestry, such as an African American.

Methods are also disclosed for detection of a genetic predisposition to focal segmental glomerulosclerosis or hypertensive end-stage kidney disease or both in a human subject of European ancestry. The assay can be used for early diagnosis for example before the development of renal insufficiency or renal failure, or for confirming the diagnosis of renal disease. The presence of a haplotype is detected that includes at least two tag single nucleotide polymorphisms (SNPs) in the MYH9 gene that encodes non-muscle myosin heavy chain HA, and the presence of the haplotype determines the genetic predisposition to focal segmental glomerulosclerosis or hypertensive end-stage kidney disease or both in the human subject of European ancestry. In one embodiment, a single nucleotide polymorphism is detected with an $r^2$ value of 0.75 or greater from a G at rs4821480; a C at rs4821481; or a C at rs2032487. The method can also include detecting a G at rs4821480; a C at rs4821481; or a C at rs2032487, or any combination thereof. For example, the method can include detecting all of a G at rs4821480; a C at rs4821481; and a C at rs2032487. In a further example, the method includes detecting the absence of a haplotype having at least two tag SNPs, and at least one of the two tag SNPs is a T at rs3752462.

In several examples, the presence of one or more of the tag SNPs listed herein detects FSGS in the human subject, detects the presence of hypertensive end stage renal disease, or determines the risk of developing FSGS or hypertensive end stage renal disease in the human subject. The method includes detecting any combination or sub-combination of the tag SNPs. In one example, at least one tag SNP is detected in the non-coding region of the MYH9 gene.

In one embodiment, a genetic predisposition to renal disease in a human subject of African ancestry is detected by identifying a risk allele associated with renal disease, determining the frequency of the risk allele in subjects of African ancestry, and detecting at least one tag single nucleotide polymorphism, or a haplotype comprising at least two tag single nucleotide polymorphisms (SNPs) associated with the risk allele in the MYH9 gene of the subject. The frequency of the risk allele is at least 5% in subjects of African ancestry and the presence of the haplotype or at least one tag single nucleotide polymorphism in the MYH9 gene indicates the genetic predisposition of the human subject to renal disease. In a further embodiment, the method detects a genetic predisposition to focal segmental glomerulosclerosis or hypertensive end-stage kidney stage or both.

In a further embodiment, the frequency of the risk allele in subjects of African ancestry is at least 5%, at least 10%, at least 15%, at least 20%, at least 25%, at least 30%, at least 35%, at least 40% or at least 50%. In several instances, the single nucleotide polymorphism is in a non-coding region of the MYH9 gene. In other examples, the single nucleotide polymorphism is present in an intron of the MYH9 gene. In still a further embodiment, the single nucleotide polymorphism is present in an exon of the MYH9 gene, for example exon 14, exon 19, exon 26, exon 33, exon 34, or exon 41. In several embodiments, the tag single nucleotide polymorphism used to identify the frequency of the risk allele in subjects of African ancestry is set forth in any of Tables 4-8. In one embodiment, the subject of African ancestry is African American.

In another embodiment, the haplotype comprising at least two tag single nucleotide polymorphisms used to identify the frequency of the risk allele in subjects of African ancestry is set forth in any of Tables 4-8. In one embodiment, the subject of African ancestry is African American.

An array is also disclosed for detecting a genetic predisposition to renal disease in a human subject. The array contains probes complementary to at least one tag single nucleotide polymorphism in a non-coding region of a MYH9 gene that encodes non-muscle myosin heavy chain IIA. Each of the tag single nucleotide polymorphisms is associated with a risk allele for renal disease and the probes complementary to the tag single nucleotide polymorphism hybridize specifically to the non-coding region of the MYH9 gene as set forth in any of Tables 4-8. The array can include about 10, about 20, about 30, about 40, about 50, about 60, about 70, about 80, about 90, or more probes.

In one example, the probes on the array are complementary to at least one tag single nucleotide polymorphism in the non-coding region of the MYH9 gene, wherein the tag SNP is a G at rs5750250; a T at rs5750248; a C at rs2413396; a A at rs11912763; a G at rs4821480; a C at rs4821481; an A at rs2157256; an A at rs1005570; a C at rs2032487; an A at rs5756152; an A at rs1557529; a T at rs2239784; a C at rs16996648; a T at rs735854; an A at rs16996677; a T at rs3752462; a C at rs4821484; a G at rs8143119; a T at rs16996674; a T at rs5756157; an A at rs136196; an A at rs2157257; a C at rs735853; a G at rs739096; a G at rs739101; a C at rs1009150; an A at rs8141189; a G at rs2071733; a T at rs5756133; a T at rs5756129; an A at rs136206; an A at rs136213; a G at rs9610498; an A at rs1557538; a C at rs1557536; a G at rs1883273; a C at rs2239783; a C at rs12107 or a T at rs7078.

In another example, the probes on the array are complementary to at least one tag single nucleotide polymorphism in the non-coding region of the MYH9 gene, wherein the tag SNPs is a C at rs9622373; a C at rs5756130; an A at rs6000251; a G at rs2071731; a G at rs12159211; an A at rs9619601; a C at rs2071732; a G at rs2272827; a G at rs6000254; a T at rs875725; a T at rs8135022; a T at rs8138583; a G at rs17806513; a C at rs5756168; an A at rs8137674; or a T at rs5995283.

In one embodiment, the probes in the array (complementary to at least one tag single nucleotide polymorphism in the non-coding region of the MYH9 gene) are present in an exon of the MYH9 gene such as exon 14, exon 19, exon 26, exon 33, or exon 41. In a further embodiment, the probes in the array (complementary to at least one tag single nucleotide polymorphisms in the non-coding region of the MYH9 gene) are present in an intron of the MYH9 gene.

In one example, the probes in the array may be complementary to at least one tag single nucleotide polymorphism in the non-coding region of the MYH9 gene such as any one of the tag SNPs selected from a G at rs5750250; a T at rs5750248; a C at rs2413396; a A at rs11912763; a G at rs4821480; a C at rs4821481; an A at rs2157256; an A at rs1005570; a C at rs2032487; an A at rs5756152; an A at rs1557529; a T at rs2239784; a C at rs16996648; a T at rs735854; an A at rs16996677; a T at rs3752462; a C at rs4821484; a G at rs8143119; a T at rs16996674; a T at rs5756157; an A at rs136196; an A at rs2157257; a C at rs735853; a G at rs739096; a G at rs739101; a C at rs1009150; an A at rs8141189; a G at rs2071733; a T at rs5756133; a T at rs5756129; an A at rs136206; an A at rs136213; a G at rs9610498; an A at rs1557538; a C at rs1557536; a G at rs1883273; a C at rs2239783; a C at rs12107; a T at rs7078; a C at rs9622373; a C at rs5756130; an A at rs6000251; a G at rs2071731; a G at rs12159211; an A at rs9619601; a C at rs2071732; a G at rs2272827; a G at rs6000254; a T at rs875725; a T at rs8135022; a T at rs8138583; a G at rs17806513; a C at rs5756168; an A at rs8137674; or a T at rs5995283, and wherein the probes on the array fail to hybridize with any one of the protective allele SNPs disclosed herein.

In another embodiment, the probes in the array are complementary to a protective allele in the MYH9 gene such as those disclosed herein. In this example, the output from the array can provide an indication of the presence of protective alleles for the MYH9 gene in a sample.

It will be readily apparent to one skilled in the art that the exact formulation of probes on an array is not critical as long as the user is able to select probes for inclusion on the array that fulfill the function of hybridizing to a protective allele of the MYH9 gene or probes that are complementary to a tag SNP, wherein the tag SNPs is associated with a risk allele of the MYH9 gene. The array can be modified to suit the needs of the user, for example, an array can contain a multitude of probes that are complementary to a protective allele of the MYH9 gene or complementary to a risk allele of the MYH9 gene. Thus, analysis of the array can provide the user with information regarding the number and/or presence of risk alleles and/or protective alleles in a given sample. The hybridization of a probe complementary to a risk allele of the MYH9 gene in an array can indicate that the subject from whom the sample was derived is at an elevated risk for developing a disease such as renal disease. In one embodiment, the renal disease includes FSGS or ESKD.

Methods for Detecting a Genetic Predisposition to Additional Diseases

The role of the MYH9 gene in the development of disease and disorders is still under investigation. The instant disclosure links the MYH9 gene with a number of clinical disorders that are in some cases associated with kidney disease (nephropathy). For example, the MYH9 gene is believed to play an important role in several diseases that encompass failed or reduced kidney function, such as FSGS. Hence, a subject with a disease, or suspected of being at risk for developing a disease such as FSGS, can be treated, assessed or monitored by detecting at least one tag SNP in a non-coding region of the MYH9 gene or a haplotype comprising at least two tag SNPs in the non-coding region of the MYH9 gene. The presence of the haplotype or at least one tag SNP indicates the genetic risk of the subject to the disease.

Generally, at least one tag SNP in the non-coding region of the gene of interest, or a haplotype is detected that contains at least two tag SNPs in a non-coding region of a gene of interest, for example MYH9. The presence of one or more tag SNP themselves may be detected. In other embodiments, the presence of at least one tag SNP in a non-coding region of the MYH9 gene is detected. In some embodiments, the presence of one or more tag SNPs, or haplotype blocks including SNPs in a non-coding region of a gene of interest, indicates whether a therapeutic regimen or agent (such as a particular treatment) can be used to treat the subject. For example, it is possible to determine if preventative or prophylactic treatment should be administered to a subject at risk for developing a disease such as asthma, sickle cell anemia, glaucoma, cerebral malaria, lacunar stroke, hypertension, human immunodeficiency virus, systemic sclerosis, diabetes mellitus, preeclampsia or systemic lupus erythematosus, or if a treatment should be administered to a subject to prevent the progression of existing disease, such as from an early stage to a more advanced stage of the disease. Detection and treatment of asthma, sickle cell anemia, glaucoma, cerebral malaria, lacunar stroke, hypertension, human immunodeficiency virus infection, systemic sclerosis, diabetes mellitus, preeclampsia or systemic lupus erythematosus will be discussed in more detail below.

The genetic predisposition of a subject to non-renal diseases can be determined. For example, it can be determined whether a subject has or is at risk for developing asthma, sickle cell anemia, glaucoma, cerebral malaria, lacunar stroke, hypertension, human immunodeficiency virus disease, systemic sclerosis, diabetes mellitus, preeclampsia or systemic lupus erythematosus.

In some embodiments, the method includes detecting the presence of a genotype, such that both alleles of the genotype of the subject are a haplotype that includes at least two tag SNPs. The at least two tag SNPs may be in the non-coding region of a gene of interest, for example, MYH9. In other embodiments, the presence of a single allele is detected such that the allele of the subject includes at least one tag SNP in the non-coding region of the gene of interest. Thus, the disclosed methods include detecting one or two copies of a tag SNP in the genome of the subject.

In another embodiment, protective alleles are identified that are associated with the absence of one or more of the above diseases. In this instance, detection of protective alleles in the non-coding region of the gene of interest, such as MYH9, are indicative of a lower risk for developing one or more of the above diseases in the subject from whom the sample was derived.

In some embodiments, the genetic predisposition of a human subject to a disease is determined in a subject that is of African ancestry, such as an African-American subject (a subject who is of African ancestry who resides in the United States) or an African-European subject (a subject who is of African ancestry who resides in Europe). The subject can self-identify (such as on a questionnaire) as being of African ancestry. However, there are a number of software programs available to confirm African ancestry, if such confirmation is desired. These include the program STRUCTURE™ (version 2.2, available on the University of Chicago website on Jan. 28, 2009). In additional embodiments, the subject is of European ancestry. The human subject can self-identify (such as on a questionnaire) as being of European ancestry, such as identifying themselves as Caucasian. Software programs are available to confirm European ancestry, if such confirmation is desired. These include the program STRUCTURE™ (version 2.2, available on the University of Chicago website on Jan. 28, 2009) and the program EURASIANDNA™, version 1.0 and 2.0 (available from DNAPRINT™).

In addition to determining risk, the detection assay may be used for genetic confirmation of a suspected disease, for example a subject who presents with clinical or laboratory evidence of a disease. In one example, a subject suspected of being infected with the HIV may present with seropostive test results and the assay detects a predisposition to develop HIV-associated nephropathy. In another example, a subject may present with headaches, reduced visual field, eye pain or optic disc atrophy, and the genetic test detects a predisposition to develop glaucoma. The methods are also useful for determining a therapeutic regimen for the treatment of a subject of interest, or determining if a subject will benefit from treatment with a particular therapeutic regimen. In some examples early treatment can be initiated to avoid further progression of disease, as in glaucoma.

The subject may have clinical or laboratory evidence of early disease, such as a child with periods of sudden pain that is often associated with sickle cell disease and the genetic test is performed to confirm the diagnosis of the disease. For example, the subject may be an African American with clinical evidence of early optic neuropathy without a known etiology. Alternatively, the subject may have had a tissue biopsy performed with inconclusive or ambiguous results. In these instances, the genetic test is performed to arrive at a diagnosis of disease with a higher degree of clinical certainty than would otherwise be possible. The genetic test can be used in association with other clinical signs and symptoms to assign a diagnosis, and from the diagnosis greater prognostic certainty can be provided to the subject. Alternatively, the genetic test can be used to provide a more specific diagnosis or etiology for the disease under investigation, as may be needed in research studies or for the selection of an appropriate therapeutic regimen.

In some embodiments, a sample is obtained from a human subject of interest, and the nucleic acids in the sample analyzed for the presence of at least one tag SNP in a non-coding region of the MYH9 gene. In other embodiments, the sample contains nucleic acids from a human subject of interest, and the nucleic acids are analyzed for the presence of a haplotype including at least two tag SNPs in a non-coding region of the MYH9 gene. The methods can include selecting a subject in need of detecting the presence of the haplotype, and obtaining a nucleic acid sample from this subject. For example, a subject can be selected who is suspected to possess a genetic predisposition to a disease, such as preeclampsia or systemic sclerosis. In another example, the selected subject is of African ancestry and/or is infected with HIV. Thus, the subject's risk for progressing to another stage of the disease can be detected. The methods disclosed herein can also be used to confirm the presence of the disease in the subject.

Biological samples include all clinical samples useful for detection of diseases such as asthma, sickle cell anemia, glaucoma, cerebral malaria, lacunar stroke, hypertension, human immunodeficiency virus, systemic sclerosis, diabetes mellitus, preeclampsia or systemic lupus erythematosus in subjects, including, but not limited to, cells, tissues, and bodily fluids, such as: blood; derivatives and fractions of blood, such as serum; extracted galls; biopsied or surgically removed tissue, including tissues that are, for example, unfixed, frozen, fixed in formalin and/or embedded in paraffin; tears; milk; skin scrapes; surface washings; urine; sputum; cerebrospinal fluid; prostate fluid; pus; or bone marrow aspirates. In a particular example, a sample includes blood obtained from a human subject, such as whole blood or serum. In another particular example, a sample includes buccal cells, for example collected using a swab or by an oral rinse. In additional embodiments, the method includes analyzing DNA sequence data previously obtained from the subject of interest.

In one example, a sample including nucleic acids can be obtained from a subject who is suspected to have a genetic predisposition to asthma, sickle cell anemia, glaucoma, cerebral malaria, lacunar stroke, hypertension, human immunodeficiency virus, systemic sclerosis, diabetes mellitus, preeclampsia or systemic lupus erythematosus. The subject can have family members who have had one or more of the above diseases. In another example, a sample including nucleic acids can be obtained from a subject that is of African ancestry. In a further example, a sample includes nucleic acids obtained from a subject with European ancestry.

In a further example, a sample including nucleic acids is obtained from a subject who has, or who has suffered from, asthma, sickle cell anemia, glaucoma, cerebral malaria, lacunar stroke, hypertension, human immunodeficiency virus, systemic sclerosis, diabetes mellitus, preeclampsia or systemic lupus erythematosus and wherein it is of interest to monitor progression of one or more of the above diseases in the subject. For example, a sample can be obtained from a subject who presents with symptoms of one of the above diseases or who presents with spirometric indices of asthma, a family history of sickle cell anemia, elevated intracranial pressure in the case of cerebral malaria and lacunar stroke, or elevated intraocular pressure in the case of glaucoma.

Methods of isolating nucleic acid molecules from a biological sample are routine, for example using PCR to amplify the molecules from the sample, or by using a commercially available kit to isolate DNA. Nucleic acid molecules isolated from PBMCs or any other biological sample can be amplified using routine methods to form nucleic acid amplification products.

Idiopathic FSGS occurs more frequently among individuals of African ancestry than individuals of Asian or European ancestry. FSGS is known to accelerate in severity with increasing accumulation of podcyte injury to the kidneys. If left untreated, FSGS can develop into ESKD. It is therefore envisioned by the instant disclosure that individuals can be genotyped at birth, or at a later date, to determine if the individual carries one or two copies of the MYH9 gene or one or more risk alleles in the non-coding region of the MYH9 gene. Those individuals that have one or two copies of the MYH9 gene and also possess one or more risk alleles in the non-coding region of the MYH9 gene possess a higher genetic predisposition for developing FSGS than an individual without a risk allele in the non-coding region of the MYH9 gene. Individuals carrying one or more risk alleles in the non-coding region of the MYH9 gene would benefit from genetic counseling which may also include recommendations for regular monitoring or aggressive prophylactic regimes to help limit the amount of accumulating damage in the kidneys. Individuals with one copy of the MYH9 gene are also at an elevated risk for developing FSGS as compared to an individual that does not carry a risk allele of the MYH9 gene. It is also believed that an individual with at least one risk allele in the non-coding region of the MYH9 gene is at greater risk for developing FSGS following exposure to a relevant environmental agent, such as an unidentified toxin or virus or bee sting. Such an individual can be monitored for the development of FSGS following such an exposure.

In one representative protocol, testing or screening for characteristics of FSGS begins at approximately 10 years of age and continues until the individual is at least 20 yrs old. In some embodiments, testing may occur on a semi-annual or annual basis, and the urine of the subject is tested for the presence of albumin Microalbuminurea occurs when the kidneys leak small amounts of protein into the urine. A normal range for microalbuminurea is less than 30 mg/day. The level of albumin detected in the urine of an FSGS subject is typically greater than 30 mg/day and more frequently between 30 mg/day and 300 mg/day. Thus, those individuals with one of more copies of the MYH9 gene or one or more risk alleles in the non-coding region of the MYH9 gene can be tested using a routine dipstick test to gauge albumin content. The albumin level observed can be used to indicate if the individual is in the normal clinical range or if the individual is producing abnormally high levels of albumin in the urine. The results of this diagnostic test or other tests, such as a 24 hr urine collection method, can be used to determine if the subject needs to undergo treatment, or in extreme cases of albumin output, undergo aggressive treatment, such as the administration of ACE inhibitors to prevent accumulation of podocyte damage in the kidneys.

The albumin content of a urine sample may be compared against a serum concentration of creatinine, known in the art as the albumin/creatinine ratio (ACR). This method is often cited as being more reliable than a single dipstick test because the creatinine concentration remains fixed in a subject, whereas the albumin level may become more dilute (or concentrated) based on a subject's urine output. It is contemplated herein that a subject can be treated prior to the onset of FSGS based on the identification of one or more risk alleles in the non-coding region of the MYH9 gene and/or the presence of elevated albumin or ACR levels in a sample from the subject. Individuals with microalbuminurea can be monitored for disease progression and may also undergo prophylactic treatment to prevent the onset of physical symptoms of FSGS through the use of pharmaceuticals such as ACE Inhibitors.

Several lines of evidence point to kidney disease as an important complication of human immunodeficiency virus (HIV) infection. Kidney function is abnormal in up to 30% of HIV-infected patients. AIDS-related kidney disease has become a relatively common cause of end-stage renal disease (ESRD) requiring dialysis. HIV infection can result in kidney failure due to HIV infection of kidney cells or other causes such as administration of anti-retroviral medications. HIV-associated nephropathy (HIVAN) is highly prevalent among HIV-positive people in Africa, with recent studies showing rates of between 25% and 50% in Kenya and Uganda. Current guidelines for the management of patients with HIV mandate that all patients at the time of HIV diagnosis be assessed for existing kidney disease with a screening urine analysis for proteinuria and a calculated estimate of renal function (creatinine clearance or glomerular filtration rate (GFR). If there is no evidence of proteinuria at initial evaluation, patients at high risk for the development of renal disease (e.g., African American, those with CD4+ cell counts <200 cells/mL, HIV RNA levels >4000 copies/mL, or those with diabetes mellitus, hypertension, or hepatitis C virus coinfection) should undergo annual screening to monitor progression of disease. Patients with proteinuria or reduced renal function should be referred to a nephrologist and undergo additional evaluation, including quantification of proteinuria, renal ultrasound, and potentially renal biopsy. Therapy for HIV-associated renal diseases should be individualized to the patient's clinical circumstances and to the underlying renal histology findings. However, elevated blood pressure in HIV-infected patients may be controlled through the use of angiotensin-converting enzyme (ACE) inhibitors or angiotensin receptor blockers for those patients with proteinuria. In addition, patients with HIV-associated nephropathy (HIVAN) are treated with highly active antiretroviral therapy (HAART) at diagnosis.

The presence of the MYH9 gene in a subject is believed to play an important role in the development of clinical symptoms of HIV associated nephropathy, especially in those individuals carrying one or more risk alleles of the non-coding region of the MYH9 gene or individuals who carry one or two copies of the MYH9 gene. It is also believed that HIV infected individuals carrying one or more risk alleles in the non-coding region of the MYH9 gene or who carry one or two copies of the MYH9 gene have an elevated risk for developing kidney related complications (nephropathy). Individuals with one or more risk alleles of the MYH9 gene or two copies of the MYH9 gene are therefore considered more susceptible to renal damage associated with HIV infection. Therefore, individuals can be genotyped for the MYH9 gene, and the presence of one or more risk alleles in the non-coding region of the MYH9 gene, or two copies of the MYH9 gene, are associated with an increased risk of developing HIV-associated renal disease.

Hypertension is a medical condition in which blood pressure is chronically elevated. Hypertension can be classified either essential (primary) or secondary. Essential hypertension indicates that no specific medical cause can be found to explain a subject's condition. Secondary hypertension indicates that the high blood pressure is a result of (i.e., secondary to) another condition, such as kidney disease. Persistent hypertension is one of the risk factors for strokes, heart attacks, heart failure and arterial aneurysm, and is a leading cause of chronic renal failure. Even moderate elevation of arterial blood pressure leads to shortened life expectancy. At severely high pressures, defined as mean arterial pressures 50% or more above average, a person can expect to live no more than a few years unless appropriately treated, for example with dialysis or transplantation. In individuals older than 50 years, hypertension is considered to be present when a person's systolic blood pressure is consistently 140 mm Hg or greater or when the diastolic blood pressure is consistently 90 mm Hg or greater. Beginning at a systolic pressure of 115 and diastolic pressure of 75 (commonly written as 115/75 mm Hg), cardiovascular disease (CVD) risk doubles for each increment of 20/10 mmHg Pre-hypertension is defined as blood pressure from 120/80 mm Hg to 139/89 mm Hg. Pre-hypertension is not a disease category; rather, it is a designation chosen to identify individuals at high risk of developing hypertension. It is well known in the art that individuals of African ancestry including African Americans have an elevated risk for developing hypertension and are thus, likely candidates for pre-hypertension. The allele frequency for the MYH9 gene in African Americans is about 60%; with about 36% of those individuals carrying two risk alleles. The genetic model for MYH9 is recessive. In other words, two copies of the MYH9 gene provide the highest risk for developing a disease, such as hypertension, as compared to the rest of the population. It is contemplated herein that one copy of the gene provides an elevated risk for developing hypertension but at a rate that is anticipated to be typically lower than for individuals with two copies of the MYH9 gene.

It is a feature of the instant invention that individuals suspected to suffer from hypertension or individuals diagnosed with hypertension can be genotyped to establish the status of the MYH9 gene. The individuals that screen positive for risk alleles in the non-coding region of the MYH9 gene can be treated with more aggressive therapeutic regimens than those individuals that are negative for risk alleles in the non-coding region of the MYH9 gene, in order to limit the amount of accumulative damage in the kidney and thus, prevent long-term or permanent renal damage. Hypertension can be treated with the use of pharmaceuticals that lower arterial blood pressure such as Angiotensin-Converting Enzyme Inhibitors (ACE Inhibitors). Accordingly, it is contemplated herein that individuals who carry at least one risk allele of the MYH9 gene possess a genetic predisposition for the development of hypertension and may also develop chronic renal disease at a higher rate than individuals without a MYH9 risk allele. Thus, the ability to detect risk alleles in the non-coding region of the MYH9 gene in a subject at birth, or at a later date, can provide useful information to the medical field to develop prophylactic treatment regimes and/or monitoring strategies for individuals with an elevated risk that concurrently reduces the likelihood of the onset of hypertension.

Individuals diagnosed with hypertension could also benefit from the process of genotyping the MYH9 gene to establish if the affected individual carries one or more risk alleles in the non-coding region of the MYH9 gene. The presence of risk alleles in the MYH9 gene is contemplated to correlate with an increased risk for accumulation of kidney damage and ultimately, renal failure. Therefore, individuals with hypertension that also carry one or more risk alleles in the non-coding region of the MYH9 gene can be treated differently than individuals lacking a MYH9 risk allele, because of the inherent fragile state of the affected subject's kidneys.

Preeclampsia is a medical condition of hypertension arising in pregnancy (pregnancy induced hypertension (PIH)) in association with significant amounts of protein in the urine. The symptoms of preeclampsia are therefore similar in nature to hypertension. While blood pressure elevation is the most visible sign of the disease, it involves generalized damage to the maternal endothelium, kidneys and liver. Preeclampsia may develop from 20 weeks gestation (it is considered early onset before 32 weeks, which is associated with increased morbidity) and its progress differs among patients. Apart from abortion, Caesarean section, or induction of labor, and therefore delivery of the placenta, there is no known cure. The symptoms of hypertension in preeclampsia can be controlled for example, through the use of medications such as beta blockers.

It is believed herein that the presence of one or more risk alleles in the non-coding region of the MYH9 gene plays an important role in the onset and severity of preeclampsia. It is proposed herein, that an individual carrying one or more risk alleles in the non-coding region of the MYH9 gene or who carries two copies of the MYH9 gene possesses a genetic predisposition to develop preeclampsia. These individuals are considered more susceptible to preeclampsia because of the associated increased risk these individuals have to develop hypertension. Accordingly, in one embodiment of the instant disclosure women are genotyped for the MYH9 gene, and the presence of one or more risk alleles in the non-coding region of the MYH9 gene or two or more copies of the MYH9 gene are associated with an increased risk of developing preeclampsia. In another embodiment, preventive or prophylactic treatment is administered to an individual carrying one or more risk alleles in the non-coding region of the MYH9 gene or who possesses two copies of the MYH9 gene in order to reduce or avoid the development of preeclampsia in a genetically susceptible individual. For example, the treatment is administration of a beta-blocker.

In another embodiment, the present disclosure is directed to the treatment of subjects with diabetes mellitus. For example, a diabetic subject can be genotyped for the MYH9 gene and the presence of one or more risk alleles in the non-coding region of the MYH9 gene. Individuals diagnosed with diabetes mellitus and found to carry one or more risk alleles in the non-coding region of the MYH9 gene can be monitored over time, for example, from early stage diabetes to progression of advanced disease, and differences in the individual's health are noted and correlated with progression of diabetes in the subject. It is well known in the art that individuals of African ancestry (including African Americans) have an increased risk of developing diabetes. Accordingly, in some instances it is anticipated that the subject will be of African ancestry. Thus, a subject who is diagnosed with diabetes and found to possess one or more risk alleles in the non-coding region of the MYH9 gene can be treated with drugs that lower arterial blood pressure. It is believed that treatment of the subject with drugs that lower arterial blood pressure such as Angiotension-Converting Enzyme Inhibitors (ACEI) can successfully limit the amount of accumulative damage, scarring and podocyte injury inflicted on the kidney and thus spare the kidney from further complications of renal disease (nephropathy). It is also contemplated that the MYH9 risk allele increases the odds ratio for diabetic nephropathy to a modest degree (1.3) and that when a large cohort is studied, this effect becomes significant.

Systemic sclerosis (SSc) is a clinically heterogeneous, systemic disorder which affects connective tissue of the skin, internal organs and walls of blood vessels (especially the esophagus, lower GI tract, lung, heart, and kidney). It is characterized by alterations of the microvasculature, disturbances of the immune system and by massive deposition of collagen and other matrix substances in connective tissue. SSc is about 4 times more common among women than men. It is most common in the 3rd to 5th decades of life and is rare in children. The course of SSc depends on the type but is often unpredictable. Typically, progression is slow. Overall 10-yr survival is about 65%. Most patients with diffuse skin disease eventually develop visceral complications, which are the usual causes of death. Additionally, prognosis is poor if cardiac, pulmonary, or renal manifestations present early. While no drug significantly influences the natural course of SSc overall, various drugs are of value in treating specific symptoms or organ systems, such as immunosuppressant's or when accompanied by renal manifestation, treatment with ACE Inhibitors.

It is believed herein that the presence of one or more risk alleles in the non-coding region of the MYH9 gene or two copies of the MYH9 gene in a subject is associated with development and/or progression of SSc. Individuals, in particular women, are considered more susceptible to kidney, heart, and pulmonary damage because of hypertension or elevated intravascular pressure associated with the symptoms of SSc. Individuals are therefore genotyped for the MYH9 gene, and the presence of one or more risk alleles in the non-coding region of the MYH9 gene or two or more copies of the MYH9 gene are associated with an increased risk of developing SSc. Preventive or prophylactic treatment can be administered to such an individual to delay, diminish, or avoid the development of SSc in a genetically susceptible individual. Accordingly, a strategy for patient care can be determined using annual or semi-annual follow-up examinations in which an individual suspected of being at risk of developing SSc is tested for elevated blood pressure, microalbuminurea, and other methods that are predictive of elevated arterial blood pressure or impaired kidney function. Results that are indicative of pulmonary, cardiac or kidney impairment may be used as a basis for selecting an appropriate treatment for the symptoms of SSc.

Systemic lupus erythematosus (SLE) is a chronic, multi-faceted inflammatory disease that can affect every organ system of the body. It is more prevalent in individuals of African ancestry than individuals of European or Asian ancestry. The kidney is the most commonly affected visceral organ in SLE. Although only approximately 50% of patients with SLE develop clinically evident renal disease, biopsy studies demonstrate some degree of renal involvement in almost all patients. Glomerular disease usually develops within the first few years of SLE onset and is usually asymptomatic. It is contemplated herein that the MYH9 gene plays an active role in the development and/or progression of SLE. Therefore methods are disclosed to screen for the risk of developing SLE by determining whether an individual carries one or more risk alleles in the non-coding region of the MYH9 gene or carry two copies of the MYH9 gene. The assay is therefore designed to detect those who are genetically predisposed to develop SLE or predisposed to develop SLE associated nephropathy. Acute or chronic renal failure may occur in SLE and these symptoms can be treated with drugs conventionally used to treat hypertension.

In one embodiment, individuals are genotyped for the MYH9 gene, and the presence of one or more risk alleles in the non-coding region of the MYH9 gene or two copies of the MYH9 gene are associated with an increased risk of developing SLE-associated nephropathy. Preventive or prophylactic treatment is administered to an individual carrying one or more risk alleles in the non-coding region of the MYH9 gene in order to reduce or delay the onset or development of SLE associated nephropathy. In some cases, the genetically susceptible individual can be treated through the administration of conventional anti-hypertension drugs in order to treat the symptoms of SLE.

A subject in need of kidney transplantation can also be genotyped for the presence of risk alleles in the non-coding region of the MYH9 gene. It is known that individuals of African ancestry including African Americans have an elevated risk for carrying one or two copies of the MYH9 gene. In addition, it is also known that individuals of African ancestry have an increased risk of developing idiopathic kidney disease. Interestingly, individuals of European American ancestry or Asian ancestry have a significantly lower risk of developing kidney disease and lower rates as carriers of one or both copies of the MYH9 gene, currently observed at 4% or lower. Thus, in one embodiment, a kidney recipient can be genotyped to determine if the recipient carries one or both copies of the MYH9 gene and to determine if the recipient possesses one or more risk alleles in the non-coding region of the MYH9 gene. If the recipient is determined to possess one or more of the risk alleles the recipient is considered at an elevated risk of developing further kidney disease, even with a newly transplanted kidney due to the genotype status of the subject. In such instances, pre- and/or post-transplantation treatments are initiated such as, administration of drugs that reduce hypertension, to protect the newly transplanted kidney, and ultimately avoid kidney failure in the recipient.

Additionally, a kidney selected for transplantation can undergo genotyping prior to surgery to establish the genotype status of the organ. If the recipient is negative for risk alleles in the non-coding region of the MYH9 gene and the donor kidney is positive for risk alleles in the non-coding region of the MYH9 gene then the recipient is given pre- and/or post-transplantation treatment regimens that reduce the risk of the donated kidney undergoing subsequent kidney failure. Additionally, it may be necessary to treat a subject who is to receive a kidney that is positive for one or more risk alleles in the non-coding region of the MYH9 gene differently from a subject who is to receive a kidney that does not possess a MYH9 risk allele. Therapeutic treatment and regimens can therefore be developed after genotyping of a subject or an organ for MYH9 genotype.

Asthma and severe asthma is more commonly observed in subjects of African ancestry than subjects of European or Asian ancestry only. MYH9 is known to be expressed in lung tissue and it is contemplated herein to play an active role in the development and/or severity of asthma. MYH9 is believed to promote excessive construction of the bronchi through the regulation of myosin, and therefore muscle contraction and relaxation. In certain embodiments of the method, subjects with asthma (or suspected of having asthma) may be genotyped, to establish if the subject carries one or two copies of the MYH9 gene. Additionally, a subject may be genotyped to determine if the subject possesses one or more risk alleles in the non-coding region of the MYH9 gene such as any of the tag SNPs observed in Tables 4-8. Subjects with two copies of the MYH9 gene or with one or more risk alleles in the non-coding region of the MYH9 gene are considered at greater risk for severe asthmatic conditions. Such high risk individuals may be given tailored treatments for example administration of ACE Inhibitors to the subject in order to promote relaxation of bronchi muscles. In a further embodiment, it is contemplated herein that a subject with one or more risk alleles in the non-coding region of the MYH9 gene such as any of the tag SNPs observed in Tables 4-8, and exhibits clinical symptoms of asthma can be treated with Fasidil™, a potent Rho-kinase inhibitor, that reduces the level of phosphorylation in the muscles which in turn cause relaxation of the bronchi muscles. Accordingly, it is believed that Fasidil™ is a potential drug for the treatment of asthma in individuals with one or two copies of the MYH9 gene or at least one risk allele in the non-coding region of the MYH9 gene.

Sickle cell disease is a group of disorders that affects hemoglobin, the molecule in red blood cells that delivers oxygen to cells throughout the body. People with this disorder have atypical hemoglobin molecules called hemoglobin S, which can distort red blood cells into a sickle, or crescent, shape. A particularly serious complication of sickle cell disease is high blood pressure in the blood vessels that supply the lungs (pulmonary hypertension). These blood vessels narrow and their walls thicken making the ability to deliver oxygen-rich blood to the lungs increasingly more difficult. Pulmonary hypertension occurs in about one-third of adults with sickle cell disease and can lead to heart failure.

It is believed that the presence of at least one risk allele in the non-coding region of the MYH9 gene or one or two copies of the MYH9 gene is associated with an increase risk for the development of sickle cell anemia associated nephropathy. Sickle cell anemia is prevalent in individuals of African ancestry. In one embodiment of the instant disclosure, a subject diagnosed with sickle cell anemia is screened for the presence of one or two copies of the MYH9 gene and at least one risk allele in the non-coding region of the MYH9 gene. Individuals that possess at least one risk allele in the non-coding region of the MYH9 gene or who carry one or two copies of the MYH9 gene and show the beginning symptoms of sickle cell disease can be treated with medications that address or delay the effects of nephropathy. It is also contemplated herein that genotyping of an individual can occur during early childhood, or at a later date during childhood, or at subsequent times during their lifetime. Individuals at risk are given prophylactic or therapeutic treatment regimens appropriate for an individual with sickle cell anemia. It is complemented herein that in addition to standard forms of sickle cell treatment other therapies may include inhalants such as oxygen and nitric oxide; blood exchanges through transfusions; and use of vaso-dilator drugs such as Viagra™ in combination with hypertension or ACE Inhibitor based medications. It is believed that the MYH9 risk haplotype is associated with reduced glomerular filtration rate sickle cell anemia, compared to individuals with the non-risk haplotype. Thus the presence of the MYH9 risk allele in a subject known to have sickle cell anemia is one indication of increased probability of reduced glomerular filtration rate, which indicates kidney disease.

Lacunar infarctions occur due to abnormalities of blood vessels in the brain. It is known that particular human populations have an increased risk for suffering a lacunar stroke, such as individuals of African ancestry including African Americans. This risk is also increased by MYH9 associated genetic risk, and particularly aggressive therapeutic measures are initiated in subjects with such risk. For example, a 50 year old African American who possess two copies of the MYH9 gene and has at least one risk allele in the non-coding region of the MYH9 may be observed to have a blood pressure reading of 140/90 mm Hg. A clinician may suggest that the blood pressure goal for such a high-risk individual is 130/80 mm Hg in order to avoid suffering a lacunar stroke. This particular type of patient management is generally aimed at those populations at risk for suffering a lacunar stroke such as subjects of African ancestry, and is not typically aimed at the general population. However, the presence of the genetic risk in non-African Americans can also be treated more aggressively. In the above representative example, the individual may also receive a hypertension-based pharmaceutical such as an ACE Inhibitor as a means to lower the pressure within the brain blood vessels so as to reduce the risk of the subject suffering a lacunar stroke.

Cerebral malaria (CM) collectively involves the clinical manifestations of *Plasmodium falciparum* malaria that induce changes in mental status and coma. While millions of cases of malaria occur each year only 20-50% of these develop into CM. It is currently estimated that cerebral malaria affects more than 750,000 children a year in sub-Saharan Africa. It is well known that individuals of African ancestry have higher rates of CM than individuals of European or Asian ancestry given the closer geographical proximity to infected mosquitoes. Cerebral malaria is an acute, widespread disease of the brain which is accompanied by fever. The mortality ratio is between 25-50% and if a person is not treated, CM is fatal within 24-72 hours. The histopathological hallmark of this disease is sequestration of cerebral capillaries and venules with parasitized red blood cells (PRBCs) and non-PRBCs (NPRBCs). Cerebral malaria develops in severity as parasitized red blood cells (PRBCs) adhere to the cerebral microvasculature, causing a blockage of blood passage. This blockage stops blood flow, leading to a shortage of oxygen and nutrients in those affected areas of the brain which can result in brain damage or stroke. The occlusion of small blood vessels occurs diffusely throughout brain. This phenomenon appears to occur in all patients with cerebral malaria, although there are numerous other complications that occur as a result of this disease. Disease risk factors include being a child less than 10 years of age and living in malaria-endemic area.

It is believed that the presence of one or more risk allele in the non-coding region of the MYH9 gene or one or two copies of the MYH9 gene plays an important role in the progression and severity of cerebral malaria. It is proposed herein, that an individual carrying one or more risk alleles in the non-coding region of the MYH9 gene or one or two copies of the MYH9 gene possesses a genetic predisposition to develop CM or CM associated nephropathy upon exposure to a diseased mosquito. Individuals with one or more risk alleles in the non-coding region of the MYH9 gene or two copies of the MYH9 gene are considered more susceptible to long-term brain damage because these individuals are more susceptible to develop elevated intracranial pressure, as associated with cerebral malaria. MYH9 is expressed in platelets and the platelets may act as a ridge between infected red blood cells and endothelium of capillaries and venules in the brain. Accordingly, in one embodiment of the instant disclosure, individuals, especially young children, are genotyped for the MYH9 gene, and the presence of one or more risk alleles in the non-coding region of the MYH9 gene or one or two copies of the MYH9 gene is associated with an increased risk of developing CM upon exposure to the causative agent. Preventive or prophylactic treatment can be administered to an individual carrying one or more risk alleles in the non-coding region of the MYH9 gene or one or two copies of the MYH9 gene in order to prevent the development of CM in a genetically susceptible individual, such as the administration of an anti-malarial drug.

Glaucoma is a group of diseases of the optic nerve involving loss of retinal ganglion cells in a characteristic pattern of optic neuropathy. Raised intraocular pressure is a significant risk factor for developing glaucoma (above 22 mm Hg). Untreated glaucoma leads to permanent damage of the optic nerve and resultant visual field loss, which can progress to blindness. The loss of visual field often occurs gradually over a long time and may only be recognized when it is already quite advanced. Once lost, this damaged visual field can never be recovered. Glaucoma is more frequent in individuals of African ancestry as compared to Asian or European ancestry. Subjects with one or more risk alleles in the non-coding region of the MYH9 gene or who possess two copies of the MYH9 gene are genetically predisposed to the development or progression of glaucoma. Excessive contraction of structures in the eye can obstruct the outflow tract and cause raised intraocular pressure. Individuals are therefore screened or genotyped for the MYH9 gene to detect an increased risk of glaucoma. Those individuals positive for at least one risk allele in the non-coding region of the MYH9 gene can be monitored over several years through annual or semi-annual follow-up examinations to determine if intraocular pressure is outside of the normal range. Alternatively, evidence of optic neuropathy, such as an increased cup to disk raio, may be monitored. In instances, where a subject is genotyped to have one or more MYH9 risk alleles or one or two copies of the MYH9 gene, a prophylactic treatment is initiated, such as administration of anti-glaucoma eye drops or oral medications such as carbonic anhydrase inhibitors. In some instances the eye drops may contain beta-blockers, prostaglandin-like compounds, alpha agonists, epinephrine compounds, or the like, that reduce the production of aqueous humor. In severe cases of glaucoma it may be necessary for the subject to undergo surgery to control intraocular pressure, such as filtering surgery.

In the above diseases of disorders it is contemplated herein that the MYH9 gene plays an important role in a) the risk of developing the disease, b) the progression of the disease, or c) the development of nephropathy-associated disorders in conjunction with the primary disease. It is also contemplated herein that the MYH9 gene may play a significant role in the severity of the disease. In the above diseases it is possible to genotype an individual as already described in the section related to methods for detecting a genetic predisposition to renal disease to determine the MYH9 status of an individual. Based on the number of copies of the MYH9 gene and the presence of at least one risk allele in the non-coding region of the MYH9 gene it can be reasonably concluded that an individual with at least one risk allele in the non-coding region of the MYH9 gene or one or two copies of the MYH9 gene is at an elevated risk for a) developing the disease, b) the severity or progression of the disease, or c) developing nephropathy-associated complications in conjunction with the primary disease. Conversely, the presence of only one copy of the MYH9 gene and/or the presence of one or more protective alleles in the non-coding region of the MYH9 gene in a subject is considered to lower the genetic predisposition of the subject to one of more of the above diseases. Additionally, the term "one or more risk alleles of the non-coding region of the MYH9 gene" or "at least one risk allele in the non-coding region of the MYH9 gene" as used herein, includes at least one tag SNP identified in any of Tables 4-8 of the instant disclosure (labelled risk allele). Accordingly, any one of the risk alleles in the non-coding region of the MYH9 gene identified herein can be used to prepare an array comprising probes complementary to the at least one risk allele in the non-coding region of the MYH9 gene in order to characterize a biological sample with reference to the diseases discussed herein.

Molecular Methods

Generally, the methods disclosed herein involve an assessment of nucleic acid sequence. Molecular techniques of use in all of these methods are disclosed below.

Preparation of Nucleic Acids for Analysis:

Nucleic acid molecules can be prepared for analysis using any technique known to those skilled in the art. Generally, such techniques result in the production of a nucleic acid molecule sufficiently pure to determine the presence or absence of one or more variations at one or more locations in the nucleic acid molecule. Such techniques are described for example, in Sambrook, et al., Molecular Cloning: A Laboratory Manual (Cold Spring Harbor Laboratory, New York) (1989), and Ausubel, et al., Current Protocols in Molecular Biology (John Wiley and Sons, New York) (1997), incorporated herein by reference.

When the nucleic acid of interest is present in a cell, it can be necessary to first prepare an extract of the cell and then perform further steps, such as differential precipitation, column chromatography, extraction with organic solvents and the like, in order to obtain a sufficiently pure preparation of nucleic acid. Extracts can be prepared using standard techniques in the art, for example, by chemical or mechanical lysis of the cell. Extracts then can be further treated, for example, by filtration and/or centrifugation and/or with chaotropic salts such as guanidinium isothiocyanate or urea or with organic solvents such as phenol and/or $HCCl_3$ to denature any contaminating and potentially interfering proteins. When chaotropic salts are used, it can be desirable to remove the salts from the nucleic acid-containing sample. This can be accomplished using standard techniques in the art such as precipitation, filtration, size exclusion chromatography and the like.

In some instances, messenger RNA can be extracted from cells. Techniques and material for this purpose are known to those skilled in the art and can involve the use of oligo dT attached to a solid support such as a bead or plastic surface. In some embodiments, the mRNA can be reversed transcribed into cDNA using, for example, a reverse transcriptase enzyme. Suitable enzymes are commercially available from, for example, Invitrogen, Carlsbad Calif. Optionally, cDNA prepared from mRNA can also be amplified.

Amplification of Nucleic Acid Molecules:

Optionally, the nucleic acid samples obtained from the subject are amplified prior to detection. Target nucleic acids are amplified to obtain amplification products, including sequences from a haplotype block including a tag SNP, can be amplified from the sample prior to detection. Typically, DNA sequences are amplified, although in some instances RNA sequences can be amplified or converted into cDNA, such as by using RT PCR.

Any nucleic acid amplification method can be used. An example of in vitro amplification is the polymerase chain reaction (PCR), in which a biological sample obtained from a subject is contacted with a pair of oligonucleotide primers, under conditions that allow for hybridization of the primers to a nucleic acid molecule in the sample. The primers are extended under suitable conditions, dissociated from the template, and then re-annealed, extended, and dissociated to amplify the number of copies of the nucleic acid molecule. Other examples of in vitro amplification techniques include quantitative real-time PCR, strand displacement amplification (see U.S. Pat. No. 5,744,311); transcription-free isothermal amplification (see U.S. Pat. No. 6,033,881); repair chain reaction amplification (see PCT Publication NO. WO 90/01069); ligase chain reaction amplification (see EP-A-320 308); gap filling ligase chain reaction amplification (see U.S. Pat. No. 5,427,930); coupled ligase detection and PCR (see U.S. Pat. No. 6,027,889); and NASBA™ RNA transcription-free amplification (see U.S. Pat. No. 6,025,134).

In specific examples, the target sequences to be amplified from the subject include one or different haplotype blocks including a tag SNP, or a nucleotide sequence of interest including the tag SNP. In certain embodiments, target sequences containing one or more of SEQ ID NOs: 1-89, or a subset thereof, are amplified. In an embodiment, a single SNP with exceptionally high predictive value is amplified, or a nucleic acid encoding the SNP is amplified.

A pair of primers can be utilized in the amplification reaction. One or both of the primers can be labeled, for example with a detectable radiolabel, fluorophore, or biotin molecule. The pair of primers includes an upstream primer (which binds 5' to the downstream primer) and a downstream primer (which binds 3' to the upstream primer). The pair of primers used in the amplification reactions are selective primers which permit amplification of a size related marker locus. Primers can be selected to amplify a haplotype block including a tag SNP, or a nucleic acid including a tag SNP. Numerous primers can be designed by those of skill in the art simply by determining the sequence of the desired target region, for example, using well known computer assisted algorithms that select primers within desired parameters suitable for annealing and amplification.

If desired, an additional pair of primers can be included in the amplification reaction as an internal control. For example, these primers can be used to amplify a "housekeeping" nucleic acid molecule, and serve to provide confirmation of appropriate amplification. In another example, a target nucleic acid molecule including primer hybridization sites can be constructed and included in the amplification reactor. One of skill in the art will readily be able to identify primer pairs to serve as internal control primers.

Primer Design Strategy:

Increased use of polymerase chain reaction (PCR) methods has stimulated the development of many programs to aid in the design or selection of oligonucleotides used as primers for PCR. Four examples of such programs that are freely available via the Internet are: PRIMER™ by Mark Daly and Steve Lincoln of the Whitehead Institute (UNIX, VMS, DOS, and Macintosh), Oligonucleotide Selection Program by Phil Green and LaDeana Hiller of Washington University in St. Louis (UNIX, VMS, DOS, and Macintosh), PGEN™ by Yoshi (DOS only), and Amplify by Bill Engels of the University of Wisconsin (Macintosh only). Generally these programs help in the design of PCR primers by searching for bits of known repeated-sequence elements and then optimizing the $T_m$ by analyzing the length and GC content of a putative primer. Commercial software is also available and primer selection procedures are rapidly being included in most general sequence analysis packages.

Designing oligonucleotides for use as either sequencing or PCR primers to detect requires selection of an appropriate sequence that specifically recognizes the target, and then testing the sequence to eliminate the possibility that the oligonucleotide will have a stable secondary structure. Inverted repeats in the sequence can be identified using a repeat-identification or RNA-folding programs. If a possible stem structure is observed, the sequence of the primer can be shifted a few nucleotides in either direction to minimize the predicted secondary structure. When the amplified sequence is intended for subsequence cloning, the sequence of the oligonucleotide can also be compared with the sequences of both strands of the appropriate vector and insert DNA. A sequencing primer only has a single match to the target DNA. It is also advisable to exclude primers that have only a single mismatch with an undesired target DNA sequence. For PCR primers used to amplify genomic DNA, the primer sequence can be compared to the sequences in the GENBANK™ database to determine if any significant matches occur. If the oligonucleotide sequence is present in any known DNA sequence or, more importantly, in any known repetitive elements, the primer sequence should be changed.

Detection of Alleles:

The nucleic acids obtained from the sample can be genotyped to identify the particular allele present for a marker locus. A sample of sufficient quantity to permit direct detection of marker alleles from the sample can be obtained from the subject. Alternatively, a smaller sample is obtained from the subject and the nucleic acids are amplified prior to detection. Any target nucleic acid that is informative for a chromosome haplotype can be detected. Generally, the target nucleic acid corresponds to a tag SNP described above (SEQ ID NOs: 1-89). Any method of detecting a nucleic acid molecule can be used, such as hybridization and/or sequencing assays.

Hybridization is the binding of complementary strands of DNA, DNA/RNA, or RNA. Hybridization can occur when primers or probes bind to target sequences such as target sequences within genomic DNA. Probes and primers that are useful generally include nucleic acid sequences that hybridize (for example under high stringency conditions) with a nucleic acid sequence including the tag SNP of interest, but do not hybridize to a reference allele, or that hybridize to the reference allele, but do not hybridize to the tag SNP. Physical methods of detecting hybridization or binding of complementary strands of nucleic acid molecules, include but are not limited to, such methods as DNase I or chemical footprinting, gel shift and affinity cleavage assays, Southern and Northern blotting, dot blotting and light absorption detection procedures. The binding between a nucleic acid primer or probe and its target nucleic acid is frequently characterized by the temperature ($T_m$) at which 50% of the nucleic acid probe is melted from its target. A higher ($T_m$) means a stronger or more stable complex relative to a complex with a lower (Tm).

Generally, complementary nucleic acids form a stable duplex or triplex when the strands bind, (hybridize), to each other by forming Watson-Crick, Hoogsteen or reverse Hoogsteen base pairs. Stable binding occurs when an oligonucleotide molecule remains detectably bound to a target nucleic acid sequence under the required conditions.

Complementarity is the degree to which bases in one nucleic acid strand base pair with the bases in a second nucleic acid strand. Complementarity is conveniently described by percentage, that is, the proportion of nucleotides that form base pairs between two strands or within a specific region or domain of two strands. For example, if 10 nucleotides of a 15-nucleotide oligonucleotide form base pairs with a targeted region of a DNA molecule, that oligonucleotide is said to have 66.67% complementarity to the region of DNA targeted.

In the present disclosure, "sufficient complementarity" means that a sufficient number of base pairs exist between an oligonucleotide molecule and a target nucleic acid sequence (such as a tag SNP) to achieve detectable and specific binding. When expressed or measured by percentage of base pairs formed, the percentage complementarity that fulfills this goal can range from as little as about 50% complementarity to full (100%) complementary. In general, sufficient complementarity is at least about 50%, for example at least about 75% complementarity, at least about 90% complementarity, at least about 95% complementarity, at least about 98% complementarity, or even at least about 100% complementarity. The qualitative and quantitative considerations involved in establishing binding conditions that allow one skilled in the art to design appropriate oligonucleotides for use under the desired conditions is provided by Beltz et al. *Methods Enzymol* 100: 266-285, 1983, and by Sambrook et al. (ed.), *Molecular Cloning: A Laboratory Manual,* 2nd ed., vol. 1-3, Cold Spring Harbor Laboratory Press, Cold Spring Harbor, N.Y., 1989.

Hybridization conditions resulting in particular degrees of stringency will vary depending upon the nature of the hybridization method and the composition and length of the hybridizing nucleic acid sequences. Generally, the temperature of hybridization and the ionic strength (such as the Na+ concentration) of the hybridization buffer will determine the stringency of hybridization. Calculations regarding hybridization conditions for attaining particular degrees of stringency are discussed in Sambrook et al., (1989) *Molecular Cloning: a laboratory manual,* second edition, Cold Spring Harbor Laboratory, Plainview, N.Y. (chapters 9 and 11). The following is an exemplary set of hybridization conditions and is not limiting:

| Very High Stringency (detects sequences that share at least 90% complementarity) | |
| --- | --- |
| Hybridization: | 5x SSC at 65° C. for 16 hours |
| Wash twice: | 2x SSC at room temperature (RT) for 15 minutes each |
| Wash twice: | 0.5x SSC at 65° C. for 20 minutes each |

| High Stringency (detects sequences that share at least 80% complementarity) | |
| --- | --- |
| Hybridization: | 5x-6x SSC at 65° C.-70° C. for 16-20 hours |
| Wash twice: | 2x SSC at RT for 5-20 minutes each |
| Wash twice: | 1x SSC at 55° C.-70° C. for 30 minutes each |

| Low Stringency (detects sequences that share at least 50% complementarity) | |
| --- | --- |
| Hybridization: | 6x SSC at RT to 55° C. for 16-20 hours |
| Wash at least twice: | 2x-3x SSC at RT to 55° C. for 20-30 minutes each. |

Methods for labeling nucleic acid molecules so they can be detected are well known. Examples of such labels include non-radiolabels and radiolabels. Non-radiolabels include, but are not limited to an enzyme, chemiluminescent compound, fluorescent compound (such as FITC, Cy3, and Cy5), metal complex, hapten, enzyme, colorimetric agent, a dye, or combinations thereof. Radiolabels include, but are not limited to, $^{125}$I, $^{32}$P and $^{35}$S. For example, radioactive and fluorescent labeling methods, as well as other methods known in the art, are suitable for use with the present disclosure. In one example, primers used to amplify the subject's nucleic acids are labeled (such as with biotin, a radiolabel, or a fluorophore). In another example, amplified target nucleic acid samples are end-labeled to form labeled amplified material. For example, amplified nucleic acid molecules can be labeled by including labeled nucleotides in the amplification reactions.

Nucleic acid molecules corresponding to one or more tag SNPs or haplotype blocks including the tag SNP can also be detected by hybridization procedures using a labeled nucleic acid probe, such as a probe that detects only one alternative allele at a marker locus. Most commonly, the target nucleic acid (or amplified target nucleic acid) is separated based on size or charge and transferred to a solid support. The solid support (such as membrane made of nylon or nitrocellulose) is contacted with a labeled nucleic acid probe, which hybridizes to it complementary target under suitable hybridization conditions to form a hybridization complex.

Hybridization conditions for a given combination of array and target material can be optimized routinely in an empirical manner close to the $T_m$ of the expected duplexes, thereby maximizing the discriminating power of the method. For example, the hybridization conditions can be selected to permit discrimination between matched and mismatched oligonucleotides. Hybridization conditions can be chosen to correspond to those known to be suitable in standard procedures for hybridization to filters (and optionally for hybridization to arrays). In particular, temperature is controlled to substantially eliminate formation of duplexes between sequences other than an exactly complementary allele of the selected marker. A variety of known hybridization solvents can be employed, the choice being dependent on considerations known to one of skill in the art (see U.S. Pat. No. 5,981,185).

Once the target nucleic acid molecules have been hybridized with the labeled probes, the presence of the hybridization complex can be analyzed, for example by detecting the complexes.

Methods for detecting hybridized nucleic acid complexes are well known in the art. In one example, detection includes detecting one or more labels present on the oligonucleotides, the target (e.g., amplified) sequences, or both. Detection can include treating the hybridized complex with a buffer and/or a conjugating solution to effect conjugation or coupling of the hybridized complex with the detection label, and treating the conjugated, hybridized complex with a detection reagent. In one example, the conjugating solution includes streptavidin alkaline phosphatase, avidin alkaline phosphatase, or horseradish peroxidase. Specific, non-limiting examples of conjugating solutions include streptavidin alkaline phosphatase, avidin alkaline phosphatase, or horseradish peroxidase. The conjugated, hybridized complex can be treated with a detection reagent. In one example, the detection reagent includes enzyme-labeled fluorescence reagents or calorimetric reagents. In one specific non-limiting example, the detection reagent is enzyme-labeled fluorescence reagent (ELF) from Molecular Probes, Inc. (Eugene, Oreg.). The hybridized complex can then be placed on a detection device, such as an ultraviolet (UV) transilluminator (manufactured by UVP, Inc. of Upland, Calif.). The signal is developed and the increased signal intensity can be recorded with a recording device, such as a charge coupled device (CCD) camera (manufactured by Photometrics, Inc. of Tucson, Ariz.). In particular examples, these steps are not performed when radiolabels are used. In particular examples, the method further includes quantification, for instance by determining the amount of hybridization.

Allele Specific PCR:

Allele-specific PCR differentiates between target regions differing in the presence of absence of a variation or polymorphism. PCR amplification primers are chosen based upon their complementarity to the target sequence, such as nucleic acid sequence in a haplotype block including a tag SNP, a specified region of an allele including a tag SNP, or to the tag SNP itself. The primers bind only to certain alleles of the target sequence. This method is described by Gibbs, *Nucleic Acid Res.* 17:12427 2448, 1989, herein incorporated by reference.

Allele Specific Oligonucleotide Screening Methods:

Further screening methods employ the allele-specific oligonucleotide (ASO) screening methods (e.g. see Saiki et al., *Nature* 324:163-166, 1986). Oligonucleotides with one or more base pair mismatches are generated for any particular allele or haplotype block. ASO screening methods detect mismatches between one allele (or haplotype block) in the target genomic or PCR amplified DNA and the other allele (or haplotype block), showing decreased binding of the oligonucleotide relative to the second allele (i.e. the other allele) oligonucleotide. Oligonucleotide probes can be designed that under low stringency will bind to both polymorphic forms of the allele, but which at high stringency, only bind to the allele to which they correspond. Alternatively, stringency conditions can be devised in which an essentially binary response is obtained, i.e., an ASO corresponding to a variant form of the target gene will hybridize to that allele (haplotype block), and not to the reference allele (haplotype block).

Ligase Mediated Allele Detection Method:

Ligase can also be used to detect point mutations, such as the tag SNPs disclosed herein, in a ligation amplification reaction (e.g. as described in Wu et al., *Genomics* 4:560-569, 1989). The ligation amplification reaction (LAR) utilizes amplification of specific DNA sequence using sequential rounds of template dependent ligation (e.g. as described in Wu, supra, and Barany, *Proc. Nat. Acad. Sci.* 88:189-193, 1990).

Denaturing Gradient Gel Electrophoresis:

Amplification products generated using the polymerase chain reaction can be analyzed by the use of denaturing gradient gel electrophoresis. Different alleles (haplotype blocks) can be identified based on the different sequence-dependent melting properties and electrophoretic migration of DNA in solution. DNA molecules melt in segments, termed melting domains, under conditions of increased temperature or denaturation. Each melting domain melts cooperatively at a distinct, base-specific melting temperature ($T_M$). Melting domains are at least 20 base pairs in length, and can be up to several hundred base pairs in length.

Differentiation between alleles (haplotype blocks) based on sequence specific melting domain differences can be assessed using polyacrylamide gel electrophoresis, as described in Chapter 7 of Erlich, ed., PCR Technology, Principles and Applications for DNA Amplification, W. H. Freeman and Co., New York (1992).

Generally, a target region to be analyzed by denaturing gradient gel electrophoresis is amplified using PCR primers flanking the target region. The amplified PCR product is applied to a polyacrylamide gel with a linear denaturing gradient as described in Myers et al., *Meth. Enzymol.* 155:501-527, 1986, and Myers et al., in Genomic Analysis, A Practical Approach, K. Davies Ed. IRL Press Limited, Oxford, pp. 95 139, 1988. The electrophoresis system is maintained at a temperature slightly below the Tm of the melting domains of the target sequences.

In an alternative method of denaturing gradient gel electrophoresis, the target sequences can be initially attached to a stretch of GC nucleotides, termed a GC clamp, as described in Chapter 7 of Erlich, supra. In one example, at least 80% of the nucleotides in the GC clamp are either guanine or cytosine. In another example, the GC clamp is at least 30 bases long. This method is particularly suited to target sequences with high $T_m$'s.

Generally, the target region is amplified by polymerase chain reaction. One of the oligonucleotide PCR primers carries at its 5' end, the GC clamp region, at least 30 bases of the GC rich sequence, which is incorporated into the 5' end of the target region during amplification. The resulting amplified target region is run on an electrophoresis gel under denaturing gradient conditions. DNA fragments differing by a single base change will migrate through the gel to different positions, which can be visualized by ethidium bromide staining.

Temperature Gradient Gel Electrophoresis:

Temperature gradient gel electrophoresis (TGGE) is based on the same underlying principles as denaturing gradient gel electrophoresis, except the denaturing gradient is produced by differences in temperature instead of differences in the concentration of a chemical denaturant. Standard TGGE utilizes an electrophoresis apparatus with a temperature gradient running along the electrophoresis path. As samples migrate through a gel with a uniform concentration of a chemical denaturant, they encounter increasing temperatures. An alternative method of TGGE, temporal temperature gradient gel electrophoresis (TTGE or tTGGE) uses a steadily increasing temperature of the entire electrophoresis gel to achieve the same result. As the samples migrate through the gel the temperature of the entire gel increases, leading the samples to encounter increasing temperature as they migrate through the gel. Preparation of samples, including PCR amplification with incorporation of a GC clamp, and visualization of products are the same as for denaturing gradient gel electrophoresis.

Single-Strand Conformation Polymorphism Analysis:

Target sequences, such as alleles or haplotype blocks can be differentiated using single-strand conformation polymorphism analysis, which identifies base differences by alteration in electrophoretic migration of single stranded PCR products, for example as described in Orita et al., *Proc. Nat. Acad. Sci.* 85:2766-2770, 1989. Amplified PCR products can be generated as described above, and heated or otherwise denatured, to form single stranded amplification products. Single-stranded nucleic acids can refold or form secondary structures which are partially dependent on the base sequence. Thus, electrophoretic mobility of single-stranded amplification products can detect base-sequence difference between alleles or haplotype blocks.

Chemical or Enzymatic Cleavage of Mismatches:

Differences between target sequences, such as alleles or haplotype blocks, can also be detected by differential chemical cleavage of mismatched base pairs, for example as described in Grompe et al., *Am. J. Hum. Genet.* 48:212-222, 1991. In another method, differences between target sequences, such as alleles or haplotype blocks, can be detected by enzymatic cleavage of mismatched base pairs, as described in Nelson et al., Nature Genetics 4:11-18, 1993. Briefly, genetic material from an animal and an affected family member can be used to generate mismatch free heterohybrid DNA duplexes. As used herein, "heterohybrid" means a DNA duplex strand comprising one strand of DNA from one animal, and a second DNA strand from another animal, usually an animal differing in the phenotype for the trait of interest. Positive selection for heterohybrids free of mismatches allows determination of small insertions, deletions or other polymorphisms.

Non-Gel Systems:

Other possible techniques include non-gel systems such as TaqMan™ (Perkin Elmer). In this system oligonucleotide PCR primers are designed that flank the mutation in question and allow PCR amplification of the region. A third oligonucleotide probe is then designed to hybridize to the region containing the base subject to change between different alleles of the gene. This probe is labeled with fluorescent dyes at both the 5' and 3' ends. These dyes are chosen such that while in this proximity to each other the fluorescence of one of them is quenched by the other and cannot be detected. Extension by Taq DNA polymerase from the PCR primer positioned 5' on the template relative to the probe leads to the cleavage of the dye attached to the 5' end of the annealed probe through the 5' nuclease activity of the Taq DNA polymerase. This removes the quenching effect allowing detection of the fluorescence from the dye at the 3' end of the probe. The discrimination between different DNA sequences arises through the fact that if the hybridization of the probe to the template molecule is not complete (there is a mismatch of some form) the cleavage of the dye does not take place. Thus only if the nucleotide sequence of the oligonucleotide probe is completely complimentary to the template molecule to which it is bound will quenching be removed. A reaction mix can contain two different probe sequences each designed against different alleles that might be present thus allowing the detection of both alleles in one reaction.

Non-PCR Based Allele Detection:

The identification of a DNA sequence can be made without an amplification step, based on polymorphisms including restriction fragment length polymorphisms in a subject and a control, such as a family member. Hybridization probes are generally oligonucleotides which bind through complementary base pairing to all or part of a target nucleic acid. Probes typically bind target sequences lacking complete complementarity with the probe sequence depending on the stringency of the hybridization conditions. The probes can be labeled directly or indirectly, such that by assaying for the presence or absence of the probe, one can detect the presence or absence of the target sequence. Direct labeling methods include radioisotope labeling, such as with $^{32}$P or $^{35}$S. Indirect labeling methods include fluorescent tags, biotin complexes which can be bound to avidin or streptavidin, or peptide or protein tags. Visual detection methods include photoluminescents, Texas red, rhodamine and its derivatives, red leuco dye and 3,3',5,5'-tetramethylbenzidine (TMB), fluorescein, and its derivatives, dansyl, umbelliferone and the like or with horse radish peroxidase, alkaline phosphatase and the like.

Hybridization probes include any nucleotide sequence capable of hybridizing to a nucleic acid sequence wherein a polymorphism is present that is associated with FSGS or hypertensive end stage kidney disease, such as a tag SNP, and thus defining a genetic marker, including a restriction fragment length polymorphism, a hypervariable region, repetitive element, or a variable number tandem repeat. Hybridization probes can be any gene or a suitable analog. Further suitable hybridization probes include exon fragments or portions of cDNAs or genes known to map to the relevant region of the chromosome.

Exemplary tandem repeat hybridization probes for use in the methods disclosed are those that recognize a small number of fragments at a specific locus at high stringency hybridization conditions, or that recognize a larger number of fragments at that locus when the stringency conditions are lowered.

Arrays for Detecting Nucleic Acid:

In particular examples involving genotyping of multiple marker loci, the methods can be performed using an array that includes a plurality of markers. Such arrays can include nucleic acid molecules. In one example, the array includes nucleic acid oligonucleotide probes that can hybridize to one or more alleles.

Arrays can be used to detect the presence of amplified sequences including one or more tag SNPs of interest using specific oligonucleotide probes. In one example, a set of oligonucleotide probes is attached to the surface of a solid support for use in detection of marker alleles that define haplotypes that determine a genetic predisposition to FSGS or hypertensive End stage kidney disease. Additionally, if an internal control nucleic acid sequence was amplified in the amplification reaction (see above), an oligonucleotide probe can be included to detect the presence of this amplified nucleic acid molecule. The oligonucleotide probes bound to the array can specifically bind sequences amplified in the amplification reaction (such as under high stringency conditions).

The methods and apparatus in accordance with the present disclosure takes advantage of the fact that under appropriate conditions oligonucleotides form base-paired duplexes with nucleic acid molecules that have a complementary base sequence. The stability of the duplex is dependent on a number of factors, including the length of the oligonucleotides, the base composition, and the composition of the solution in which hybridization is effected. The effects of base composition on duplex stability can be reduced by carrying out the hybridization in particular solutions, for example in the presence of high concentrations of tertiary or quaternary amines.

The thermal stability of the duplex is also dependent on the degree of sequence similarity between the sequences. By carrying out the hybridization at temperatures close to the anticipated $T_m$'s of the type of duplexes expected to be formed between the target sequences and the oligonucleotides bound to the array, the rate of formation of mismatched duplexes can be substantially reduced.

The length of each oligonucleotide sequence employed in the array can be selected to optimize binding to a specific allele of a marker locus associated with ALS. An optimum length for use with a particular marker nucleic acid sequence under specific screening conditions can be determined empirically. Thus, the length for each individual element of the set of oligonucleotide sequences included in the array can be optimized for screening. In one example, oligonucleotide probes are from about 20 to about 35 nucleotides in length or about 25 to about 40 nucleotides in length.

The oligonucleotide probe sequences forming the array can be directly linked to the support, for example via the 5'- or 3'-end of the probe. In one example, the oligonucleotides are bound to the solid support by the 5' end. However, one of skill in the art can determine whether the use of the 3' end or the 5' end of the oligonucleotide is suitable for bonding to the solid support. In general, the internal complementarity of an oligonucleotide probe in the region of the 3' end and the 5' end determines binding to the support. Alternatively, the oligonucleotide probes can be attached to the support by sequences such as oligonucleotides or other molecules that serve as spacers or linkers to the solid support.

In particular examples, the array is a microarray formed from glass (silicon dioxide). Suitable silicon dioxide types for the solid support include, but are not limited to: aluminosilicate, borosilicate, silica, soda lime, zinc titania and fused silica (for example see Schena, *Micraoarray Analysis*. John Wiley & Sons, Inc, Hoboken, N.J., 2003). The attachment of nucleic acids to the surface of the glass can be achieved by methods known in the art, for example by surface treatments that form from an organic polymer. Particular examples include, but are not limited to: polypropylene, polyethylene, polybutylene, polyisobutylene, polybutadiene, polyisoprene, polyvinylpyrrolidine, polytetrafluroethylene, polyvinylidene difluroide, polyfluoroethylene-propylene, polyethylenevinyl alcohol, polymethylpentene, polycholorotrifluoroethylene, polysulfornes, hydroxylated biaxially oriented polypropylene, aminated biaxially oriented polypropylene, thiolated biaxially oriented polypropylene, etyleneacrylic acid, thylene methacrylic acid, and blends of copolymers thereof (see U.S. Pat. No. 5,985,567), organosilane compounds that provide chemically active amine or aldehyde groups, epoxy or polylysine treatment of the microarray. Another example of a solid support surface is polypropylene.

In general, suitable characteristics of the material that can be used to form the solid support surface include: being amenable to surface activation such that upon activation, the surface of the support is capable of covalently attaching a biomolecule such as an oligonucleotide thereto; amenability to "in situ" synthesis of biomolecules; being chemically inert such that at the areas on the support not occupied by the oligonucleotides are not amenable to non-specific binding, or when non-specific binding occurs, such materials can be readily removed from the surface without removing the oligonucleotides.

In one example, the surface treatment is amine-containing silane derivatives. Attachment of nucleic acids to an amine surface occurs via interactions between negatively charged phosphate groups on the DNA backbone and positively charged amino groups (Schena, Micraoarray Analysis. John Wiley & Sons, Inc, Hoboken, N.J., 2003). In another example, reactive aldehyde groups are used as surface treatment. Attachment to the aldehyde surface is achieved by the addition of 5'-amine group or amino linker to the DNA of interest. Binding occurs when the nonbonding electron pair on the amine linker acts as a nucleophile that attacks the electropositive carbon atom of the aldehyde group.

A wide variety of array formats can be employed in accordance with the present disclosure. One example includes a linear array of oligonucleotide bands, generally referred to in the art as a dipstick. Another suitable format includes a two-dimensional pattern of discrete cells (such as 4096 squares in a 64 by 64 array). As is appreciated by those skilled in the art, other array formats including, but not limited to slot (rectangular) and circular arrays are equally suitable for use (see U.S. Pat. No. 5,981,185). In one example, the array is formed on a polymer medium, which is a thread, membrane or film. An example of an organic polymer medium is a polypropylene sheet having a thickness on the order of about 1 mil. (0.001 inch) to about 20 mil., although the thickness of the film is not critical and can be varied over a fairly broad range. Biaxially oriented polypropylene (BOPP) films are also suitable in this regard; in addition to their durability, BOPP films exhibit a low background fluorescence. In a particular example, the array is a solid phase, Allele-Specific Oligonucleotides (ASO) based nucleic acid array.

The array formats of the present disclosure can be included in a variety of different types of formats. A "format" includes any format to which the solid support can be affixed, such as microtiter plates, test tubes, inorganic sheets, dipsticks, and the like. For example, when the solid support is a polypropylene thread, one or more polypropylene threads can be affixed to a plastic dipstick-type device; polypropylene membranes can be affixed to glass slides. The particular format is, in and of itself, unimportant. All that is necessary is that the solid support can be affixed thereto without affecting the functional behavior of the solid support or any biopolymer absorbed thereon, and that the format (such as the dipstick or slide) is stable to any materials into which the device is introduced (such as clinical samples and hybridization solutions).

The arrays of the present disclosure can be prepared by a variety of approaches. In one example, oligonucleotide or protein sequences are synthesized separately and then attached to a solid support (see U.S. Pat. No. 6,013,789). In another example, sequences are synthesized directly onto the support to provide the desired array (see U.S. Pat. No. 5,554,501). Suitable methods for covalently coupling oligonucleotides and proteins to a solid support and for directly synthesizing the oligonucleotides or proteins onto the support are known to those working in the field; a summary of suitable methods can be found in Matson et al., *Anal. Biochem.* 217: 306-10, 1994. In one example, the oligonucleotides are synthesized onto the support using conventional chemical techniques for preparing oligonucleotides on solid supports (such as see PCT Publication No. WO 85/01051 and PCT Publication No. WO 89/10977, or U.S. Pat. No. 5,554,501).

A suitable array can be produced using automated means to synthesize oligonucleotides in the cells of the array by laying down the precursors for the four bases in a predetermined pattern. Briefly, a multiple-channel automated chemical delivery system is employed to create oligonucleotide probe populations in parallel rows (corresponding in number to the number of channels in the delivery system) across the substrate. Following completion of oligonucleotide synthesis in a first direction, the substrate can then be rotated by 90° to permit synthesis to proceed within a second (2°) set of rows that are now perpendicular to the first set. This process creates a multiple-channel array whose intersection generates a plurality of discrete cells.

In particular examples, the oligonucleotide probes on the array include one or more labels, which permit detection of oligonucleotide probe:target sequence hybridization complexes.

Kits

The present disclosure provides for kits that can be used to detect a genetic predisposition to FSGS or hypertensive end stage kidney disease.

In other embodiments, the present disclosure provide kits that can be used to detect a genetic predisposition to glaucoma, asthma, sickle cell anemia, lacunar stroke, cerebral malaria, diabetes, hypertension, human immunodeficiency virus, systemic lupus erythematosus, preeclampsia or systemic sclerosis. In a further embodiment, the present disclosure provides a kit for genotyping a MYH9 gene in an individual, a biological sample, or organ for transplantation. The disclosed kits can include a binding molecule, such as an oligonucleotide probe that selectively hybridizes to an allele of a haplotype block including a tag SNP. In one example, the kit includes the isolated oligonucleotide probes that specifically bind to one or more of the nucleic acid sequences set forth as SEQ ID NOs: 1-89, or probes for one, two, three, four, five, six, seven, eight, nine, ten, eleven, twelve, thirteen, fourteen or fifteen of the nucleic acid sequences set forth of SEQ ID NOs: 1-89, wherein these sequences include the tag SNP associated with renal disease.

Alternatively or additionally, the kits can include one or more isolated primers or primer pairs for amplifying a target nucleic acid, such as a haplotype including a tag SNP. For example, the kit can include primers for amplifying a haplotype including one, two, three, four, five, six, seven, eight, nine, ten, eleven, twelve, thirteen, fourteen or fifteen tag SNPs, wherein the sequence includes the tag SNP associated with FSGS.

The kit can further include one or more of a buffer solution, a conjugating solution for developing the signal of interest, or a detection reagent for detecting the signal of interest, each in separate packaging, such as a container. In another example, the kit includes a plurality of size-associated marker target nucleic acid sequences for hybridization with a detection array. The target nucleic acid sequences can include oligonucleotides such as DNA, RNA, and peptide-nucleic acid, or can include PCR fragments. The kit can also include instructions in a tangible form, such as written instructions or in a computer-readable format.

The disclosure is illustrated by the following non-limiting Examples.

EXAMPLES

Focal segmental glomerulosclerosis (FSGS), the most common cause of primary adult nephrotic syndrome and the glomerular disease associated with HIV infection, is more common among individuals of African ancestry. The genetic basis for this racial predilection had not been previously determined.

Genome-wide association studies have recently revealed genomic regions or specific genes associated with many diseases, including diabetes (Gudmundsson et al., Nat Genet 2007; 39(8):977-83; Todd et al., Nat Genet 2007; 39(7):857-64; Scott et al., Science 2007; 316(5829):1341-5) diabetic nephropathy (Iyengar et al., Diabetes 2007; 56(6):1577-85; Schelling et al., Genome-Wide Scan for Estimated GFR in Multi-Ethnic Diabetic Populations: The Family Investigation of Nephropathy and Diabetes. Diabetes 2007), prostate cancer (Murabito et al, BMC Med Genet 2007; 8 Suppl 1:S6; Yeager et al., Nat Genet 2007; 39(5):645-9) and breast cancer (Murabito et al., supra). These reports have generally identified common alleles with small individual risks (ORs from 1.1 to 1.4), which may have a large impact on overall health burden, but explain only a small portion of the disease burden. A second strategy of genetic mapping by admixtures linkage disequilibrium (MALD) has successfully identified a genomic region associated with prostate cancer (Freedman et al., Proc Natl Acad Sci USA 2006; 103(38):14068-73) subsequently replicated by a genome-wide association study (Yeager et al., supra), as well as genes associated with hypertension (Zhu et al., PLoS ONE 2007; 2(11):e1244; Zhu et al., Nat Genet 2005; 37(2):177-81), multiple sclerosis (Reich et al., Nat Genet 2005; 37(10):1113-8), and variation in cytokine levels (Reich et al., Am J Hum Genet 2007; 80(4):716-26). The MALD method is most robust for diseases that have large racial or ethnic disparities not fully explained by environmental factors and that occur in populations that have undergone recent admixture between ancestral populations within the past 10-20 generations, e.g. Hispanic-Americans and African-Americans (Smith and O'Brien, Nat Rev Genet 2005; 6(8):623-32; Smith et al., Am J Hum Genet 2004; 74:1001-13; Patterson et al., Am J Hum Genet 2004; 74(5):979-1000).

A mapping by admixture disequilibrium (MALD) genome scan was performed on 190 African-American sporadic and HIV-associated FSGS cases and 222 controls. Additional single nucleotide polymorphisms (SNPs) for an implicated region were typed in FSGS cases and controls and in African-American end-stage kidney disease attributed to hypertension or diabetes mellitus type 2. As described below, results obtained from a MALD scan identified a region of chromosome 22 with a highly significant genome-wide logarithm of the odds (LOD) score of 9.2, with a peak LOD of 13.6. The implicated region is centered on the non-muscle myosin HA heavy chain gene MYH9. SNPs within MYH9 were strongly associated with FSGS, with the most significant associations for 3 correlated SNPs within intron 23 ($10^{-18}>P>10^{-20}$ and $4<OR<5$, recessive for the African ancestry allele), and for a haplotype containing these SNPs (OR=5.0, P=$4\times10^{-23}$, recessive model). The attributable fraction for carrying this haplotype was 100% for HIV-associated FSGS and 72% for sporadic FSGS. This haplotype was also associated with hypertensive end-stage kidney disease among African-Americans (OR=1.7, P=0.003). The results presented herein demonstrate that the increased burden of FSGS and hypertensive end-stage kidney disease among African-Americans is substantially due to one or more MYH9 genetic risk alleles frequent on African origin haplotypes but much less frequent on European-origin haplotypes.

Example 1

Materials and Methods

Subjects:
Kidney biopsy-confirmed idiopathic FSGS or HIV-1-associated FSGS cases were enrolled from 22 academic medical centers in the USA as part of the NIH FSGS Genetic Study (Orloff et al., Physiol Genomics 2005; 21(2):212-21; McKenzie et al., J Am Soc Nephrol 2007; 18(11):2987-95). The study enrolled 377 subjects with idiopathic or HIV-1-associated FSGS and 919 control subjects without known kidney disease. Patients with one or more family members with FSGS were excluded. Geographic ancestry was based on self-report. It has been previously reported that there is no evidence of population substructure among FSGS cases and controls for African-Americans (Orloff et al., supra).

The FSGS study population consisted of three case groups: 1) 130 European-Americans without HIV-1 infection; 2) 194 African-Americans without HIV-1 infection; 3) 53 African-Americans with HIV-1 infection and with kidney biopsies that were consistent with HIV-1-associated nephropathy, with collapse of glomerular capillaries and podocyte hyperplasia. Age of kidney biopsy, available for all cases, was taken as a proxy for age of FSGS onset. The mean age of European-American and African-American FSGS cases was 35 and 34 years, respectively.

The control group included 393 African-American and 281 European-Americans adults who were HIV-1 uninfected. The 245 HIV-1-infected control subjects were African-American subjects enrolled in the AIDS Link to the Intravenous Drug Experience (ALIVE) cohort from Baltimore, Md. who did not have FSGS or evidence of nephrotic syndrome after at least 8 years of HIV-1 infection. The absence of kidney disease was defined as having normal serum creatinine (≤1.4 mg/dL) and lack of proteinuria (urine protein to creatinine ratio <0.5). This group represents a hypernormal sample, in that they are drawn from the African-American population at risk for HIV-1-associated FSGS, have been HIV-1 infected for at least 8 years, and yet lack evidence of FSGS or proteinuria. Blood samples from normal donors lacking a history of kidney disease were obtained.

The extension cohort included unrelated African-Americans with ESKD attributed to hypertension (n=417) or type II diabetes (n=284) and 192 African-American control subjects without kidney disease from the southeastern United States, using previously reported diagnostic criteria (Freedman et al., J Am Soc Nephrol 2004; 15(10):2719-27; Bowden et al., Kidney Int 2004; 66(4):1517-26).

Genotyping:

The ParAllele™ platform (Affymetrix, Santa Clara, Calif.) was used to genotype FSGS cases and controls. In this study 1331 informative MALD markers were genotyped that are not known to be in LD in parental populations (Bowden et al. Kidney Int 2004; 66(4):1517-26). Of these, 59 were excluded from analysis because they either did not meet Hardy-Weinberg expectations for genotype frequencies or because allele frequencies were different from those expected. Parental population allele counts for admixture analysis were compiled from our MALD map construction data (Smith et al., Am J Hum Genet 2001; 69(5):1080-94) and later analyses (Freedman et al., Proc Natl Acad Sci USA 2006; 103(38): 14068-73); hapmap data was used for selected markers (Thorisson et al., Genome Res 2005; 15(11):1592-3). MYH9 SNPs were genotyped using the TAQMAN® platform (Applied Biosystems, Foster City, Calif.).

MALD Analysis:

The ANCESTRYMAP® program was used to scan the genome for regions of African ancestry that differ significantly from the genome average in cases and from the same locus in controls (Smith et al., Am J Hum Genet 2004; 74:1001-13). From current estimates of FSGS prevalence in African-Americans and European-Americans (Kopp et al., Kidney Int Suppl 2003(83):S43-9; Kitiyakahara et al., Semin Nephrol 2003; 23(2):172-82) and the prevalence of HIV-1 infection in the study populations, an 8-fold increase in the risk of FSGS in individuals of African ancestry (carrying two African chromosomes) was assumed, as compared to those of European ancestry. Under the log-additive model used by ANCESTRYMAP®, this implies an approximately 2.8 fold increase in risk per African chromosome that was used in the analyses presented. Additional analyses considered alternate risk models ranging from 0.25 to 4.

Significance was assessed by logarithm of the odds (LOD) scores reported by ANCESTRYMAP. The program was used with 100 burn-in and 200 follow-on iterations for all Markov Chain-Monte Carlo runs as recommended (Patterson et al., Am J Hum Genet 2004; 74(5):979-1000). Case-control LOD scores were calculated based on the comparison of local odds of disease in cases and controls, and locus-genome LOD scores were calculated based on a comparison of the estimated percent ancestry at a locus and the cases' genome-wide ancestry average. A LOD score for genome-wide significance was also calculated; a score greater than 2.0 was considered significant (Reich and Patterson, Philos Trans R Soc Lond B Biol Sci 2005; 360(1460):1605-7). The 95% credible interval for the location of the FSGS disease gene was derived from the locus-genome LOD-score based relative probability distribution (Yeager et al., Nat Genet 2007; 39(5):645-9). Calculations for the 95% credible interval were made using the maldmap package in R version 2.6.1 (R Foundation for Statistical Computing, Vienna, Austria).

Statistical Analysis of SNP Associations:

Phenotype/genotype associations were tested using dominant, recessive, and allele models, which are statistically agnostic with respect to the choice of reference allele. P values were determined by Fisher's exact test (FET); all tests are two-sided. To extrapolate from the case-control data to population data for estimation of the attributable fraction (AF) and explained fraction (EF) (Smith et al., supra) an FSGS prevalence of 2/1000 was assumed for HIV-1 uninfected African Americans, and 1/2000 for HIV-1 uninfected European Americans; the 10% prevalence of FSGS among HIV-1 infected subjects that prevailed prior to effective antiretroviral therapy was assumed, as our HIV-1 infected cases and controls were collected in this era.

Distinguishing Short Range (Fine Mapping) from Long Range (Admixture) Associations:

To separate the long range effects of admixture linkage disequilibrium from the short range (typically 10 to 50 kb) effects of local haplotype structure in the ancestral populations, ANCESTRYMAP® was used to estimate the probabilities that a particular individual carries zero, one, or two African chromosomal segments at a given locus. The fraction of the associations due to chromosomal African ancestry was estimated by comparing the reduction of sample deviance in a logistic regression for the SNP genotypes alone with that for a logistic regression with the SNP genotype and the estimate of chromosomal ancestry taken as covariates. A second test repeated the SNP analysis, limited to African-American cases and controls carrying two African chromosome segments at the tested locus with probability greater than 95%.

For 893 cases and controls in the ESKD replication and extension study, the individual subjects' overall admixture fractions was estimated by maximum likelihood with the program FRAPPE® (Tang et al., Genet Epidemiol 2005; 28(4):289-301 using 67 ancestry-informative markers, and tested whether admixture fraction contributed significantly to MYH9 associations with ESKD by including this estimate as a logistic regression covariate along with the SNP and haplotype variables.

Haplotype Inference:

Haplotype blocks were defined from HapMap data (The International HapMap Project. Nature 2003; 426(6968):789-96) by the confidence interval method (Gabriel et al., Science 2002; 296(5576):2225-9), but considered haplotypes both within and beyond HapMap blocks. Haplotypes were inferred by an in-house implementation of the expectation-maximization (EM) algorithm. To determine whether haplotypes can be inferred robustly beyond blocks, this program measures reliability of inferences as the uncertainty (calculated as entropy) of bootstrap replicated haplotype inferences. Genetic associations with inferred haplotypes were confirmed with haplotypes inferred by PHASE 2.1.

Localization of Myosin IIA in Podocytes:

Mouse glomeruli cryosections were immunostained for myosin IIA and synaptopodin, and visualized by confocal microscopy. Cultured human podocytes (Saleem et al., J Am Soc Nephrol 2002; 13(3):630-8) were immunostained for myosin IIA and actin (using phalloidin), synaptopodin, and nephrin and visualized by confocal microscopy.

Example 2

MALD Survey

The MALD survey of 1272 SNPs, typed on 190 African-American cases and 222 African-American controls, yielded a genome-wide LOD score of 9.2. There was a single prominent peak located on chromosome 22, with a LOD score of 13.6 (FIG. 1A, B), and a pronounced elevation of African ancestry in FSGS cases, with 92% carrying African-inherited chromosomes as compared to a genome average of 81% (FIG. 1A). The 95% credible interval for the MALD peak extended along chromosome 22q13.1 from coordinates 34.42 Mb to 35.65 Mb (FIG. 1C).

The apex of the MALD peak occurred at the MALD mapping SNP rs735853, located in an intron close to the 3' end of MYH9, which encodes non-muscle myosin heavy chain IIA. The gene is expressed in glomerular podocytes and mutations have been previously associated with glomerulonephritis (Arrondel et al., J Am Soc Nephrol 2002; 13(1):65-74). The 95% confidence interval of the MALD peak contains 39 other genes, but an analysis showed their functions appear largely unrelated to glomerular function. Hence, one or more genetic variations in MYH9, with substantial allele frequency differences between Africans and Europeans, appeared to account for the chromosome 22 MALD association with FSGS.

For the MALD peak at SNP rs735853, the African-American major C allele showed a very strong susceptibility effect for FSGS (OR=9.09; CI 4.0, 25.0; P=5×10$^{-13}$ (Table 1). The frequency of the susceptible C allele was 88.3% in African-Americans and 51.9% in European-Americans. An 23 additional SNPs were genotyped in MYH9, selected by the following criteria: a) a pronounced frequency difference between reference African (YRI) and European (CEU) populations; b) possible functional significance, and/or c) strong but not absolute linkage disequilibrium with SNPs with highly significant FSGS associations. Of these, two codon changing SNPs (rs2269525 and rs34292387) previously associated with rare inherited forms of MYH9-associated glomerulonephritis were monomorphic in this study population. Four additional SNPs (rs710181, rs9619601, rs8137674, and rs7285745) had minor allele frequency ≤3% in African-Americans and were not analyzed further. Of the remaining 17 SNPs, all but three showed significant association with FSGS, with 7 showing P<10$^{-12}$ (Table 1). The strongest associations were for three SNPs in strong linkage disequilibrium located within intron 23, (4<OR<5, recessive model; P ranging from 2×10$^{-18}$ to <10$^{-20}$). For the seven most highly associated SNPs, the susceptible allele was very frequent both in African-Americans (29% to 91%) and in YRI (40% to 97%), but much less frequent (3% to 52%) in European-Americans. While the results were not corrected for multiple comparisons, these associations would remain highly significant after any plausible correction.

Inferred haplotypes for MYH9 SNPs were analyzed, both within and extending beyond haplotype blocks defined from phase 1 HapMap data$^{42}$, for FSGS association (Supplemental Table S1). The strongest risk association was for the most frequent haplotype (haplotype E-1) for a block containing the three intron 23 SNPs and rs3752462 (OR=5.0 and P=4×10$^{-23}$, for combined idiopathic and HIV-associated FSGS) (Table 1). This haplotype had a frequency of 60% in African-Americans but only 4% in European-Americans.

The pattern of MYH9 SNP and haplotype associations is similar for HIV-associated FSGS and idiopathic FSGS in African-Americans (Table 3). The ORs for HIV-associated FSGS are somewhat stronger (e.g. the haplotype 1 recessive odds ratios are 5.9 for HIV+ vs. 4.7 for idiopathic FSGS), consistent with the greater racial disparity for HIV-associated FSGS, although the idiopathic associations are more significant (P=7×10$^{-8}$ for HIV-associated vs. 7×10$^{-16}$ for idiopathic FSGS), reflecting more idiopathic FSGS cases and controls.

Example 3

Separation of Ancestry Linkage Disequilibrium and Fine Mapping Association

Figure 1B:
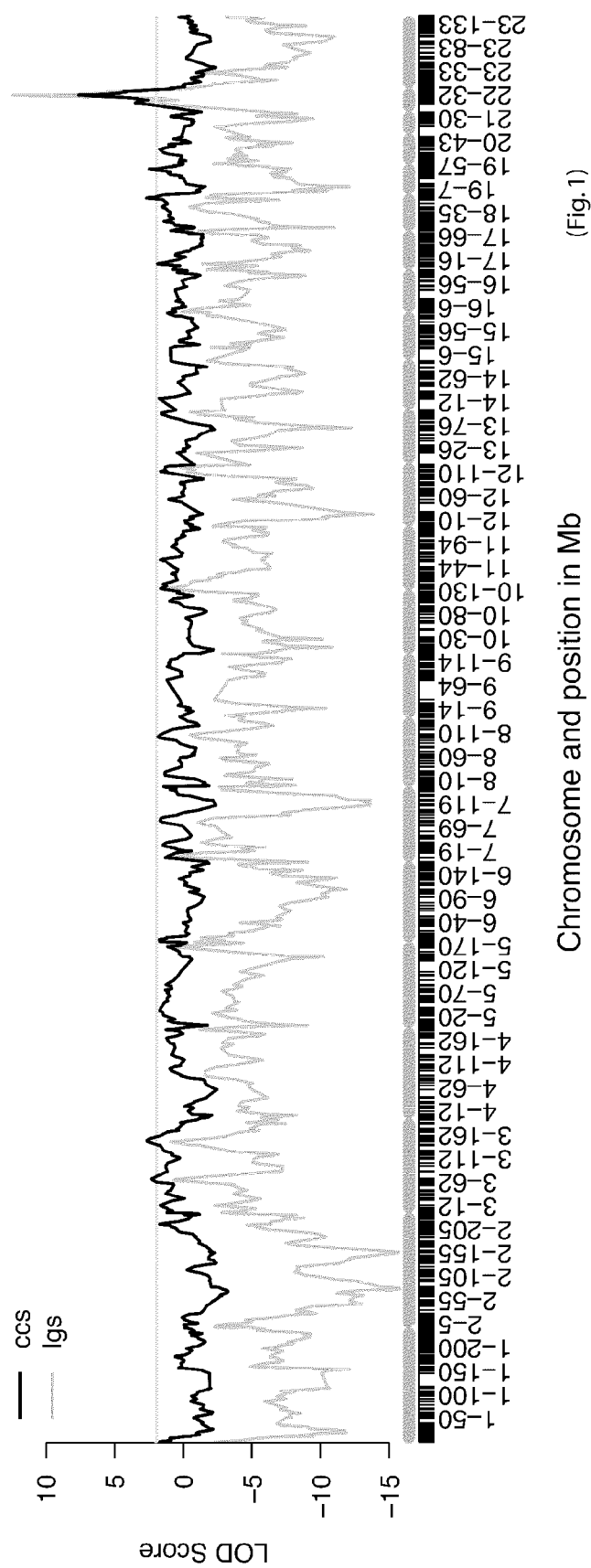
Figure 2:
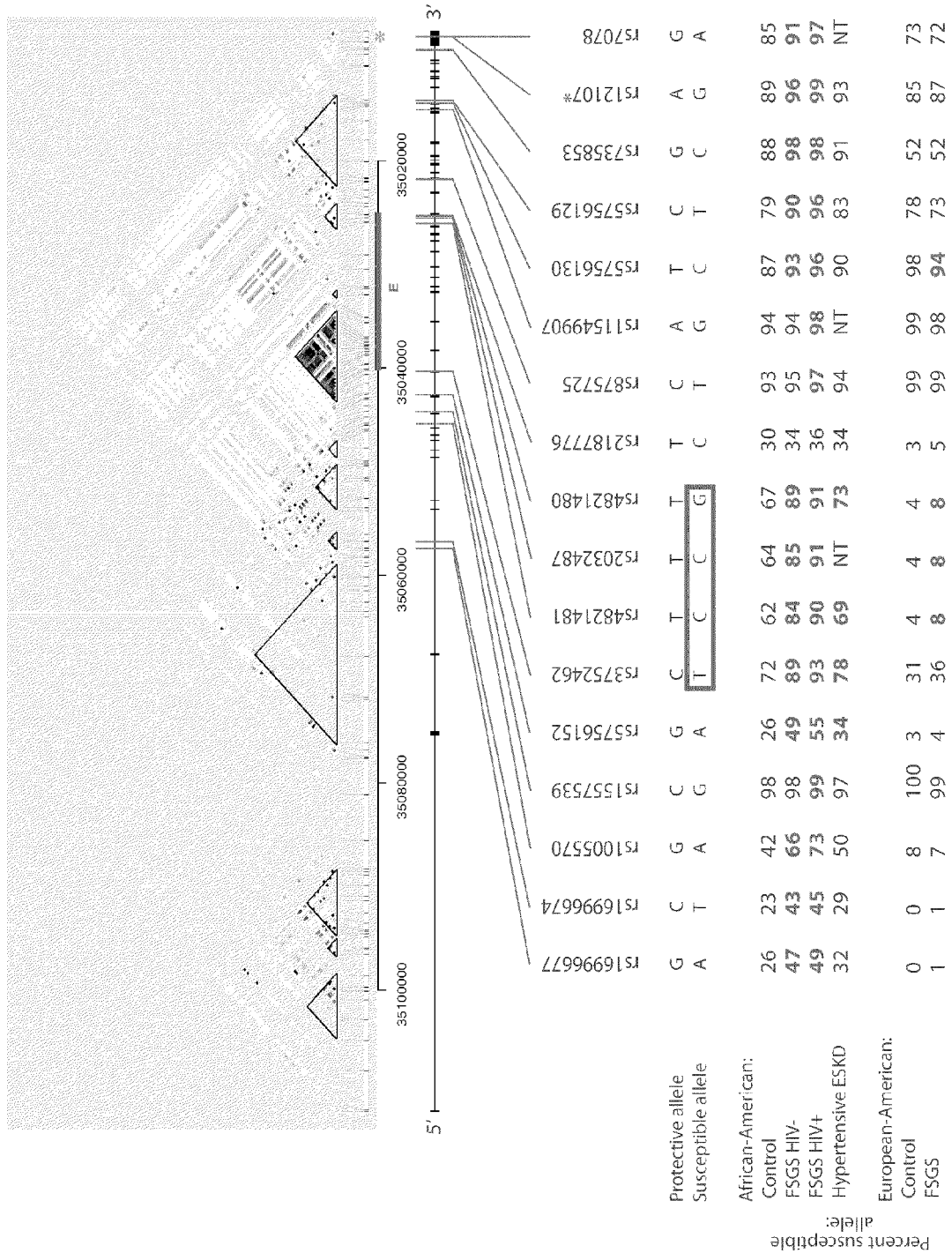
FIG. 2 is a schematic of MYH9.

To determine whether the associations of MYH9 SNPs resulted from admixture disequilibrium (typical length scale 2 Mb) or local "fine mapping" disequilibrium (typical length scale 50 Kb), associations for SNP alleles alone were compared with those for SNP alleles plus estimated local chromosomal ancestry (Table 2, Supplementary FIG. 1). For the three intron 23 SNPs, 79% to 83% of the effect is attributable to the SNPs alone. Thus the majority of the association is due to association with the phenotype, and only a small fraction of the association is tracking African ancestry. While these results do not rule out chromosome 22 associations distant from MYH9, they do point to fine-mapping association, implicating a functional polymorphism in or close to MYH9.

The association analysis was repeated limited to African-American individuals carrying two African chromosomes with probability >95% at the locus considered, as determined by ANCESTRYMAP®. By restricting the analysis to individuals with only African ancestry at the locus, the effects of admixture was eliminated in the association analysis. Analyses were done for each of 17 MYH9 SNPs and for 12 SNPs in four additional genes present under the MALD peak. Eleven of twenty-one MYH9 SNPs retained significant associations in this analysis, with 5 having P<0.0001, while none of the 12 comparison SNPs showed significance (P>0.07) (Table 2).

Example 4

Replication and Extension

The study population also contained 130 European-American FSGS subjects and 281 European-American controls, constituting an independent FSGS group for replication of the findings obtained in African-Americans. The three SNPs in intron 23 that were strongly associated with FSGS in African-Americans also show significant associations with FSGS in European-Americans, where they are in absolute linkage disequilibrium (r$^2$=1). The odds ratios are consistent in direction and strength, although the associations are much less significant, reflecting the low European-American frequency (~3%) of the susceptible alleles. SNP rs3752462 also showed a significant (P=0.01) association that was consistent in direction in European-Americans.

In order to determine whether MYH9 might harbor risk factors for ESKD attributed to hypertensive nephrosclerosis or diabetic nephrosclerosis, 14 MYH9 SNPs were typed on a cohort of African-Americans with ESKD reportedly due to non-diabetic etiologies (hypertension or chronic glomerular disease) and type 2 diabetes mellitus. Hypertensive (non-diabetic) ESKD associations (Table 3) were significant and consistent in direction with the FSGS associations for rs4821481 and rs5756152 and for haplotype 1, although odds ratios were smaller for carriers of either one or two susceptible risk alleles. SNP associations with hypertensive ESKD were independent of individuals' overall proportion of African ancestry. Significant associations were not observed with diabetes-associated ESKD (haplotype results in supplemental Table 1).

Example 5

MYH9 Localization within Podocytes

MYH9 transcripts are present in fetal and mature human kidneys; in situ hybridization shows highest expression in glomeruli, localized to podocytes (Arrondel, J Am Soc Nephrol 2002; 13(1):65-74). In mouse glomeruli, myosin II co-localizes with synaptopodin (FIG. 3A). In cultured human podocytes, myosin II co-localizes with actin and actin-associated proteins synaptopodin and Crk (FIGS. 3B, C, and D), but shows limited if any co-localization with slit-diaphragm protein nephrin (FIG. 3E).

The podocytopathies, including FSGS and collapsing glomerulopathy, involve genetic and acquired forms of podocyte injury (Barisoni et al., Clin J Am Soc Nephrol 2007; 2(3):529-42) and podocyte injury is proposed to play a central role in the pathogenesis of other progressive kidney diseases, including diabetes and hypertensive nephroclerosis (Wiggins, Kidney Int 2007; 71(12):1205-14). Over 10 genes have been associated with FSGS, most representing forms with Mendelian inheritance or evidence for new mutations. With regard to sporadic, non-familial FSGS, associations have been identified with WTI and NPHS2 (Orloff et al, supra, McKenzie et al., supra), but polymorphism in these genes explains only a small portion of the disease burden. In the study described herein, MALD was used to identify genetic variation in MYH9 as an important contributing factor to the development of idiopathic FSGS, HIV-associated FSGS, and hypertensive ESKD. The MALD scan revealed a single peak on chromosome 22q13.1 that showed strong association with FSGS in African-Americans. Fine mapping and functional considerations implicated MYH9. MYH9 susceptibility alleles are more frequent among African-Americans and neutral to protective alleles are more frequent among European-Americans, providing a possible explanation for the disparities in risk for FSGS and hypertensive ESKD in these populations. Since the patients with idiopathic FSGS lacked family members with FSGS, this suggests that MYH9 susceptibility alleles interact with one or more environmental factors (e.g. unidentified viruses or toxins) to induce podocyte injury.

Non-muscle myosin, like muscle myosin, is assembled from separately coded heavy and light chains and binds to actin to perform intracellular motor functions (Sellers, Biochim Biophys Acta 2000; 1496(1):3-22). Mutations in MYH9 have been associated with four clinical syndromes: May-Hegglin, Sebastian, Fechtner, and Epstein. All four syndromes involve autosomal dominant macrothrombocytopenia, with the variable accompaniment of sensorineural deafness, cataracts, neutrophil Döhle-like bodies, and glomerular disease (Dong et al., Br J Haematol 2005; 130(4):620-7). There are few histologic descriptions of MYH9-associated glomerular disease. One patient, undergoing kidney biopsy early in the disease course, had normal light microscopy and electron microscopic evidence of focal podocyte foot process effacement and loss of podocyte slit diaphragms, indicating podocyte injury (Ghiggeri et al., Am J Kidney Dis 2003; 41(1):95-104).

MYH9 knock-out mice are embryonic lethal, while heterogyous mice have apparent normal phenotype other than hearing loss with incomplete penetrance (Matsushita et al., Biochem Biophys Res Commun 2004; 325(4):1163-71). Myosin IIA has been localized to podocytes and possibly mesangial cells (Arrondel et al., J Am Soc Nephrol 2002; 13(1):65-74; Ghiggeri et al., Am J Kidney Dis 2003; 41(1):95-104). Other mutations in podocyte proteins which interact with the actin cytoskeleton, including alpha-actinin-4 (Kaplan et al., Nat Genet 2000; 24(3):251-6), CD2-associated protein (Kim et al, Science 2003; 300(5623):1298-300) and synaptopodin (Asanuma et al., Nat Cell Biol 2006; 8(5):485-91), have been associated with podocyte injury and FSGS in humans or experimental animals, suggesting the requirement for an intact actin cytoskeleton to maintain normal podocyte cytoarchitecture and filtration barrier function.

Our extension samples revealed that MYH9 was also associated with the common clinical syndrome "hypertensive nephrosclerosis" in African Americans, but not diabetic nephropathy. Patients with hypertensive ESKD typically present with advanced nephropathy and secondarily elevated blood pressure with resultant left ventricular hypertrophy and retinal vascular changes. Some of these individuals may have occult glomerular diseases, often FSGS or global glomerulosclerosis presenting in non-nephrotic forms, since they do not typically undergo renal biopsy (Freedman et al., Am J Kidney Dis 1995; 25(2):207-21; Zarif et al., Nephrol Dial Transplant 2000; 15(11):1801-7). Renal biopsy studies reveal the uniform presence of focal and/or global glomerulosclerosis in clinically diagnosed hypertensive nephrosclerosis (Fogo et al., Kidney Int 1997; 51(1):244-52) Importantly, the renal microvasculature changes that are typically attributed to hypertension fail to correlate with measured blood pressure, suggesting that factors other than hypertension caused nephropathy. In practice, cases are not often held to the strict diagnostic clinical criteria as in these reports, and hypertensive nephrosclerosis is a diagnosis of exclusion in many non-diabetic forms of nephropathy. It is likely that undiagnosed FSGS (Marcantoni et al., Kidney Int 2002; 62(1):172-80) or global glomerulosclerosis in those labeled with hypertensive nephrosclerosis contributed to the association. Patients with hypertension and with particular MYH9 alleles may be more susceptible to podocyte injury and progressive glomerular disease.

The present study using a MALD approach has securely identified a main effect gene that is involved in two histologically distinct forms of FSGS: idiopathic FSGS, which is characterized by depletion of podocytes, and HIV-1-associated FSGS (collapsing glomerulopathy), which is characterized by podocyte proliferation. Extrapolating to population data from this case control study, being a carrier of the frequent MYH9 susceptible haplotype has an attributable risk of 72% for sporadic FSGS and 100% for HIV-associated FSGS, as all subjects with HIV-associated FSGS carried the haplotype. The fractions of sporadic or HIV-associated FSGS that can be explained by this haplotype are 4.7% and 12%, respectively. In European-Americans, the risk haplotype is much less common than among African-Americans (allele frequency 4% vs. 60%), and the attributable fraction (4.9%) and explained fraction (0.5%) are much smaller. The difference in frequency of this haplotype provides a cause for the racial disparities observed with FSGS, HIV-associated nephropathy, and hypertensive nephrosclerosis in the African-Americans.

Example 6

MYH9 Gene Map

Table 7 shows intron-exon boundaries of the MYH9 gene, tag SNPs identified in the present disclosure associated with renal disease and the location of the tag SNPs in the reading strand. Table 7 also includes recessive OR for each tag SNP and the minimum p value for association. The significance group is defined by allele frequency and OR. The data was prepared using an OR for association with renal disease for recessive model and a p value for association with renal disease for recessive model. The tag SNPs identified as high significance have the strongest association with renal disease. The group identified as low significance has a lower (but nevertheless statistically significant) association with renal disease. A p value cut-off of $1\times10^{-5}$ was used to distinguish the high significance group from the low significance group.

Table 8 provides additional information for the tag SNPs when clustered as a high significance or low significance SNP. In particular, Table 8 identifies the risk allele and protective allele in the non-coding region of the MYH9 gene for each tag SNPs identified herein and the corresponding flanking sequencing.

While some very highly associated tag SNPs are found in introns of the MYH9 gene, several of the SNPs in exons are significantly associated with renal disease. In particular, tag SNPs were observed in non-coding regions of exons 14, 19, 26, 33, 34 and 41 of the MYH9 gene. This is explained by review of the location of the SNPs to determine that the tag SNPs are predominantly (greater than 95%) non-coding, i.e., they are in introns, or synonymous. The tag SNP identified in exon 41 (rs136196) is the most strongly associated tag SNP in an exon. Additionally, SNP rs2269529 of exon 34 codes for an amino acid change, an isoleucine to a valine. This change is considered to be a conservative substitution that only minimally changes the protein structure. Additionally, upon review of the data it was determined that all of the SNPs were observed to have an allele frequency for the risk allele in African Americans of greater than 5%.

In a further analysis, the observed $r^2$ values were compared with minimum p values to identify tag SNPs that are strongly associated with FSGS (p<0.01). One of the most strongly associated tag SNPs based on minimum p value (i.e., rs5750250) was used as a starting reference SNP. In a further study, an additional tag SNP close to the 3' end of the MYH9 gene (i.e., rs735854), was used as an additional starting reference SNP to identify tag SNPs strongly associated with FSGS. It was surprisingly observed that multiple tag SNPs identified herein at the 3' end of the MYH9 gene were independently associated with an elevated risk for the development of FSGS. This led to the conclusion that a tag SNP identified in the 3' end of the MYH9 gene possesses an independent association with renal disease.

Example 7

European American Associations

Table 9 provides 13 tag SNPs with p<0.05 for association with FSGS in European Americans. Table 9 identifies the recessive p value for each tag SNP, the position of the tag SNP in the MYH9 gene and whether the tag SNP was found in an intron or exon.

Example 8

Nucleic Acid-Based Analysis

The methods disclosed herein are used for evaluating if a subject has or is at risk for developing renal disease. For example, the methods can be used to determine if a subject is at risk for FSGS, or is at risk for hypertensive end-stage kidney disease.

In one example, a sample including nucleic acids can be obtained from a subject who is suspected to have a genetic predisposition to renal disease, such as FSGS or hypertensive end-stage kidney disease. The subject can have family members who have had FSGS or hypertensive renal disease. In another example, a sample including nucleic acids can be obtained from a subject that is of African ancestry. In a further example, a sample included nucleic acids is obtained from a subject with African (such as African American) ancestry who is infected with HIV.

In a further example, a sample including nucleic acids is obtained from a subject who has renal disease, wherein it is of interest to determine if the subject has hypertensive end-stage kidney disease. For example, a sample can be obtained from a subject who presents with a reduced glomerular filtration rate (GFR) or other laboratory evidence of renal impairment (such as elevated blood urea nitrogen (BUN) or abnormal renal histology), or someone with the clinical presentation (symptoms) of renal disease, such as fatigue and liquid retention. Additional indicators of renal disease that can suggest chronic renal failure include hyperkalemia, acidemia, elevated serum creatinine levels and/or the uremic syndrome. A renal biopsy can be obtained from the subject to determine if the subject has FSGS or hypertensive nephrosclerosis.

In some particular embodiments of the method, the subject is seropositive for the HIV virus, and the test is performed to predict whether the subject is likely to develop renal disease, such as chronic renal failure, such as renal failure caused by FSGS. In other embodiments, the subject is someone who has clinical and laboratory evidence of early renal disease and the genetic test is performed to confirm the diagnosis of renal disease. For example, the subject may be an African American with clinical evidence of early renal failure without a known etiology. Alternatively, the subject may have had a renal biopsy performed with inconclusive or ambiguous results. In these instances, the genetic test is performed to arrive at a diagnosis of chronic renal disease (or FSGS) with a higher degree of clinical certainty than would otherwise be possible. The genetic test can be used in association with other clinical signs and symptoms to assign a diagnosis, and from the diagnosis greater prognostic certainty can be provided to the subject. Alternatively, the genetic test can be used to provide a more specific diagnosis or etiology for chronic renal failure, as may be needed in research studies or for the selection of an appropriate therapeutic regimen.

In some examples a sample including nucleic acids is obtained from a subject with lupus nephritis or sickle cell anemia. These subjects can be tested to determine their haplotype at the time of diagnosis. In other examples a sample including nucleic acids is obtained from a subject with diabetes mellitus (type 1 or type 2), IgA nephropathy, and/or renal vasculitis.

The finding of a susceptibility haplotype can initiate screening annually or biannually for protein, using albumin/creatinine ratio, such as beginning at about age 12 or about age 15. For example, subjects who are found to have a condition that is associated with renal injury, including prematurity, small birth weight, obesity, hypertension, systemic lupus erythematosus, sickle cell anemia, diabetes mellitus, and HIV-1 infection can be screened using the methods disclosed herein.

To perform the method, a biological sample of the subject is assayed. The sample can, for example, be a blood sample or a buccal sample. Methods of isolating nucleic acid molecules from a biological sample are routine, for example using PCR to amplify the molecules from the sample, or by using a commercially available kit to isolate DNA. Nucleic acid molecules isolated from PBMCs or any other biological sample can be amplified using routine methods to form nucleic acid amplification products.

The ParAllele™ platform (Affymetrix, Santa Clara, Calif.) is used to genotype the sample of interest. It is determined if the individual has a risk allele associated with a tag SNP, such as a tag SNP listed in one or more of Tables 4-8. For example, it can be determined if the subject has a haplotype including one or more of the following tag SNPs: a G at rs4821480; a C at rs4821481; an A at rs1005570; a C at rs2032487; an A at rs5756152; an A it rs16996677; a T at rs3752462; a T at rs16996674; a C at rs735853; a T at rs5756129; a G at rs12107; an A at rs7078; a C at rs5756130; an A at rs9619601; a T at rs875725 and combinations thereof. The presence of the haplotype indicates that the subject is at risk for developing renal disease. For example, the methods can be used to determine if a subject is at risk for FSGS, or is at risk for hypertensive end-stage kidney disease.

In another embodiment, the methods can be used to identify protective alleles in a subject that are associated with the absence of renal disease. In this instance, the detection of protective alleles in a biological sample may be indicative of a lower risk for developing renal disease in the subject.

Example 9

Nucleic Acid-Based Analysis

The methods disclosed herein are used for evaluating if a subject has or is at risk for developing a particular disease or disorder. For example, the methods disclosed herein can be used to determine if a subject is at risk for developing asthma, sickle cell anemia, glaucoma, cerebral malaria, lacunar stroke, hypertension, human immunodeficiency virus, systemic sclerosis, diabetes mellitus, preeclampsia or systemic lupus erythematosus.

In one example, a sample including nucleic acids can be obtained from a subject who is suspected to have a genetic predisposition to asthma, sickle cell anemia, glaucoma, cerebral malaria, lacunar stroke, hypertension, human immunodeficiency virus, systemic sclerosis, diabetes mellitus, preeclampsia or systemic lupus erythematosus. The subject can have family members who have had one or more of the above diseases. In another example, a sample including nucleic acids can be obtained from a subject that is of African ancestry. In a further example, a sample includes nucleic acids obtained from a subject with European ancestry.

In a further example, a sample including nucleic acids is obtained from a subject who has, or who has suffered from, asthma, sickle cell anemia, glaucoma, cerebral malaria, lacunar stroke, hypertension, human immunodeficiency virus, systemic sclerosis, diabetes mellitus, preeclampsia or systemic lupus erythematosus and wherein it is of interest to monitor progression of one or more of the above diseases in the subject. For example, a sample can be obtained from a subject who presents with symptoms of one of the above disease's or who presents with elevated pulmonary hypertension for example in the case of asthma and sickle cell anemia, elevated intracranial pressure in the case of cerebral malaria and lacunar stroke, or elevated intraocular pressure in the case of glaucoma.

In some embodiments of the method, the subject is someone who has clinical or laboratory evidence of early disease such as blurred vision in glaucoma, a HIV seropositive test result or a child with periods of sudden pain that is often associated with sickle cell disease, and the genetic test is performed to confirm the diagnosis of the disease. For example, the subject may be an African American with clinical evidence of early optic nerve failure without a known etiology. Alternatively, the subject may have had a tissue biopsy performed with inconclusive or ambiguous results. In these instances, the genetic test is performed to arrive at a diagnosis of disease with a higher degree of clinical certainty than would otherwise be possible. The genetic test can be used in association with other clinical signs and symptoms to assign a diagnosis, and from the diagnosis greater prognostic certainty can be provided to the subject. Alternatively, the genetic test can be used to provide a more specific diagnosis or etiology for the disease under investigation, as may be needed in research studies or for the selection of an appropriate therapeutic regimen.

To perform the method, a biological sample of the subject is assayed. The sample can, for example, be a blood sample, tissue or a buccal sample. Methods of isolating nucleic acid molecules from a biological sample are routine, for example using PCR to amplify the molecules from the sample, or by using a commercially available kit to isolate DNA. Nucleic acid molecules isolated from PBMCs or any other biological sample can be amplified using routine methods to form nucleic acid amplification products.

The ParAllele™ platform (Affymetrix, Santa Clara, Calif.) is used to genotype the sample of interest. It is determined if the individual has a risk allele associated with a tag SNP, such as a tag SNP listed in any one of Tables 4-8. For example, it may be determined that the subject has a haplotype including one or more of the following tag SNPs: a G at rs4821480; a C at rs4821481; an A at rs1005570; a C at rs2032487; an A at rs5756152; an A it rs16996677; a T at rs3752462; a T at rs16996674; a C at rs735853; a T at rs5756129; a G at rs12107; an A at rs7078; a C at rs5756130; an A at rs9619601; a T at rs875725 and combinations thereof. The presence of the haplotype indicates that the subject is at risk for developing the disease under investigation. For example, the methods disclosed herein can be used to determine if a subject is at risk for asthma, sickle cell anemia, glaucoma, cerebral malaria, lacunar stroke, hypertension, human immunodeficiency virus, systemic sclerosis, diabetes mellitus, preeclampsia or systemic lupus erythematosus In another embodiment, the methods disclosed herein can be used to identify protective alleles in a subject that are associated with the absence of one or more of the above diseases. In this instance, detection of protective alleles in a biological sample may be indicative of a lower risk for developing one or more of the above diseases in the subject from whom the sample was derived.

It will be apparent that the precise details of the methods or compositions described may be varied or modified without departing from the spirit of the described invention. We claim all such modifications and variations that fall within the scope and spirit of the claims below.

The invention claimed is:

1. A method for detecting a genetic predisposition to focal segmental glomerulosclerosis (FSGS) in a human subject and administering an angiotensin-converting enzyme (ACE) inhibitor to the human subject, comprising:
    obtaining a sample from the subject comprising DNA;
    contacting the DNA with a primer or probe for at least one single nucleotide polymorphism (SNP) in a non-coding region of a MYH9 gene encoding non-muscle myosin heavy chain IIA comprising rs5750250;
    genotyping the sample obtained from the subject for the at least one SNP comprising rs5750250;
    detecting two copies of guanine (G) at rs5750250, as compared to a human subject with no G or a single copy of G at rs5750250, thereby determining that the subject has a genetic predisposition to FSGS; and
    administering the ACE inhibitor to the human subject with the genetic predisposition to FSGS.

2. The method of claim 1, wherein the human subject is infected with human immunodeficiency virus (HIV).

3. The method of claim 1, wherein the subject is an African-American subject who resides in the United States and self-identifies as being of African origin.

4. The method of claim 1, further comprising determining albumin content of a urine sample from the subject.

5. The method of claim 1, further comprising determining a concentration of creatinine in a serum sample from the subject.

* * * * *